US011634400B2

(12) United States Patent
Fasan et al.

(10) Patent No.: US 11,634,400 B2
(45) Date of Patent: Apr. 25, 2023

(54) MICHELIOLIDE DERIVATIVES, METHODS FOR THEIR PREPARATION AND THEIR USE AS ANTICANCER AND ANTIINFLAMMATORY AGENTS

(71) Applicant: University of Rochester, Rochester, NY (US)

(72) Inventors: Rudi Fasan, Rochester, NY (US); Simone Giovani, Grosseto (IT); Hanan Alwaseem, Dearborn, MI (US)

(73) Assignee: University of Rochester, Rochester, NY (US)

( * ) Notice: Subject to any disclaimer, the term of this patent is extended or adjusted under 35 U.S.C. 154(b) by 339 days.

(21) Appl. No.: 16/640,138

(22) PCT Filed: Aug. 17, 2018

(86) PCT No.: PCT/US2018/046856
§ 371 (c)(1),
(2) Date: Feb. 19, 2020

(87) PCT Pub. No.: WO2019/040335
PCT Pub. Date: Feb. 28, 2019

(65) Prior Publication Data
US 2020/0277270 A1 Sep. 3, 2020

Related U.S. Application Data

(60) Provisional application No. 62/547,806, filed on Aug. 19, 2017.

(51) Int. Cl.
*C07D 307/93* (2006.01)
*A61P 35/02* (2006.01)
*A61P 35/00* (2006.01)
*C12N 9/02* (2006.01)

(52) U.S. Cl.
CPC ............ *C07D 307/93* (2013.01); *A61P 35/00* (2018.01); *A61P 35/02* (2018.01); *C12N 9/0081* (2013.01); *C12Y 114/15006* (2013.01)

(58) Field of Classification Search
CPC ......... C07D 307/93; A61P 35/00; A61P 35/02
See application file for complete search history.

(56) References Cited

U.S. PATENT DOCUMENTS

| | | |
|---|---|---|
| 7,312,242 B2 | 12/2007 | Crooks |
| 7,678,904 B2 | 3/2010 | Crooks |
| 8,124,652 B2 | 2/2012 | Crooks |
| 9,255,078 B2 | 2/2016 | Chen |
| 2016/0367525 A1 | 12/2016 | Chen |

FOREIGN PATENT DOCUMENTS

| | | |
|---|---|---|
| CN | 103417532 | 12/2013 |
| WO | 2017128163 | 8/2017 |

OTHER PUBLICATIONS

Deane. Best Practice & Research Clinical Pharmacology, 2013, 27, 467-485. (Year: 2013).*
Ogura. Phytochemistry, 1978, 17, 957-961 (Year: 1978).*
Anderson and Bejcek, Parthenolide induces apoptosis in glioblastomas without affecting NF-kappaB, J Pharmacol Sci. 2008, 106(2): 318-320.
Baeuerle and Henkel, Function and activation of NF-kappa B in the immune system, Ann. Rev. Immunol. 1994, 12:141-179.
Barnes and Adcock, NF-kappa B: a pivotal role in asthma and a new target for therapy, Trends Pharm. Sci. 1997, 18(2): 46-50.
Barnes and Karin, Nuclear factor-kappaB: a pivotal transcription factor in chronic inflammatory diseases, NEJM 1997, 336(15): 1066-1071.
Bessho et al., A tRNA aminoacylation system for non-natural amino acids based on a programmable ribozyme, Nat Biotechnol 2002, 20(7): 723-728.
Bonnet and Dick, Human acute myeloid leukemia is organized as a hierarchy that originates from a primitive hematopoietic cell, Nat Med 1997, 3(7): 730-737.
Castaneda-Acosta et al., Biomimetic transformations of parthenolide, J Nat Prod 1993, 56(1): 90-98.
Cheng and Xie, Parthenolide induces apoptosis and cell cycle arrest of human 5637 bladder cancer cells in vitro, Molecules 2011, 16(8): 6758-6768.
Cirino, and Arnold, A self-sufficient peroxide-driven hydroxylation biocatalyst, Angew. Chem. Int. Ed. Engl. 2003, 42(28): 3299-3301.
Costello et al. Human acute myeloid leukemia CD34+/CD38- progenitor cells have decreased sensitivity to chemotherapy and Fas-induced apoptosis, reduced immunogenicity, and impaired dendritic cell transformation capacities, Cancer Research 2000, 60(16): 4403-4411.
Cox et al. Characterization of acute lymphoblastic leukemia progenitor cells, Blood 2004, 104(9): 2919-2925.
Cox et al., Rhodium(II) Trifluoroacetamide; an Excellent Catalyst for Carbenoid O—H Insertion Reactions, Syn let 1992(12): 975-976.
Dedkova, et al., Enhanced D-amino acid incorporation into protein by modified ribosomes, J. Am. Chem. Soc. 2003, 125(22): 6616-6617.
Estabrook, et al., Inhibition of NF-κB and DNA double-strand break repair by DMAPT sensitizes non-small-cell lung cancers to X-rays, Free Radic Biol Med 2011, 51(12): 2249-2258.

(Continued)

*Primary Examiner* — Noble E Jarrell
(74) *Attorney, Agent, or Firm* — Riverside Law LLP

(57) ABSTRACT

The present invention relates to derivatives of the sesquiterpene lactone micheliolide, methods and compositions for their preparation, and methods for using the micheliolide derivatives in pharmaceutical compositions as anticancer and anti-inflammatory agents. The invention also relates to methods for producing micheliolide derivatives modified at positions C2 and C14. The invention also relates to methods for producing parthenolide derivatives modified at positions C2 and C14 in conjunction with modifications at position C13, via chemoenzymatic methods. The invention further relates to methods for using parthenolide derivatives for treating cancer and inflammatory diseases.

14 Claims, 16 Drawing Sheets

Specification includes a Sequence Listing.

(56) References Cited

OTHER PUBLICATIONS

Galal, et al. Microbial transformation of parthenolide, Phytochemistry, 1999, 51(6): 761-765.
Garcia-Pineres, Cysteine 38 in p65/NF-kappaB plays a crucial role in DNA binding inhibition by sesquiterpene lactones, J Biol Chem 2001, 276(43): 39713-39720.
Garcia-Pineres, Role of cysteine residues of p65/NF-kappaB on the inhibition by the sesquiterpene lactone parthenolide and N-ethyl maleimide, and on its transactivating potential, Life Sci 2004, 75(7): 841-856.
Ghantous et al., What made sesquiterpene lactones reach cancer clinical trials?, Drug Discov Today, 2010 15(15-16): 668-678.
Gopal et al., Parthenolide promotes the ubiquitination of MDM2 and activates p53 cellular functions, Mol Cancer Ther 2009, 8(3): 552-562.
Gopal et al., Parthenolide specifically depletes histone deacetylase 1 protein and induces cell death through ataxia telangiectasia mutated, Chem Biol, 2007, 14(7): 813-823.
Graham et al., Primitive, quiescent, Philadelphia-positive stem cells from patients with chronic myeloid leukemia are insensitive to STI571 in vitro, Blood 2002, 99(1): 319-325.
Guan et al., Detection, isolation, and stimulation of quiescent primitive leukemic progenitor cells from patients with acute myeloid leukemia (AML), Blood 2003, 101(8): 3142-3149.
Guzman et al., A Novel Orally Available Parthenolide Analog Selectively Eradicates AML Stem and Progenitor Cells, Blood 2006, 108(11): 237 (abstract).
Guzman et al., Nuclear factor-kappaB is constitutively activated in primitive human acute myelogenous leukemia cells, Blood 2001, 98(8): 2301-2307.
Guzman et al., Preferential induction of apoptosis for primary human leukemic stem cells, PNAS 2002, 99(25): 16220-16225.
Guzman et al., Selective Induction of Apoptosis in Acute Myelogenous Leukemia Stem Cells by the Novel Agent Parthenolide, Blood 2004, 104(11): 2542 (abstract).
Guzman et al., The sesquiterpene lactone parthenolide induces apoptosis of human acute myelogenous leukemia stem and progenitor cells, Blood 2005, 105(11): 4163-4169.
Han et al., Semisynthetic derivatives of sesquiterpene lactones by palladium-catalyzed arylation of the alpha-methylene-gamma-lactone substructure, J. Org. Chem. 2009, 74(18): 7176-7179.
Hehner et al., Sesquiterpene lactones specifically inhibit activation of NF-kappa B by preventing the degradation of I kappa B-alpha and I kappa B-beta, J Biol Chem 1998, 273(3): 1288-1297.
Heptinstall et al., Extracts of feverfew inhibit granule secretion in blood platelets and polymorphonuclear leucocytes, Lancet 1985, 1(8437): 1071-1074.
Hirakawa and Nagamune, Molecular assembly of P450 with ferredoxin and ferredoxin reductase by fusion to PCNA, Chembiochem 2010, 11(11): 1517-1520.
Holcomb et al., Dimethylamino parthenolide enhances the inhibitory effects of gemcitabine in human pancreatic cancer cells, J Gastrointest Surg 2012, 16(7): 1333-1340.
Holyoake et al., Isolation of a highly quiescent subpopulation of primitive leukemic cells in chronic myeloid leukemia, Blood 1999, 94(6): 2056-2064.
Hwang et al., Inhibition of the expression of inducible cyclooxygenase and proinflammatory cytokines by sesquiterpene lactones in macrophages correlates with the inhibition of MAP kinases, 1996, Biochem Biophys Res Commun 226(3): 810-818.
Hwang et al., Synthesis and anti-viral activity of a series of sesquiterpene lactones and analogues in the subgenomic HCV replicon system, 2006, Bioorganic & Medicinal Chemistry 14(1): 83-91.
Idris et al., Pharmacologic inhibitors of IkappaB kinase suppress growth and migration of mammary carcinosarcoma cells in vitro and prevent osteolytic bone metastasis in vivo, 2009, Mol Cancer Ther 8(8): 2339-2347.

Janecka et al, Natural and synthetic α-methylenelactones and α-methylenelactams with anticancer potential, 2012, Drug Discov Today 17(11-12): 561-572.
Juliana et al., Anti-inflammatory compounds parthenolide and Bay 11-7082 are direct inhibitors of the inflammasome, 2010, J Biol Chem 285(13): 9792-9802.
Kawasaki et al., Effects of the sesquiterpene lactone parthenolide on prostate tumor-initiating cells: An integrated molecular profiling approach, 2009, Prostate 69(8): 827-837.
Killmann, Acute leukaemia: development, remission/relapse pattern, relationship between normal and leukaemic haemopoiesis, and the 'sleeper-to-feeder' stem cell hypothesis, 1991, Baillieres Clin Haematol 4(3): 577-598.
Kim et al., Parthenolide-induced apoptosis of hepatic stellate cells and anti-fibrotic effects in an in vivo rat model, 2012, Exp Mol Med 44(7): 448-456.
Kim et al., Susceptibility of cholangiocarcinoma cells to parthenolide-induced apoptosis, 2005, Cancer Res 65(14): 6312-6320.
Knight, Feverfew: chemistry and biological activity, 1995, Nat Prod Rep 12(3): 271-276.
Kourouklis, et al., Programmable ribozymes for mischarging tRNA with nonnatural amino acids and their applications to translation, 2005, Methods 36(3): 239-244.
Kreuger et al., Sesquiterpene lactones as drugs with multiple targets in cancer treatment: focus on parthenolide, 2012, Anticancer Drugs 23(9): 883-896.
Kwok et al., The anti-inflammatory natural product parthenolide from the medicinal herb Feverfew directly binds to and inhibits IkappaB kinase, 2001, Chem Biol 8(8): 759-766.
Landwehr et al, Diversification of catalytic function in a synthetic family of chimeric cytochrome p450s, 2007, Chem. Biol. 14(3): 269-278.
Lapidot et al., A cell initiating human acute myeloid leukaemia after transplantation into SCID mice, 1994, Nature 367(6464): 645-648.
Lesiak et al., Parthenolide, a sesquiterpene lactone from the medical herb feverfew, shows anticancer activity against human melanoma cells in vitro, 2010, Melanoma Res 20(1): 21-34.
Li et al., Parthenolide induces apoptosis and lytic cytotoxicity in Epstein-Barr virus-positive Burkitt lymphoma, 2012, Mol Med Rep 6(3): 477-482.
Li et al., Engineering and analysis of a self-sufficient biosynthetic cytochrome P450 PikC fused to the RhFRED reductase domain, 2007, J. Am. Chem. Soc. 129(43): 12940-12941.
Liu and Schultz, Adding new chemistries to the genetic code, 2010, Annu. Rev. Biochem. 79: 413-444.
Liu et al., A potential target associated with both cancer and cancer stem cells: a combination therapy for eradication of breast cancer using vinorelbine stealthy liposomes plus parthenolide stealthy liposomes, 2008, J Control Release 129(1): 18-25.
Liu et al., Modulation of DNA methylation by a sesquiterpene lactone parthenolide, 2009, J Pharmacol Exp Ther 329(2): 505-514.
Merfort, Perspectives on sesquiterpene lactones in inflammation and cancer, 2011, Current Drug Targets 12(11): 1560-1573.
Murakami et al., A highly flexible tRNA acylation method for non-natural polypeptide synthesis, 2006, Nat Methods 3(5): 357-359.
Nakshatri et al., Antitumor agent parthenolide reverses resistance of breast cancer cells to tumor necrosis factor-related apoptosis-inducing ligand through sustained activation of c-Jun N-terminal kinase, 2004, Oncogene 23(44): 7330-7344.
Nasim and Crooks, Antileukemic activity of aminoparthenolide analogs, 2008, Bioorg Med Chem Lett 18(14): 3870-3873.
Neelakantan et al., Aminoparthenolides as novel anti-leukemic agents: Discovery of the NF-kappaB inhibitor, DMAPT (LC-1), 2009, Bioorg. Med. Chem. Lett. 19(15): 4346-4349.
Neukirch et al., Parthenolide and its photochemically synthesized 1(10)Z isomer: chemical reactivity and structure-activity relationship studies in human leucocyte chemotaxis, 2003, Bioorg Med Chem 11(7): 1503-1510.
Neumann et al., Encoding multiple unnatural amino acids via evolution of a quadruplet-decoding ribosome, 2010, Nature 464(7287): 441-444.

(56) References Cited

OTHER PUBLICATIONS

Oka et al., 2007, Sesquiterpene lactone parthenolide suppresses tumor growth in a xenograft model of renal cell carcinoma by inhibiting the activation of NF-kappaB, International Journal of Cancer 120(12): 2576-2581.
Otey et al., Structure-guided recombination creates an artificial family of cytochromes P450, 2006, PLoS Biol. 4(5): e112, 10 pages.
Park et al., Identification of the genes involved in enhanced fenretinide-induced apoptosis by parthenolide in human hepatoma cells, 2005, Cancer Res 65(7): 2804-2814.
Patel et al., Paclitaxel sensitivity of breast cancer cells with constitutively active NF-kappaB is enhanced by IkappaBalpha super-repressor and parthenolide, 2000, Oncogene 19(36): 4159-4169.
Peddibhotla et al., Simultaneous Arming and Structure/Activity Studies of Natural Products Employing O—H Insertions: An Expedient and Versatile Strategy for Natural Products-Based Chemical Genetics, 2007, Journal of the American Chemical Society 129(40): 12222-12231.
Ralstin et al., Parthenolide Cooperates with NS398 to Inhibit Growth of Human Hepatocellular Carcinoma Cells through Effects on Apoptosis and G0-G1 Cell Cycle Arrest, 2006, Mol Cancer Res 4(6): 387-399.
Rodriguez et al., In vivo incorporation of multiple unnatural amino acids through nonsense and frameshift suppression, 2006, Proc Natl Acad Sci U S A 103(23): 8650-8655.
Shanmugam et al., A water soluble parthenolide analog suppresses in vivo tumor growth of two tobacco-associated cancers, lung and bladder cancer, by targeting NF-κB and generating reactive oxygen species, 2011, Int J Cancer 128(10): 2481-2494.
Shanmugam et al., A water-soluble parthenolide analogue suppresses in vivo prostate cancer growth by targeting NFkappaB and generating reactive oxygen species, 2010, Prostate 70(10): 1074-1086.
Siedle et al., 2004, Quantitative structure-activity relationship of sesquiterpene lactones as inhibitors of the transcription factor NF-kappaB, J Med Chem 47(24): 6042-6054.
Skalska et al., Modulation of cell surface protein free thiols: a potential novel mechanism of action of the sesquiterpene lactone parthenolide, 2009, PLoS One 4(12): e8115, 8 pages.
Steele et al., The sesquiterpene lactone parthenolide induces selective apoptosis of B-chronic lymphocytic leukemia cells in vitro, 2006, Leukemia 20(6): 1073-1079.
Sun et al., A NADPH oxidase-dependent redox signaling pathway mediates the selective radiosensitization effect of parthenolide in prostate cancer cells, 2010, Cancer Res 70(7): 2880-2890.
Sun et al., Cytotoxic sesquiterpene lactones from the root of Saussurea lappa, 2003, J Nat Prod 66(9): 1175-1180.
Sun et al., The radiosensitization effect of parthenolide in prostate cancer cells is mediated by nuclear factor-kappaB inhibition and enhanced by the presence of PTEN, 2007, Mol Cancer Ther 6(9): 2477-2486.
Suvannasankha et al., Antimyeloma effects of a sesquiterpene lactone parthenolide, 2008, Clin Cancer Res 14(6): 1814-1822.
Sweeney et al., The sesquiterpene lactone parthenolide in combination with docetaxel reduces metastasis and improves survival in a xenograft model of breast cancer, 2005, Mol Cancer Ther 4(6): 1004-1012.
Tiuman et al., Antileishmanial activity of parthenolide, a sesquiterpene lactone isolated from Tanacetum parthenium, 2005, Antimicrobial Agents and Chemotherapy 49(1): 176-182.
Tran et al., Light-initiated hydroxylation of lauric acid using hybrid P450 BM3 enzymes, 2011, Chem Commun (Camb) 47(43): 11936-11938.
Van der Donk and Zhao, Recent developments in pyridine nucleotide regeneration, 2003, Curr Opin Biotechnol 14(4): 421-426.
Van Rhenen et al., High stem cell frequency in acute myeloid leukemia at diagnosis predicts high minimal residual disease and poor survival, 2005, Clin Cancer Res 11(18): 6520-6527.
Wang et al., A novel combination therapy with arsenic trioxide and parthenolide against pancreatic cancer cells, 2009, Pancreas 38(4): e114-123.
Wang et al., Parthenolide-induced apoptosis in multiple myeloma cells involves reactive oxygen species generation and cell sensitivity depends on catalase activity, 2006, Apoptosis 11(12): 2225-2235.
Wei-Wei et al., Synthesis of Micheliolide Derivatives and Their Activities Against AML Progenitor Cells, Molecules 2013, 18(5):5980-92.
Wen et al., Oxidative stress-mediated apoptosis. The anticancer effect of the sesquiterpene lactone parthenolide, 2002, J Biol Chem 277(41): 38954-38964.
Won et al., Chemopreventive activity of parthenolide against UVB-induced skin cancer and its mechanisms, 2004, Carcinogenesis 25(8): 1449-1458.
Won et al., Parthenolide sensitizes ultraviolet (UV)-B-induced apoptosis via protein kinase C-dependent pathways, 2005, Carcinogenesis 26(12): 2149-2156.
Woods et al., Fluorinated amino-derivatives of the sesquiterpene lactone, parthenolide, as (19)f NMR probes in deuterium-free environments, 2011, J Med Chem 54(22): 7934-7941.
Wyrebska et al., Comparison of anti-invasive activity of parthenolide and 3-isopropyl-2-methyl-4-methyleneisoxazolidin-5-one (MZ-6)—a new compound with α-methylene-γ-lactone motif—on two breast cancer cell lines, 2012, Chem Biol Drug Des 79(1): 112-120.
Yip-Schneider et al., Effect of celecoxib and the novel anti-cancer agent, dimethylamino-parthenolide, in a developmental model of pancreatic cancer, 2008, Pancreas 37(3): e45-53.
Yip-Schneider et al., Parthenolide and sulindac cooperate to mediate growth suppression and inhibit the nuclear factor-kappa B pathway in pancreatic carcinoma cells, 2005, Mol Cancer Ther 4(4): 587-594.
Young-Won Chin et al., Cytotoxic Anticancer Candidates from Terrestrial Plants, Anticancer Agents Med Chem. 2009, 9(8):913-42.
Zanotto-Filho et al., NFκB inhibitors induce cell death in glioblastomas, 2011, Biochemical Pharmacology 81(3): 412-424.
Zhang et al., Controlled oxidation of remote sp3 C—H bonds in artemisinin via P450 catalysts with fine-tuned regio- and stereoselectivity, 2012, J Am Chem Soc 134(45): 18695-18704.
Zhang et al., Critical roles of intracellular thiols and calcium in parthenolide-induced apoptosis in human colorectal cancer cells, 2004, Cancer Lett 208(2): 143-153.
Zhang et al., Guaianolide sesquiterpene lactones, a source to discover agents that selectively inhibit acute myelogenous leukemia stem and progenitor cells, J. Med. Chem. 2012, 55(20):8757-69.
Zhang et al., Involvement of proapoptotic Bcl-2 family members in parthenolide-induced mitochondrial dysfunction and apoptosis, 2004, Cancer Lett 211(2): 175-188.
Zhang et al., Nuclear factor-kappaB inhibition by parthenolide potentiates the efficacy of Taxol in non-small cell lung cancer in vitro and in vivo, 2009, Mol Cancer Res 7(7): 1139-1149.
Zhang et al., P450 fingerprinting method for rapid discovery of terpene hydroxylating P450 catalysts with diversified regioselectivity, 2011, J. Am. Chem. Soc. 133(10): 3242-3245.
Zhao and van der Donk, Regeneration of cofactors for use in biocatalysis, 2003, Curr Opin Biotechnol 14(6): 583-589.

\* cited by examiner

| $LD_{50}(\mu M)$ | Compound |
|---|---|
| 14.6 | MCL |
| 1.8 | SG-05 |
| 5.1 | SG-08 |
| 4.8 | SG-11 |
| 4.1 | SG-16 |
| 7 | SG-17 |
| 14.7 | SG-20 |
| 13.6 | SG-22 |
| 13.5 | SG-26 |
| 8.6 | SG-30 |
| 9.5 | SG-31 |
| 13.2 | SG-37 |
| 2.7 | SG-52 |
| 3.4 | SG-53 |
| 7 | SG-56 |
| 4.3 | SG-58 |
| 3.2 | SG-59 |

M9-ENL1

Figure 9

| Compound | AML01 LD$_{50}$ (μM) | AML02 LD$_{50}$ (μM) | AML03 LD$_{50}$ (μM) | AML04 LD$_{50}$ (μM) |
|---|---|---|---|---|
| MCL | 18.8 | 22.1 | 18.3 | 15.8 |
| SG-05 | 6.6 | 4.3 | 13.3 | 4.3 |
| SG-08 | 8.4 | 7.4 | 15.6 | 9.1 |
| SG-11 | 9.0 | 9.5 | 15.4 | 13.1 |
| SG-16 | 2.5 | 2.3 | 3.2 | 2.5 |
| SG-17 | 5.9 | 4.7 | 15.6 | 5.8 |
| SG-30 | 16.1 | 19.5 | 18.5 | 9.5 |
| SG-31 | 15.8 | 19.0 | 20.0 | 10.2 |

Figure 10

SEQUENCE LISTING

```
<160> NUMBER OF SEQ ID NOS: 7

<210> SEQ ID NO 1
<211> LENGTH: 1049
<212> TYPE: PRT
<213> ORGANISM: Bacillus megaterium

<400> SEQUENCE: 1

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125
```

```
Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540
```

-continued

```
Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
```

```
                    965                 970                 975
Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
        1010                1015                1020

Val Ser Glu Ala Asp Ala Arg Leu Trp Leu Gln Gln Leu Glu Glu
        1025                1030                1035

Lys Gly Arg Tyr Ala Lys Asp Val Trp Ala Gly
        1040                1045

<210> SEQ ID NO 2
<211> LENGTH: 1049
<212> TYPE: PRT
<213> ORGANISM: Bacillus megaterium

<400> SEQUENCE: 2

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Ser Val Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Thr Leu Asp Glu Val Met Asn Lys Leu Gln Arg Ala
            180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285
```

```
Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
```

-continued

```
            705                 710                 715                 720
        Leu Asp Ala Ser Gln Gln Ile Arg Leu Glu Ala Glu Glu Lys Leu
                        725                 730                 735

Ala His Leu Pro Leu Ala Lys Thr Val Ser Glu Glu Leu Leu Gln
                        740                 745                 750

Tyr Val Glu Leu Gln Asp Pro Val Thr Arg Thr Gln Leu Arg Ala Met
                        755                 760                 765

Ala Ala Lys Thr Val Cys Pro His Lys Val Glu Leu Glu Ala Leu
                        770                 775                 780

Leu Glu Lys Gln Ala Tyr Lys Glu Gln Val Leu Ala Lys Arg Leu Thr
        785                 790                 795                 800

Met Leu Glu Leu Leu Glu Lys Tyr Pro Ala Cys Glu Met Lys Phe Ser
                        805                 810                 815

Glu Phe Ile Ala Leu Leu Pro Ser Ile Arg Pro Arg Tyr Tyr Ser Ile
                        820                 825                 830

Ser Ser Ser Pro Arg Val Asp Glu Lys Gln Ala Ser Ile Thr Val Ser
                        835                 840                 845

Val Val Ser Gly Glu Ala Trp Ser Gly Tyr Gly Glu Tyr Lys Gly Ile
        850                 855                 860

Ala Ser Asn Tyr Leu Ala Glu Leu Gln Glu Gly Asp Thr Ile Thr Cys
        865                 870                 875                 880

Phe Ile Ser Thr Pro Gln Ser Glu Phe Thr Leu Pro Lys Asp Pro Glu
                        885                 890                 895

Thr Pro Leu Ile Met Val Gly Pro Gly Thr Gly Val Ala Pro Phe Arg
                        900                 905                 910

Gly Phe Val Gln Ala Arg Lys Gln Leu Lys Glu Gln Gly Gln Ser Leu
                        915                 920                 925

Gly Glu Ala His Leu Tyr Phe Gly Cys Arg Ser Pro His Glu Asp Tyr
                        930                 935                 940

Leu Tyr Gln Glu Glu Leu Glu Asn Ala Gln Ser Glu Gly Ile Ile Thr
        945                 950                 955                 960

Leu His Thr Ala Phe Ser Arg Met Pro Asn Gln Pro Lys Thr Tyr Val
                        965                 970                 975

Gln His Val Met Glu Gln Asp Gly Lys Lys Leu Ile Glu Leu Leu Asp
                        980                 985                 990

Gln Gly Ala His Phe Tyr Ile Cys Gly Asp Gly Ser Gln Met Ala Pro
                        995                 1000                1005

Ala Val Glu Ala Thr Leu Met Lys Ser Tyr Ala Asp Val His Gln
                        1010                1015                1020

Val Ser Glu Ala Asp Ala Arg Leu Trp Leu Gln Gln Leu Glu Glu
                        1025                1030                1035

Lys Gly Arg Tyr Ala Lys Asp Val Trp Ala Gly
                        1040                1045

<210> SEQ ID NO 3
<211> LENGTH: 1049
<212> TYPE: PRT
<213> ORGANISM: Bacillus megaterium

<400> SEQUENCE: 3

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
                20                  25                  30
```

-continued

Ile Ala Asp Glu Leu Gly Glu Ile Phe Lys Phe Glu Ala Pro Gly Cys
            35                  40                  45

Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Ala Val Arg
 65                  70                  75                  80

Asp Phe Ala Gly Asp Gly Leu Ile Thr Ser Thr His Glu Ile Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Ser Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr

```
            450              455              460
Glu Gln Ser Ala Lys Lys Val Arg Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880
```

-continued

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
                930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                1000                1005

Ala Val Glu Ala Thr Leu Met Lys Ser Tyr Ala Asp Val His Gln
        1010                1015                1020

Val Ser Glu Ala Asp Ala Arg Leu Trp Leu Gln Gln Leu Glu Glu
        1025                1030                1035

Lys Gly Arg Tyr Ala Lys Asp Val Trp Ala Gly
        1040                1045

<210> SEQ ID NO 4
<211> LENGTH: 1049
<212> TYPE: PRT
<213> ORGANISM: Bacillus megaterium

<400> SEQUENCE: 4

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
                20                  25                  30

Ile Ala Asp Glu Leu Gly Glu Ile Phe Lys Phe Glu Ala Pro Gly Cys
            35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Ala Val Arg
65                  70                  75                  80

Asp Phe Ala Gly Asp Gly Leu Ala Thr Ser Trp Thr His Glu Ile Asn
                85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu

-continued

```
                195                 200                 205
Asp Ile Lys Val Met Asn Asp Leu Val Asp Lys Ile Ile Ala Asp Arg
210                 215                 220
Lys Ala Arg Gly Glu Gln Ser Asp Asp Leu Leu Thr Gln Met Leu Asn
225                 230                 235                 240
Gly Lys Asp Pro Glu Thr Gly Glu Pro Leu Asp Asp Gly Asn Ile Ser
                245                 250                 255
Tyr Gln Ile Ile Thr Phe Leu Ile Ala Gly His Glu Thr Thr Ser Gly
                260                 265                 270
Leu Leu Ser Phe Ala Leu Tyr Phe Leu Val Lys Asn Pro His Val Leu
            275                 280                 285
Gln Lys Val Ala Glu Glu Ala Ala Arg Val Leu Val Asp Pro Val Pro
        290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Val Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
```

```
Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
        660                 665                 670

Leu Gln Gln Pro Gly Ser Ala Arg Ser Thr Arg His Leu Glu Ile Glu
    675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
        740                 745                 750

Tyr Val Glu Leu Gln Asp Pro Val Thr Arg Thr Gln Leu Arg Ala Met
    755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
        820                 825                 830

Ser Ser Ser Pro Arg Val Asp Glu Lys Gln Ala Ser Ile Thr Val Ser
    835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
        900                 905                 910

Gly Phe Val Gln Ala Arg Lys Gln Leu Lys Glu Gln Gly Gln Ser Leu
    915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
        980                 985                 990

Gln Gly Ala His Phe Tyr Ile Cys Gly Asp Gly Ser Gln Met Ala Pro
    995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035
```

```
Lys Gly Arg Tyr Ala Lys Asp  Val Trp Ala Gly
    1040                1045

<210> SEQ ID NO 5
<211> LENGTH: 1049
<212> TYPE: PRT
<213> ORGANISM: Bacillus megaterium

<400> SEQUENCE: 5

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Ala Ala Val Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Thr Leu Asp Glu Val Met Asn Lys Leu Gln Arg Ala
            180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
        355                 360                 365
```

-continued

```
Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
770                 775                 780
```

-continued

```
Leu Glu Lys Gln Ala Tyr Lys Glu Gln Val Leu Ala Lys Arg Leu Thr
785                 790                 795                 800

Met Leu Glu Leu Leu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
            995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 6
<211> LENGTH: 1049
<212> TYPE: PRT
<213> ORGANISM: Bacillus megaterium

<400> SEQUENCE: 6

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Asn Ala Arg
65                  70                  75                  80

Phe Ala Val Gly Asp Gly Leu Ala Thr Ser Trp Thr His Glu Lys Asn
            85                  90                  95

Trp Lys Lys Ala His Asn Ile Leu Leu Pro Ser Phe Ser Gln Gln Ala
            100                 105                 110
```

```
Met Lys Gly Tyr His Ala Met Met Val Asp Ile Ala Val Gln Leu Val
            115                 120                 125
Gln Lys Trp Glu Arg Leu Asn Ala Asp Glu His Ile Glu Val Ser Glu
130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Gln Pro His Pro Phe Ile Ile
                165                 170                 175
Ser Met Val Arg Thr Leu Asp Glu Val Met Asn Lys Leu Gln Arg Ala
                180                 185                 190
Asn Pro Asp Asp Pro Val Tyr Asp Glu Asn Lys Arg Gln Cys Gln Glu
            195                 200                 205
Asp Ile Lys Val Met Asn Asp Leu Val Asp Lys Ile Ile Ala Asp Arg
210                 215                 220
Lys Ala Arg Gly Glu Gln Ser Asp Asp Leu Leu Thr Gln Met Leu Asn
225                 230                 235                 240
Gly Lys Asp Pro Glu Thr Gly Glu Pro Leu Asp Asp Gly Asn Ile Ser
                245                 250                 255
Tyr Gln Ile Ile Thr Phe Leu Ile Ala Gly His Glu Thr Thr Ser Gly
                260                 265                 270
Leu Leu Ser Phe Ala Leu Tyr Phe Leu Val Lys Asn Pro His Val Leu
            275                 280                 285
Gln Lys Val Ala Glu Glu Ala Ala Arg Val Leu Val Asp Pro Val Pro
290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Tyr Pro Leu Glu Lys Gly Asp
                340                 345                 350
Glu Val Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
            435                 440                 445
Ala Lys Ser Lys Lys Ile Pro Leu Gly Gly Ile Pro Ser Pro Ser Thr
450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
            515                 520                 525
```

-continued

```
Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
```

Leu His Thr Ala Phe Ser Arg Met Pro Asn Gln Pro Lys Thr Tyr Val
945                 950                 955                 960

Gln His Val Met Glu Gln Asp Gly Lys Lys Leu Ile Glu Leu Leu Asp
        965                 970                 975

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 7
<211> LENGTH: 1049
<212> TYPE: PRT
<213> ORGANISM: Bacillus megaterium

<400> SEQUENCE: 7

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Thr Ala Leu Lys Asn Ala Arg
65                  70                  75                  80

Phe Ser Val Gly Asp Gly Phe Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Ala Thr Leu Asp Glu Val Met Asn Lys Leu Gln Arg Ala
            180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

-continued

```
Leu Leu Ser Phe Ala Leu Tyr Phe Leu Val Lys Asn Pro His Val Leu
        275                 280                 285

Gln Lys Val Ala Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
```

-continued

```
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
                995                 1000                1005

Ala Val Glu Ala Thr Leu Met Lys Ser Tyr Ala Asp Val His Gln
        1010                1015                1020

Val Ser Glu Ala Asp Ala Arg Leu Trp Leu Gln Gln Leu Glu Glu
        1025                1030                1035

Lys Gly Arg Tyr Ala Lys Asp Val Trp Ala Gly
        1040                1045
```

MICHELIOLIDE DERIVATIVES, METHODS FOR THEIR PREPARATION AND THEIR USE AS ANTICANCER AND ANTIINFLAMMATORY AGENTS

CROSS-REFERENCE TO RELATED APPLICATIONS

This application is the U.S. national phase application filed under 35 U.S.C. § 371 claiming priority to International Patent Application No. PCT/US2018/046856, filed Aug. 17, 2018, which is entitled to priority under 35 U.S.C. § 119(e) to U.S. Provisional Patent Application Ser. No. 62/547,806, filed Aug. 19, 2017, the disclosures of which are incorporated herein by reference in their entireties.

STATEMENT REGARDING FEDERALLY SPONSORED RESEARCH OR DEVELOPMENT

This invention was made with government support under GM095628 awarded by National Institutes of Health. The government has certain rights in the invention.

1. TECHNICAL FIELD

The present invention relates to derivatives of the sesquiterpene lactone micheliolide, methods and compositions for their preparation, and methods for using the micheliolide derivatives in pharmaceutical compositions as anticancer and anti-inflammatory agents. The invention also relates to methods for producing micheliolide derivatives modified at positions C2 and C14. The invention also relates to methods for producing parthenolide derivatives modified at positions C2 and C14 in conjunction with modifications at position C13, via chemoenzymatic methods. The invention further relates to methods for using parthenolide derivatives for treating cancer and inflammatory diseases.

2. BACKGROUND OF THE INVENTION

Sesquiterpene lactones (SL) are a diverse family of plant derived natural products with promising inflammatory and anticancer activity. Parthenolide (PTL) is a well-studied SL found in various genera of the Asteraceae and Magnoliaceae family. Parthenolide was found to exhibit a broad spectrum of biological properties, which include anti-inflammatory (Merfort 2011), antitumor (Ghantous, Gali-Muhtasib et al. 2010; Merfort 2011; Janecka, Wyrebska et al. 2012; Kreuger, Grootjans et al. 2012), antiviral (Hwang, Chang et al. 2006), and antileishmanic (Tiuman, Ueda-Nakamura et al. 2005) activity. The anti-inflammatory properties of parthenolide has been associated to its ability to inhibit the NF-κB transcription factor (Hehner, Heinrich et al. 1998; Garcia-Pineres, Castro et al. 2001; Garcia-Pineres, Lindenmeyer et al. 2004), which plays a prevalent role in regulating inflammatory responses (Baeuerle and Henkel 1994) as well as inhibition of other cellular mechanisms involved in inflammation, such as prostaglandin synthesis and IL-1α expression (Hwang, Fischer et al. 1996) and activation of the NLRP-3 inflammasome (Juliana, Femandes-Alnemri et al. 2010). Pharmacological inhibition of NF-κB activation, such as that induced by parthenolide, has been recognized as an important strategy for the treatment of a variety of inflammation-related pathologies, including toxic shock, asthma, and rheumatoid arthritis (Barnes and Adcock 1997; Barnes and Larin 1997). Parthenolide has been identified as the major active ingredient of the medicinal herb feverfew (Tanacetum parthenium), which has found use in the traditional medicine for the treatment of pain, migraine, and rheumatoid arthritis (Heptinstall, White et al. 1985; Knight 1995).

A growing number of studies over the past decade have demonstrated the therapeutic potential of parthenolide also as an anticancer agent. In particular, PTL has emerged as a very promising antileukemic agent owing to its ability to induce robust apoptosis in primary acute myeloid leukemic (AML) cells while exhibiting minimal toxicity toward normal hematopoietic cells (Guzman, Karnischky et al. 2004; Guzman, Rossi et al. 2005; Guzman, Rossi et al. 2006). Most notably, PTL was found to be equally effective amongst all subpopulations found within primary AML specimens, including the so-called leukemia stem cells (LSCs). LSCs typically occur in a quiescent state, which reduces their responsiveness to conventional chemotherapeutic agents that kill actively cycling cells (Holyoake, Jiang et al. 1999; Costello, Mallet et al. 2000; Graham, Jorgensen et al. 2002; Guzman, Swiderski et al. 2002; Guan, Gerhard et al. 2003). Thus, in addition to being involved in the genesis of AML (Lapidot, Sirard et al. 1994; Bonnet and Dick 1997; Cox, Evely et al. 2004), LSCs are believed to play a major role also in clinical relapse of AML patients following traditional chemotherapy (Killmann 1991; van Rhenen, Feller et al. 2005). Thus, the LSC-targeting ability of PTL makes this compound a particularly interesting candidate toward the development of therapeutics for the treatment of AML as well as of other hematologic malignancies.

In addition to AML, PTL has demonstrated activity against numerous other types of cancer. Indeed, recent studies showed that PTL exhibits notable antitumor properties also against breast (Patel, Nozaki et al. 2000; Nakshatri, Rice et al. 2004; Sweeney, Mehrotra et al. 2005; Liu, Lu et al. 2008; Wyrebska, Gach et al. 2012), lung (Zhang, Qiu et al. 2009; Estabrook, Chin-Sinex et al. 2011; Shanmugam, Kusumanchi et al. 2011), prostate (Sun, St Clair et al. 2007; Kawasaki, Hurt et al. 2009; Shanmugam, Kusumanchi et al. 2010; Sun, St Clair et al. 2010), blood (Steele, Jones et al. 2006; Wang, Adachi et al. 2006; Suvannasankha, Crean et al. 2008; Li, Zhang et al. 2012), colon (Zhang, Ong et al. 2004), bladder (Cheng and Xie 2011), liver (Wen, You et al. 2002; Park, Liu et al. 2005; Ralstin, Gage et al. 2006; Kim, Kim et al. 2012), skin (Won, Ong et al. 2004; Won, Ong et al. 2005; Lesiak, Koprowska et al. 2010), brain (Anderson and Bejcek 2008; Zanotto-Filho, Braganhol et al. 2011), pancreas (Kim, Liu et al. 2005; Yip-Schneider, Nakshatri et al. 2005; Yip-Schneider, Wu et al. 2008; Wang, Adachi et al. 2009; Holcomb, Yip-Schneider et al. 2012), kidney (Oka, Nishimura et al. 2007), and bone (Idris, Libouban et al. 2009) cancer.

The anticancer activity of PTL has been primarily linked to its inhibitory activity on NF-κB as this transcription factor controls multiple cellular processes in cancer, including inflammation, transformation, proliferation, angiogenesis, invasion, metastasis, chemoresistance, and radioresistance (Kreuger, Grootjans et al. 2012). However, additional and/or alternative mechanisms of action contribute to PTL anticancer activity, which include activation of p53 (Gopal, Chanchorn et al. 2009), induction of oxidative stress (Wen, You et al. 2002; Zhang, Ong et al. 2004; Wang, Adachi et al. 2006; Sun, St Clair et al. 2010; Shanmugam, Kusumanchi et al. 2011), inhibition of JNK (Nakshatri, Rice et al. 2004) activation of proapoptotic Bcl-2 family members (Zhang, Ong et al. 2004), modulation of exofacial thiols (Skalska, Brookes et al. 2009), and alteration of epigenetic mechanisms via inhibition of DNA methylation (Liu, Liu et al. 2009) and histone deacetylase activity (Gopal, Arora et al. 2007).

From a structure-activity standpoint, the α-methylene-γ-lactone moiety was found to be critically important for parthenolide pharmacological properties, as reduction of the α,β-unsaturated lactone to give 11,13-dehydroparthenolide results in complete loss of activity (Kwok, Koh et al. 2001; Hwang, Chang et al. 2006; Neelakantan, Nasim et al. 2009). The key functional role of this structural moiety is largely related to its ability to react with nucleophilic sulphydryl groups in the cellular components (e.g., enzymes, proteins, glutathione) targeted by PTL (Garcia-Pineres, Castro et al. 2001; Kwok, Koh et al. 2001; Garcia-Pineres, Lindenmeyer et al. 2004; Skalska, Brookes et al. 2009). Despite its interesting biological properties, PTL suffers from a number of drawbacks which include its scarce water-solubility and chemical instability upon exposure to acids (Castaneda-Acosta, Fischer et al. 1993; Neukirch, Kaneider et al. 2003; Nasim and Crooks 2008). These limitations complicate the development and application of PTL analogs as therapeutic agents.

Micheliolide (MCL, 1) is a guaianolide sesquiterpene lactone isolated from *Michelia compressa* [Ogura, M.; Cordell, G. A.; Farnsworth, N. R. Anticancer sesquiterpene lactones of *Michelia compressa* (magnoliaceae). Phytochemistry 1978, 17, 957-961] and *Michelia champaca* [Jacobsson, U.; Kumar, V.; Saminathan, S. Sesquiterpene lactones from *Michelia champaca*. Phytochemistry 1995, 39, 839-843]. MCL was recently found to possess antileukemic properties comparable to PTL (Zhang, Q.; Lu, Y.; Ding, Y.; Zhai, J.; Ji, Q.; Ma, W.; Yang, M.; Fan, H.; Long, J.; Tong, Z.; Shi, Y.; Jia, Y.; Han, B.; Zhang, W.; Qiu, C.; Ma, X.; Li, Q.; Shi, Q.; Zhang, H.; Li, D.; Zhang, J.; Lin, J.; Li, L.-Y.; Gao, Y.; Chen, Y. J. Med. Chem. 2012, 55, 8757; An, Y.; Guo, W.; Li, L.; Xu, C.; Yang, D.; Wang, S.; Lu, Y.; Zhang, Q.; Zhai, J.; Fan, H.; Qiu, C.; Qi, J.; Chen, Y.; Yuan, S. PLoS One 2015, 10, e0116202]. As previously done in the case of PTL (Guzman, Rossi et al. 2006; Hwang, Chang et al. 2006; Nasim and Crooks 2008; Han, Barrios et al. 2009; Neelakantan, Nasim et al. 2009; Woods, Mo et al. 2011), efforts toward the development of MCL derivatives with potentially improved pharmacological properties have involved the addition of dimethylamine to the reactive α-methylene-γ-lactone moiety, resulting in the C13-dimethylamino adduct of MCL (Zhang et al, J. Med. Chem. 2012, 55, 8757). Alternatively, MCL derivatives have been prepared via modification of the hydroxyl group in C4 via etherification or esterification (Ma W W et al, *Molecules* 2013, 18, 5980-5992). However, none of these modifications were found to lead to MCL analogs with improved anticancer activity.

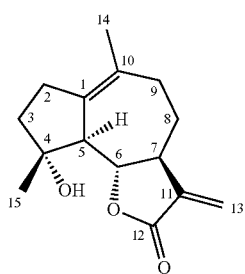

Micheliolide (1, MCL)

Thus, there is a need in the art for new Micheliolide deriviatives and active Micheliolide deriviatives for use as anticancer and anti-inflammatory agents. The present invention fulfills this unmet need.

3. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated, enlarged, exploded, or incomplete to facilitate an understanding of the invention.

FIG. 1, comprising FIG. 1A through FIG. 1C depicts P450-mediated oxyfunctionalization of MCL. FIG. 1A depicts the synthesis of oxyfunctionalized MCL derivatives via oxidation of micheliolide (1) with engineered P450 variant FL #62. Products: 2(R)-hydroxy-micheliolide (2), 14-hydroxy-micheliolide (3), 14-CHO-micheliolide (4). FIG. 1B depicts the large scale synthesis of 2(R)-hydroxy- (2) and 14-hydroxy-MCL (3) using engineered P450 variants V-F10 and V-H10. FIG. 1C depicts the large scale synthesis of 14-hydroxy-MCL (3) using engineered P450 variant V-H10.

FIG. 9 depicts the antileukemic activity of MCL and MCL derivatives as measured based on cytotoxicity (($LD_{50}$) against AML cells (M9-ENL1).

FIG. 10 depicts the antileukemic activity of MCL and MCL derivatives as measured based on cytotoxicity ($LD_{50}$) against four different primary human acute myelogenous leukemia (AML) specimens.

4. DETAILED DESCRIPTION OF THE INVENTION

Figures 1A, 1B, 1C:
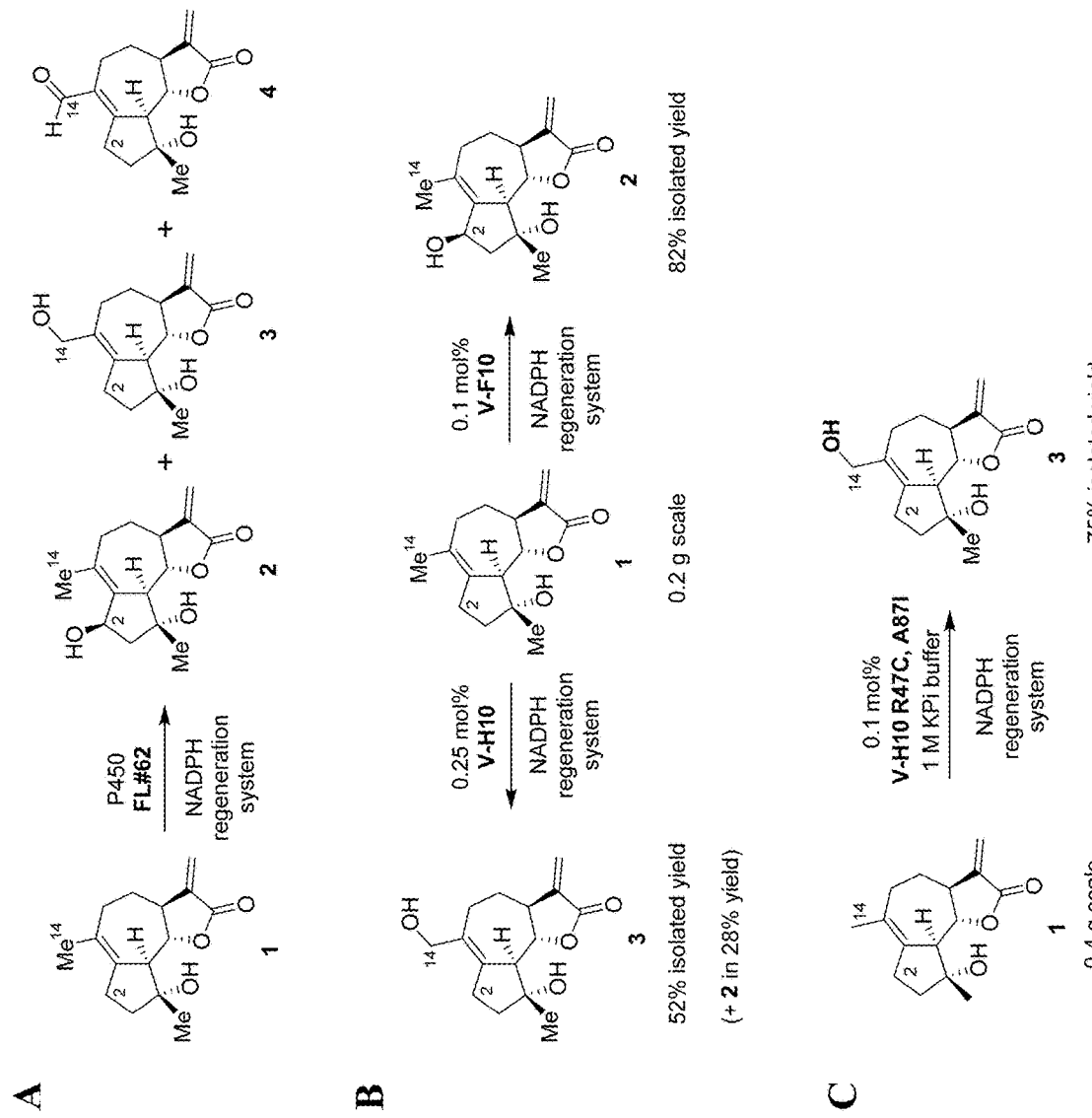

Methods are provided for the generation of novel micheliolide derivatives functionalized at carbon atoms C2 and C14. The invention is based on the discovery that engineered variants of cytochrome P450 enzymes can be used to carry out the hydroxylation of these sites in micheliolide. According to the methods disclosed herein, these P450-catalyzed C—H hydroxylation reactions can be coupled to chemical interconversion of the enzymatically introduced hydroxyl group in order to install a broad range of functionalities at these otherwise unreactive sites of the molecule. As further demonstrated herein, the methods provided herein can also be applied to enable the production of bifunctionalized micheliolide derivatives, which in addition to modifications at the level of carbon atom C2 or C14, are also functionalized at the level of carbon atom C13.

While currently available methods have permitted the preparation of C13-modified MCL derivatives, the methods provided herein enable the modification of additional positions in the MCL scaffold. These methods can be useful to functionalize the C2 and C14 positions, optionally in conjunction with functionalization at the C13 position, to generate next-generation micheliolide derivatives with unexpectedly improved pharmacological properties.

Prior to this disclosure, the utility of cytochrome P450 enzymes and engineered variants thereof, for MCL oxyfunctionalization was unknown. The inventors discovered that engineered variants of natural cytochrome P450 monooxygenase enzymes can be exploited for the purpose of hydroxylating aliphatic positions in the MCL carbocyclic backbone (i.e. position C2 and C14) with high efficiency (i.e. high turnover numbers) and, in some cases, with excellent degrees of regio- and stereoselectivity, while preserving the integrity of critical functionalities in the molecule, such as the α-methylene-γ-lactone moiety and the 4,5-epoxide group.

The synthesis of C2- or C14-functionalized derivatives of micheliolide has never been described before. The present invention provides methods to generate derivatives of this type via a two-step chemoenzymatic strategy, in which micheliolide is first hydroxylated to generate 2-hydroxy-micheliolide or 14-hydroxy-micheliolide by means of one or more P450 monooxygenase enzyme(s). These hydroxylated derivatives can be isolated (e.g., via chromatography or extraction) and then subjected to chemical reaction conditions suitable for converting the enzymatically installed hydroxyl group (—OH) into a different functional group, such as, for example, a halogen, an ether group, a thioether group, an acyloxy group, an amide group, or an amino group. Several reagents and reaction conditions are known in the art to perform the chemical interconversion of a hydroxyl group (—OH), including reagents and reaction conditions for alkylation, acylation, deoxohalogenation, and nucleophilic substitution of an hydroxyl group (—OH).

Furthermore, using the methods provided herein it is also possible to first generate 2- or 14-substituted micheliolide derivatives chemoenzymatically and then use these compounds as intermediates to synthesize doubly substituted micheliolide derivatives (i.e. C2,C13-disubstituted derivatives, C14,C13-disubstituted derivatives), in which the C13 position is also modified. Within this aspect of the invention, previously reported methods that are suitable for the functionalization of the C13 site in parthenolide (Guzman, Rossi et al. 2006; Hwang, Chang et al. 2006; Nasim and Crooks 2008; Han, Barrios et al. 2009; Neelakantan, Nasim et al. 2009; Woods, Mo et al. 2011) (See also Crooks et. al, U.S. Pat. Nos. 7,312,242; 7,678,904; 8,124,652) can be applied, as long as the reaction conditions involved in these processes are compatible with the functional group(s) contained within the substituent preinstalled in position C2 or C14.

For clarity of disclosure, and not by way of limitation, the detailed description of the invention is divided into the subsections set forth below.

4.1 Definitions

The term "functional group" as used herein refers to a contiguous group of atoms that, together, may undergo a chemical reaction under certain reaction conditions. Examples of functional groups are, among many others, —OH, —NH$_2$, —SH, —(C=O)—, —N$_3$, —C≡CH.

The term "aliphatic" or "aliphatic group" as used herein means a straight or branched C$_{1-15}$ hydrocarbon chain that is completely saturated or that contains one or more units of unsaturation, or a monocyclic C$_{3-8}$ hydrocarbon, or bicyclic C$_{8-12}$ hydrocarbon that is completely saturated or that contains one or more units of unsaturation, but which is not aromatic (also referred to herein as "cycloalkyl"). For example, suitable aliphatic groups include, but are not limited to, linear or branched alkyl, alkenyl, alkynyl groups or hybrids thereof such as (cycloalkyl)alkyl, (cycloalkenyl) alkyl, or (cycloalkynyl)alkyl. The alkyl, alkenyl, or alkynyl group may be linear, branched, or cyclic and may contain up to 15, preferably up to 8, and most preferably up to 5 carbon atoms. Preferred alkyl groups include methyl, ethyl, propyl, cyclopropyl, butyl, cyclobutyl, pentyl, and cyclopentyl groups. Preferred alkenyl groups include propenyl, butenyl, and pentenyl groups. Preferred alkynyl groups include propynyl, butynyl, and pentynyl groups.

The term "aryl" and "aryl group" as used herein refers to an aromatic substituent containing a single aromatic or multiple aromatic rings that are fused together, directly linked, or indirectly linked (such as linked through a methylene or an ethylene moiety). A aryl group may contain from 5 to 24 carbon atoms, preferably 5 to 18 carbon atoms, and most preferably 5 to 14 carbon atoms.

The terms "heteroatom" means nitrogen, oxygen, or sulphur, and includes any oxidized forms of nitrogen and sulfur, and the quaternized form of any basic nitrogen. Heteroatom further include Se, Si, and P.

The term "heteroaryl" as used herein refer to an aryl group in which at least one carbon atom is replaced with a heteroatom. Preferably, a heteroaryl group is a 5- to 18-membered, particularly a 5- to 14-membered, and especially a 5- to 10-membered aromatic ring system containing at least one heteroatom selected from the group consisting of oxygen, sulphur, and nitrogen atoms. Preferred heteroaryl groups include pyridyl, pyrrolyl, furyl, thienyl, indolyl, isoindolyl, indolizinyl, imidazolyl, pyridonyl, pyrimidyl, pyrazinyl, oxazolyl, thiazolyl, purinyl, quinolinyl, isoquinolinyl, benzofuranyl, and benzoxazolyl groups.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Preferably, a heterocyclic group is a 3- to 18-membered, particularly a 3- to 14-membered, and especially a 3- to 10-membered, ring system containing at least one heteroatom selected from the group consisting of oxygen, sulphur, and nitrogen atoms. Preferred heterocyclic groups include the specific heteroaryl groups listed above as well as pyranyl, piperidinyl, pyrrolidinyl, dioaxanyl, piperazinyl, morpholinyl, thiomorpholinyl, morpholinosulfonyl, tetrahydroisoquinolinyl, and tetrahydrofuranyl groups.

A halogen atom may be a fluorine, chlorine, bromine, or iodine atom.

By "optionally substituted", it is intended that in the any of the chemical groups listed above (e.g., alkyl, alkenyl, alkynyl, heteroalkyl, heteroalkenyl, heteroalkynyl, aryl, heteroaryl, heterocyclic, triazolyl groups), one or more hydrogen atoms are optionally replaced with an atom or chemical group other than hydrogen. Specific examples of such substituents include, without limitation, halogen atoms, hydroxyl (—OH), sulfhydryl (—SH), substituted sulfhydryl, carbonyl (—CO—), carboxy (—COOH), amino (—NH$_2$), nitro (—NO$_2$), sulfo (—SO$_2$—OH), cyano (—CN), thiocyanato (—S—C≡N), phosphono (—P(O)OH$_2$), alkyl, alkenyl, alkynyl, heteroalkyl, heteroalkenyl, heteroalkynyl, aryl, heteroaryl, heterocyclic, alkylthiol, alkyloxy, alkylamino, arylthiol, aryloxy, or arylamino groups. Where "optionally substituted" modifies a series of groups separated by commas (e.g., "optionally substituted A, B, or C"; or "A, B, or C optionally substituted with"), it is intended that each of the groups (e.g., A, B, or C) is optionally substituted.

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when a protein is 'contacted' with a chemical species, the protein is allowed to interact with the chemical species so that a reaction between the protein and the chemical species can occur.

The term "polypeptide", "protein", and "enzyme" as used herein refers to any chain of two or more amino acids bonded in sequence, regardless of length or post-translational modification. According to their common use in the art, the term "protein" refers to any polypeptide consisting of more than 50 amino acid residues. These definitions are however not intended to be limiting.

In general, the term "mutant" or "variant" as used herein with reference to a molecule such as polynucleotide or polypeptide, indicates that such molecule has been mutated from the molecule as it exists in nature. In particular, the term "mutate" and "mutation" as used herein indicates any modification of a nucleic acid and/or polypeptide which results in an altered nucleic acid or polypeptide. Mutations include any process or mechanism resulting in a mutant protein, enzyme, polynucleotide, or gene. A mutation can occur in a polynucleotide or gene sequence, by point mutations, deletions, or insertions of single or multiple nucleotide residues. A mutation in a polynucleotide includes mutations arising within a protein-encoding region of a gene as well as mutations in regions outside of a protein-encoding sequence, such as, but not limited to, regulatory or promoter sequences. A mutation in a coding polynucleotide such as a gene can be "silent", i.e., not reflected in an amino acid alteration upon expression, leading to a "sequence-conservative" variant of the gene. A mutation in a polypeptide includes but is not limited to mutation in the polypeptide sequence and mutation resulting in a modified amino acid. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like.

The term "engineer" or "engineered" refers to any manipulation of a molecule that result in a detectable change in the molecule, wherein the manipulation includes but is not limited to inserting a polynucleotide and/or polypeptide heterologous to the cell and mutating a polynucleotide and/or polypeptide native to the cell.

The term "polynucleotide molecule" as used herein refers to any chain of two or more nucleotides bonded in sequence. For example, a nucleic acid molecule can be a DNA or a RNA.

The terms "vector" and "vector construct" as used herein refer to a vehicle by which a DNA or RNA sequence (e.g., a foreign gene) can be introduced into a host cell, so as to transform the host and promote expression (e.g., transcription and translation) of the introduced sequence. A common type of vector is a "plasmid", which generally is a self-contained molecule of double-stranded DNA that can be readily accept additional (foreign) DNA and which can be readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. The terms "express" and "expression" refer to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be the to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "fused" as used herein means being connected through one or more covalent bonds. The term "bound" as used herein means being connected through non-covalent interactions. Examples of non-covalent interactions are van der Waals, hydrogen bond, electrostatic, and hydrophobic interactions. The term "tethered" as used herein means being connected through covalent or non-covalent interactions. Thus, a "polypeptide tethered to a solid support" refers to a polypeptide that is connected to a solid support (e.g., surface, resin bead) either via non-covalent interactions or through covalent bonds.

4.2 P450 Monooxygenase Enzymes

The present invention provides cytochrome P450 polypeptides having the capability to oxidize micheliolide, wherein the cytochrome P450 polypeptide comprises an amino acid sequence having at least 90% sequence identity to CYP102A1 from *Bacillus megaterium* (SEQ ID NO: 1) or to the CYP102A1 variant FL #62 (SEQ. ID NO:2).

In one embodiment, the P450 polypeptide comprises an amino acid sequence having at least 90% sequence identity to CYP102A1 from *Bacillus megaterium*. In one embodiment, the CYP102A1 from *Bacillus megaterium* comprises an amino acid sequence of:

```
                                              (SEQ ID NO: 1)
MTIKEMPQPKTFGELKNLPLLNTDKPVQALMKIADELGEIFKFEAPGRV

TRYLSSQRLIKEACDESRFDKNLSQALKFVRDFAGDGLFTSWTHEKNWK

KAHNILLPSFSQQAMKGYHAMMVDIAVQLVQKWERLNADEHIEVPEDMT

RLTLDTIGLCGFNYRFNSFYRDQPHPFITSMVRALDEAMNKLQRANPDD

PAYDENKRQFQEDIKVMNDLVDKIIADRKASGEQSDDLLTHMLNGKDPE

TGEPLDDENIRYQIITFLIAGHETTSGLLSFALYFLVKNPHVLQKAAEE

AARVLVDPVPSYKQVKQLKYVGMVLNEALRLWPTAPAFSLYAKEDTVLG

GEYPLEKGDELMVLIPQLHRDKTIWGDDVEEFRPERFENPSAIPQHAFK

PFGNGQRACIGQQFALHEATLVLGMMLKHFDFEDHTNYELDIKETLTLK

PEGFVVKAKSKKIPLGGIPSPSTEQSAKKVRKKAENAHNTPLLVLYGSN

MGTAEGTARDLADIAMSKGFAPQVATLDSHAGNLPREGAVLIVTASYNG

HPPDNAKQFVDWLDQASADEVKGVRYSVFGCGDKNWATTYQKVPAFIDE

TLAAKGAENIADRGEADASDDFEGTYEEWREHMWSDVAAYFNLDIENSE

DNKSTLSLQFVDSAADMPLAKMHGAFSTNVVASKELQQPGSARSTRHLE

IELPKEASYQEGDHLGVIPRNYEGIVNRVTARFGLDASQQIRLEAEEEK

LAHLPLAKTVSVEELLQYVELQDPVTRTQLRAMAAKTVCPPHKVELEAL

LEKQAYKEQVLAKRLTMLELLEKYPACEMKFSEFIALLPSIRPRYYSIS

SSPRVDEKQASITVSVVSGEAWSGYGEYKGIASNYLAELQEGDTITCFI

STPQSEFTLPKDPETPLIMVGPGTGVAPFRGFVQARKQLKEQGQSLGEA

HLYFGCRSPHEDYLYQEELENAQSEGIITLHTAFSRMPNQPKTYVQHVM

EQDGKKLIELLDQGAHFYICGDSQMAPAVEATLMKSYADVHQVSEADA

RLWLQQLEEKGRYAKDVWAG
```

In one embodiment, the P450 polypeptide comprises an amino acid sequence having at least 90% sequence identity to CYP102A1 variant FL #62 from *Bacillus megaterium*. In one embodiment, the CYP102A1 variant FL #62 from *Bacillus megaterium* comprises an amino acid sequence of:

```
                                              (SEQ ID NO: 2)
MTIKEMPQPKTFGELKNLPLLNTDKPVQALMKIADELGEIFKFEAPGRV

TRYLSSQRLIKEACDESRFDKNLSQALKFARDSVGDGLATSWTHEKNWK

KAHNILLPSFSQQAMKGYHAMMVDIAVQLVQKWERLNADEHIEVSEDMT

RLTLDTIGLCGFNYRFNSFYRDQPHPFIISMVRTLDEVMNKLQRANPDD

PVYDENKRQCQEDIKVMNDLVDKIIADRKARGEQSDDLLTQMLNGKDPE

TGEPLDDGNISYQIITFLIAGHETTSGLLSFALYFLVKNPHVLQKVAEE

AARVLVDPVPSYKQVKQLKYVGMVLNEALRLWPTAPAFSLYAKEDTVLG

GEYPLEKGDEVMVLIPQLHRDKTIWGDDVEEFRPERFENPSAIPQHAFK

PFGNGQRACIGQQFALHEATLVLGMMLKHFDFEDHTNYELDIKETLTLK

PEGFVVKAKSKKIPLGGIPSPSTEQSAKKVRKKAENAHNTPLLVLYGSN

MGTAEGTARDLADIAMSKGFAPQVATLDSHAGNLPREGAVLIVTASYNG

HPPDNAKQFVDWLDQASADEVKGVRYSVFGCGDKNWATTYQKVPAFIDE

TLAAKGAENIADRGEADASDDFEGTYEEWREHMWSDVAAYFNLDIENSE

DNKSTLSLQFVDSAADMPLAKMHGAFSTNVVASKELQQPGSARSTRHLE

IELPKEASYQEGDHLGVIPRNYEGIVNRVTARFGLDASQQIRLEAEEEK

LAHLPLAKTVSVEELLQYVELQDPVTRTQLRAMAAKTVCPPHKVELEAL

LEKQAYKEQVLAKRLTMLELLEKYPACEMKFSEFIALLPSIRPRYYSIS

SSPRVDEKQASITVSVVSGEAWSGYGEYKGIASNYLAELQEGDTITCFI

STPQSEFTLPKDPETPLIMVGPGTGVAPFRGFVQARKQLKEQGQSLGEA

HLYFGCRSPHEDYLYQEELENAQSEGIITLHTAFSRMPNQPKTYVQHVM

EQDGKKLIELLDQGAHFYICGDSQMAPAVEATLMKSYADVHQVSEADA

RLWLQQLEEKGRYAKDVWAG.
```

In one embodiment, the P450 polypeptide comprises an amino acid sequence having at least 90% sequence identity to CYP102A1 variant FL #46 from *Bacillus megaterium*. In one embodiment, the CYP102A1 variant FL #46 from *Bacillus megaterium* comprises an amino acid sequence of:

```
                                              (SEQ ID NO: 3)
MTIKEMPQPKTFGELKNLPLLNTDKPVQALMKIADELGEIFKFEAPGCV

TRYLSSQRLIKEACDESRFDKNLSQALKAVRDFAGDGLITSWTHEINWK

KAHNILLPSFSQQAMKGYHAMMVDIAVQLVQKWERLNADEHIEVSEDMT

RLTLDTIGLCGFNYRFNSFYRDQPHPFIISMVRALDEVMNKLQRANPDD

PAYDENKRQCQEDIKVMNDLVDKIIADRKARGEQSDDLLTQMLNGKDPE

TGEPLDDGNISYQIITFLIAGHETTSGLLSFALYFLVKNPHVLQKVAEE

AARVLVDPVPSYKQVKQLKYVGMVLNEALRLWPTAPAFSLYAKEDTVLG

GEYPLEKGDEVMVLIPQLHRDKTIWGDDVEEFRPERFENPSAIPQHAFK

PFGNGQRACIGQQFALHEATLVLGMMLKHFDFEDHTNYELDIKETLTLK

PEGFVVKAKSKKIPLGGIPSPSTEQSAKKVRKKAENAHNTPLLVLYGSN

MGTAEGTARDLADIAMSKGFAPQVATLDSHAGNLPREGAVLIVTASYNG

HPPDNAKQFVDWLDQASADEVKGVRYSVFGCGDKNWATTYQKVPAFIDE

TLAAKGAENIADRGEADASDDFEGTYEEWREHMWSDVAAYFNLDIENSE

DNKSTLSLQFVDSAADMPLAKMHGAFSTNVVASKELQQPGSARSTRHLE

IELPKEASYQEGDHLGVIPRNYEGIVNRVTARFGLDASQQIRLEAEEEK

LAHLPLAKTVSVEELLQYVELQDPVTRTQLRAMAAKTVCPPHKVELEAL

LEKQAYKEQVLAKRLTMLELLEKYPACEMKFSEFIALLPSIRPRYYSIS

SSPRVDEKQASITVSVVSGEAWSGYGEYKGIASNYLAELQEGDTITCFI

STPQSEFTLPKDPETPLIMVGPGTGVAPFRGFVQARKQLKEQGQSLGEA
```

HLYFGCRSPHEDYLYQEELENAQSEGIITLHTAFSRMPNQPKTYVQHVM

EQDGKKLIELLDQGAHFYICGDGSQMAPAVEATLMKSYADVHQVSEADA

RLWLQQLEEKGRYAKDVWAG.

In one embodiment, the P450 polypeptide comprises an amino acid sequence having at least 90% sequence identity to CYP102A1 variant FL #47 from *Bacillus megaterium*. In one embodiment, the CYP102A1 variant FL #47 from *Bacillus megaterium* comprises an amino acid sequence of:

(SEQ ID NO: 4)
MTIKEMPQPKTFGELKNLPLLNTDKPVQALMKIADELGEIFKFEAPGCV

TRYLSSQRLIKEACDESRFDKNLSQALKAVRDFAGDGLATSWTHEINWK

KAHNILLPSFSQQAMKGYHAMMVDIAVQLVQKWERLNADEHIEVSEDMT

RLTLDTIGLCGFNYRFNSFYRDQPHPFIISMVRALDEVMNKLQRANPDD

PAYDENKRQCQEDIKVMNDLVDKIIADRKARGEQSDDLLTQMLNGKDPE

TGEPLDDGNISYQIITFLIAGHETTSGLLSFALYFLVKNPHVLQKVAEE

AARVLVDPVPSYKQVKQLKYVGMVLNEALRLWPTAPAFSLYAKEDTVLG

GEYPLEKGDEVMVLIPQLHRDKTIWGDDVEEFRPERFENPSAIPQHAFK

PFGNGQRACIGQQFALHEATLVLGMMLKHFDFEDHTNYELDIKETLTLK

PEGFVVKAKSKKIPLGGIPSPSTEQSAKKVRKKAENAHNTPLLVLYGSN

MGTAEGTARDLADIAMSKGFAPQVATLDSHAGNLPREGAVLIVTASYNG

HPPDNAKQFVDWLDQASADEVKGVRYSVFGCGDKNWATTYQKVPAFIDE

TLAAKGAENIADRGEADASDDFEGTYEEWREHMWSDVAAYFNLDIENSE

DNKSTLSLQFVDSAADMPLAKMHGAFSTNVVASKELQQPGSARSTRHLE

IELPKEASYQEGDHLGVIPRNYEGIVNRVTARFGLDASQQIRLEAEEEK

LAHLPLAKTVSVEELLQYVELQDPVTRTQLRAMAAKTVCPPHKVELEAL

LEKQAYKEQVLAKRLTMLELLEKYPACEMKFSEFIALLPSIRPRYYSIS

SSPRVDEKQASITVSVVSGEAWSGYGEYKGIASNYLAELQEGDTITCFI

STPQSEFTLPKDPETPLIMVGPGTGVAPFRGFVQARKQLKEQGQSLGEA

HLYFGCRSPHEDYLYQEELENAQSEGIITLHTAFSRMPNQPKTYVQHVM

EQDGKKLIELLDQGAHFYICGDGSQMAPAVEATLMKSYADVHQVSEADA

RLWLQQLEEKGRYAKDVWAG.

In one embodiment, the P450 polypeptide comprises an amino acid sequence having at least 90% sequence identity to CYP102A1 variant V-F10 from *Bacillus megaterium*. In one embodiment, the CYP102A1 variant V-F10 from *Bacillus megaterium* comprises an amino acid sequence of:

(SEQ ID NO: 5)
MTIKEMPQPKTFGELKNLPLLNTDKPVQALMKIADELGEIFKFEAPGRV

TRYLSSQRLIKEACDESRFDKNLSQALKFARAAVGDGLATSWTHEKNWK

KAHNILLPSFSQQAMKGYHAMMVDIAVQLVQKWERLNADEHIEVSEDMT

RLTLDTIGLCGFNYRFNSFYRDQPHPFIISMVRTLDEVMNKLQRANPDD

PVYDENKRQCQEDIKVMNDLVDKIIADRKARGEQSDDLLTQMLNGKDPE

TGEPLDDGNISYQIITFLIAGHETTSGLLSFALYFLVKNPHVLQKVAEE

AARVLVDPVPSYKQVKQLKYVGMVLNEALRLWPTAPAFSLYAKEDTVLG

GEYPLEKGDEVMVLIPQLHRDKTIWGDDVEEFRPERFENPSAIPQHAFK

PFGNGQRACIGQQFALHEATLVLGMMLKHFDFEDHTNYELDIKETLTLK

PEGFVVKAKSKKIPLGGIPSPSTEQSAKKVRKKAENAHNTPLLVLYGSN

MGTAEGTARDLADIAMSKGFAPQVATLDSHAGNLPREGAVLIVTASYNG

HPPDNAKQFVDWLDQASADEVKGVRYSVFGCGDKNWATTYQKVPAFIDE

TLAAKGAENIADRGEADASDDFEGTYEEWREHMWSDVAAYFNLDIENSE

DNKSTLSLQFVDSAADMPLAKMHGAFSTNVVASKELQQPGSARSTRHLE

IELPKEASYQEGDHLGVIPRNYEGIVNRVTARFGLDASQQIRLEAEEEK

LAHLPLAKTVSVEELLQYVELQDPVTRTQLRAMAAKTVCPPHKVELEAL

LEKQAYKEQVLAKRLTMLELLEKYPACEMKFSEFIALLPSIRPRYYSIS

SSPRVDEKQASITVSVVSGEAWSGYGEYKGIASNYLAELQEGDTITCFI

STPQSEFTLPKDPETPLIMVGPGTGVAPFRGFVQARKQLKEQGQSLGEA

HLYFGCRSPHEDYLYQEELENAQSEGIITLHTAFSRMPNQPKTYVQHVM

EQDGKKLIELLDQGAHFYICGDGSQMAPAVEATLMKSYADVHQVSEADA

RLWLQQLEEKGRYAKDVWAG

In one embodiment, the P450 polypeptide comprises an amino acid sequence having at least 90% sequence identity to CYP102A1 variant V-H10 from *Bacillus megaterium*. In one embodiment, the CYP102A1 variant V-H10 from *Bacillus megaterium* comprises an amino acid sequence of:

(SEQ ID NO: 6)
MTIKEMPQPKTFGELKNLPLLNTDKPVQALMKIADELGEIFKFEAPGRV

TRYLSSQRLIKEACDESRFDKNLSQALKNARFAVGDGLATSWTHEKNWK

KAHNILLPSFSQQAMKGYHAMMVDIAVQLVQKWERLNADEHIEVSEDMT

RLTLDTIGLCGFNYRFNSFYRDQPHPFIISMVRTLDEVMNKLQRANPDD

PVYDENKRQCQEDIKVMNDLVDKIIADRKARGEQSDDLLTQMLNGKDPE

TGEPLDDGNISYQIITFLIAGHETTSGLLSFALYFLVKNPHVLQKVAEE

AARVLVDPVPSYKQVKQLKYVGMVLNEALRLWPTAPAFSLYAKEDTVLG

GEYPLEKGDEVMVLIPQLHRDKTIWGDDVEEFRPERFENPSAIPQHAFK

PFGNGQRACIGQQFALHEATLVLGMMLKHFDFEDHTNYELDIKETLTLK

PEGFVVKAKSKKIPLGGIPSPSTEQSAKKVRKKAENAHNTPLLVLYGSN

MGTAEGTARDLADIAMSKGFAPQVATLDSHAGNLPREGAVLIVTASYNG

HPPDNAKQFVDWLDQASADEVKGVRYSVFGCGDKNWATTYQKVPAFIDE

TLAAKGAENIADRGEADASDDFEGTYEEWREHMWSDVAAYFNLDIENSE

DNKSTLSLQFVDSAADMPLAKMHGAFSTNVVASKELQQPGSARSTRHLE

IELPKEASYQEGDHLGVIPRNYEGIVNRVTARFGLDASQQIRLEAEEEK

LAHLPLAKTVSVEELLQYVELQDPVTRTQLRAMAAKTVCPPHKVELEAL

LEKQAYKEQVLAKRLTMLELLEKYPACEMKFSEFIALLPSIRPRYYSIS

SSPRVDEKQASITVSVVSGEAWSGYGEYKGIASNYLAELQEGDTITCFI

STPQSEFTLPKDPETPLIMVGPGTGVAPFRGFVQARKQLKEQGQSLGEA

-continued

HLYFGCRSPHEDYLYQEELENAQSEGIITLHTAFSRMPNQPKTYVQHVM

EQDGKKLIELLDQGAHFYICGDGSQMAPAVEATLMKSYADVHQVSEADA

RLWLQQLEEKGRYAKDVWAG

In one embodiment, the P450 polypeptide comprises an amino acid sequence having at least 90% sequence identity to CYP102A1 variant VIII-B1 from *Bacillus megaterium*. In one embodiment, the CYP102A1 variant VIII-B1 from *Bacillus megaterium* comprises an amino acid sequence of:

(SEQ ID NO: 7)
MTIKEMPQPKTFGELKNLPLLNTDKPVQALMKIADELGEIFKFEAPGRV

TRYLSSQRLIKEACDESRFDKNLSTALKNARFSVGDGFATSWTHEKNWK

KAHNILLPSFSQQAMKGYHAMMVDIAVQLVQKWERLNADEHIEVSEDMT

RLTLDTIGLCGFNYRFNSFYRDQPHPFIISMVATLDEVMNKLQRANPDD

PVYDENKRQCQEDIKVMNDLVDKIIADRKARGEQSDDLLTQMLNGKDPE

TGEPLDDGNISYQIITFLIAGHETTSGLLSFALYFLVKNPHVLQKVAEE

AARVLVDPVPSYKQVKQLKYVGMVLNEALRLWPTAPAFSLYAKEDTVLG

GEYPLEKGDEVMVLIPQLHRDKTIWGDDVEEFRPERFENPSAIPQHAFK

PFGNGQRACIGQQFALHEATLVLGMMLKHFDFEDHTNYELDIKETLTLK

PEGFVVKAKSKKIPLGGIPSPSTEQSAKKVRKKAENAHNTPLLVLYGSN

MGTAEGTARDLADIAMSKGFAPQVATLDSHAGNLPREGAVLIVTASYNG

HPPDNAKQFVDWLDQASADEVKGVRYSVFGCGDKNWATTYQKVPAFIDE

TLAAKGAENIADRGEADASDDFEGTYEEWREHMWSDVAAYFNLDIENSE

DNKSTLSLQFVDSAADMPLAKMHGAFSTNVVASKELQQPGSARSTRHLE

IELPKEASYQEGDHLGVIPRNYEGIVNRVTARFGLDASQQIRLEAEEEK

LAHLPLAKTVSVEELLQYVELQDPVTRTQLRAMAAKTVCPPHKVELEAL

LEKQAYKEQVLAKRLTMLELLEKYPACEMKFSEFIALLPSIRPRYYSIS

SSPRVDEKQASITVSVVSGEAWSGYGEYKGIASNYLAELQEGDTITCFI

STPQSEFTLPKDPETPLIMVGPGTGVAPFRGFVQARKQLKEQGQSLGEA

HLYFGCRSPHEDYLYQEELENAQSEGIITLHTAFSRMPNQPKTYVQHVM

EQDGKKLIELLDQGAHFYICGDGSQMAPAVEATLMKSYADVHQVSEADA

RLWLQQLEEKGRYAKDVWAG

In some embodiments, the capability to oxidize micheliolide corresponds to the capability of the cytochrome P450 polypeptide to hydroxylate a C—H bond attached to the carbon atom C2 in micheliolide, where the resulting hydroxylated product has predominantly (S) or (R) stereochemistry at the hydroxylation site (C2) according to the stereoselectivity of the enzyme. In other embodiments, such capability corresponds to the capability of the cytochrome P450 polypeptide to hydroxylate a C—H bond attached to the carbon atom C14 in micheliolide.

Cytochrome P450 polypeptides are provided that are capable of hydroxylating a C—H bond at position 2, position 14, or both, in micheliolide, and which have an improved property compared with a reference enzyme, such as the naturally occurring enzymes from which they were derived, the naturally occurring enzymes being CYP102A1 from *Bacillus megaterium* (SEQ ID NO: 1).

In the characterization of the cytochrome P450 enzymes disclosed herein, the polypeptides can be described in reference to the amino acid sequence of a naturally occurring cytochrome P450 enzyme or another engineered cytochrome P450 enzyme. As such, the amino acid residue is determined in the cytochrome P450 enzymes beginning from the initiating methionine (M) residue (i.e., M represent residue position 1), although it will be understood that this initiating methionine residue may be removed by biological processing machinery such as in a host cell or in vitro translation system, to generate a mature protein lacking the initiating methionine residue. The amino acid residue position at which a particular amino acid or amino acid change is present is sometimes described herein as "Xn", or "position n", where n refers to the residue position.

As described above, the cytochrome P450 enzymes provided herein are characterized by an improved enzyme property as compared to the naturally occurring parent enzyme or another engineered cytochrome P450 enzyme. Changes to enzyme properties can include, among others, improvements in enzymatic activity, regioselectivity, stereoselectivity, and/or reduced substrate or product inhibition. In one embodiment, the altered properties are based on engineered cytochrome P450 polypeptides having residue differences at specific residue positions as compared to a reference sequence of a naturally occurring cytochrome P450 enzyme, such as CYP102A1 (SEQ ID NO: 1).

In some embodiments, the P450 monooxygenase is an engineered variant of CYP102A1 (SEQ ID NO: 1). In one embodiment, the variant of SEQ ID NO:1 comprises an amino acid change at one or more of the following positions of SEQ ID NO: 1: X26, X27, X43, X48, X52, X53, X73, X75, X76, X79, X82, X83, X88, X89, X95, X97, X143, X146, X176, X181, X182, X185, X189, X198, X206, X226, X227, X237, X253, X256, X261, X264, X265, X268, X269, X291, X320, X331, X329, X330, X354, X355, X367, X394, X435, X436, X444, X446, X438, and X439.

In some embodiments, the cytochrome P450 polypeptides can have additionally one or more residue differences at residue positions not specified by an X above as compared to the sequence SEQ ID NO: 1 or SEQ ID NO: 2. In some embodiments, the differences can be 1-2, 1-5, 1-10, 1-20, 1-30, 1-40, 1-50, 1-75, 1-100, 1-150, or 1-200 residue differences at other amino acid residue positions not defined by X above.

In some embodiments, the cytochrome P450 polypeptides can have additionally one or more residue differences at residue positions not specified by an X above and located within the "heme domain" of the enzyme, as compared to the sequence SEQ ID NO: 1 or SEQ ID NO: 2. In some embodiments, the differences can be 1-2, 1-5, 1-10, 1-20, 1-30, 1-40, 1-50, 1-75, 1-100, 1-150, or 1-200 residue differences at other amino acid residue positions not defined by X above and located within the "heme domain" of the enzyme.

In some embodiments, the engineered cytochrome P450 polypeptides having one or more of the improved enzyme properties described herein, can comprise an amino acid sequence that is at least 60%, 70%, 80%, 85%, 90%, 95%, 99% or more identical to the sequence SEQ ID NO: 1 or SEQ ID NO: 2.

In some embodiments, the engineered cytochrome P450 polypeptides having one or more of the improved enzyme properties described herein, can comprise an amino acid sequence encompassing its heme domain which is at least 60%, 70%, 80%, 85%, 90%, 95%, 99% or more identical to the amino acid sequence encompassing the first 500 amino acids in the sequence SEQ ID NO: 1 or SEQ ID NO: 2 (i.e. residue 1 to residue 500 in these reference sequences).

In some embodiments, the improved cytochrome P450 polypeptide can comprise an amino acid sequence that is at least 90% or more identical to a sequence corresponding to one of SEQ ID NOS: 2, 3, 4, 5, 6, and 7.

In some embodiments, the improved cytochrome P450 polypeptide can comprise an amino acid sequence encompassing its heme domain that is at least 90% or more identical to the sequence encompassing the first 500 amino acids in one of SEQ ID NOS: 2, 3, 4, 5, 6, and 7.

In some embodiments, the improved cytochrome P450 polypeptide comprises an amino acid sequence corresponding to the sequence of one of SEQ ID NOS: 2, 3, 4, 5, 6, and 7.

The capability of the engineered cytochrome P450 polypeptides to oxidize micheliolide, also referred to herein as "substrate," can be established according to methods well known in the art. Most typically, such capability can be established by contacting the substrate with the P450 monooxygenase under suitable reaction conditions in which the P450 monooxygenase is catalytically functional, and then determining the formation of an oxidized product of the substrate (e.g., hydroxylated product) by standard analytical methods such as, for example, thin-layer chromatography, HPLC, and/or LC-MS.

Various art-known methods can be applied for measuring the catalytic activity of the engineered cytochrome P450 polypeptide on parthenolide, also referred to herein as "substrate activity". Such substrate activity can be measured by measuring the decrease of the amount of substrate, the accumulation of an oxygenation product derived from the substrate (e.g., hydroxylated product), or the accumulation of an oxidation byproduct generated during the enzymatic reaction (e.g., $H_2O_2$), after a given time after contacting the substrate with the P450 monooxygenase under suitable reaction conditions in which the P450 monooxygenase is catalytically functional. Other methods to measure the substrate activity include measuring the consumption of a cofactor (e.g., NADPH or NADH) or cosubstrate ($O_2$) utilized by the enzyme during the oxidation reaction. The choice of the method will vary depending on the specific application such as, for example, according to the nature of the substrate, the nature of the monooxygenase (e.g., its NAD(P)H cofactor specificity), and the number of the P450 monooxygenases that are to be evaluated. A person skilled in the art will be capable of selecting the most appropriate method in each case.

The substrate activity of engineered cytochrome P450 polypeptides can be measured and expressed in terms of number of catalytic turnovers, product formation rate, cofactor consumption rate, $O_2$ consumption rate, $H_2O_2$ consumption rate (e.g., for $H_2O_2$-dependent monooxygenases), and the like. Most conveniently, such substrate activity can be measured and expressed in terms of total turnover numbers (or TTN), which corresponds to the total number of catalytic turnovers supported by the P450 monooxygenase enzyme on this substrate.

In some embodiments, the engineered cytochrome P450 polypeptides disclosed herein are capable of supporting at least 1, 10, 50, 100, or more TTN in the oxidation of micheliolide.

The regio- and stereoselectivity of the engineered cytochrome P450 polypeptides for the oxidation of micheliolide can be measured by determining the relative distribution of oxidation products generated by the reaction between the substrate and the cytochrome P450 polypeptide using conventional analytical methods such as, for example, (chiral) normal phase liquid chromatography, (chiral) reverse-phase liquid chromatography, or (chiral) gas chromatography. In some instances, the oxidation products can be subjected to a chemical derivatization process to facilitate these analyses. For example, the hydroxylation products obtained from the reaction of the P450 polypeptide with micheliolide can be derivatized using an UV-active acid chloride (e.g., benzoyl chloride) prior to separation and quantification by HPLC.

In some embodiments, the engineered cytochrome P450 polypeptides disclosed herein are capable of hydroxylating a C—H bond connected to the C2 or C14 carbon atom in micheliolide with a regioselectivity of 1%, 5%, 10%, 25%, 50%, 75%, 90%, 95%, or higher.

In some embodiments, the polypeptide described herein can be provided in form of a kit. These kits may contain an individual enzyme or a plurality of enzymes. The kits can further include reagents for carrying out the enzymatic reactions, substrates for assessing the activity of the enzymes, and reagents for detecting the products. The kits can also include instructions for the use of the kits.

In some embodiments, the polypeptides described herein can be covalently or non-covalently linked to a solid support for the purpose, for example, of screening the enzymes for activity on a range of different substrates or for facilitating the separation of reactants and products from the enzyme after the enzymatic reactions. Examples of solid supports include but are not limited to, organic polymers such as polystyrene, polyacrylamide, polyethylene, polypropylene, polyethyleneglycole, and the like, and inorganic materials such as glass, silica, controlled pore glass, metals. The configuration of the solid support can be in the form of beads, spheres, particles, gel, a membrane, or a surface.

4.3 Polynucleotides and Host Cells for Expression of P450 Monooxygenase Enzymes In another aspect, the present invention provides polynucleotide molecules encoding for the improved cytochrome P450 polypeptides disclosed herein. The polynucleotides may be linked to one or more regulatory sequences controlling the expression of the cytochrome P450 polypeptide-encoding gene to form a recombinant polynucleotide capable of expressing the polypeptide.

Since the correspondence of all the possible three-base codons to the various amino acids is known, providing the amino acid sequence of the P450 polypeptide provides also a description of all the polynucleotide molecules encoding for such polypeptide. Thus, a person skilled in the art will be able, given a certain polypeptide sequence, to generate any number of different polynucleotides encoding for the same polypeptide. Preferably, the codons are selected to fit the host cell in which the polypeptide is being expressed. For example, preferred codons used in bacteria are preferably used to express the polypeptide in a bacterial host.

In some embodiments, the polynucleotide molecule comprises a nucleotide sequence encoding for a cytochrome P450 polypeptide with an amino acid sequence that is at least 60%, 70%, 80%, 85%, 90%, 95%, 99% or more identical to SEQ ID NO: 1, 2, 3, 4 5, 6 or 7.

In some embodiments, the polynucleotide molecule encoding for the improved cytochrome P450 polypeptide is comprised in a recombinant expression vector. Examples of suitable recombinant expression vectors include but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used. A large number of expression vectors and expression hosts are known in the art, and many of these are commercially available. A person skilled in the art will be able to select suitable expression vectors for a particular application, e.g., the type of expression host (e.g., in vitro systems, prokaryotic cells such as bacterial cells, and eukaryotic cells such as yeast, insect, or mammalian cells) and the expression conditions selected.

In another aspect, the present invention provides an expression host system comprising a polynucleotide molecule encoding for the improved cytochrome P450 polypeptides disclosed herein. Expression host systems that may be used within the invention include any systems that support the transcription, translation, and/or replication of a polynucleotide molecule provided herein. Preferably, the expression host system is a cell. Host cells for use in expressing the polypeptides encoded by the expression vector disclosed herein are well known in the art and include but are not limited to, bacterial cells (e.g., *Escherichia coli, Streptomyces*); fungal cells such as yeast cells (e.g., *Saccharomyces cerevisiae, Pichia pastoris*); insect cells; plant cells; and animal cells. The expression host systems also include lysates of prokaryotic cells (e.g., bacterial cells) and lysates of eukaryotic cells (e.g., yeast, insect, or mammalian cells). These systems also include in vitro transcription/translation systems, many of which are commercially available. The choice of the expression vector and host system depends on the type of application intended for the methods provided herein and a person skilled in the art will be able to select a suitable expression host based on known features and application of the different expression hosts.

4.4 Methods of Preparing and Using the Engineered Cytochrome P450 Polypeptides The engineered cytochrome P450 polypeptides can be prepared via mutagenesis of the polynucleotide encoding for the naturally occurring cytochrome P450 enzymes (SEQ ID NO: 1, 2, or 3) or for an engineered variant thereof. Many mutagenesis methods are known in the art and these include, but are not limited to, site-directed mutagenesis, site-saturation mutagenesis, random mutagenesis, cassette-mutagenesis, DNA shuffling, homologous recombination, non-homologous recombination, site-directed recombination, and the like. Detailed description of art-known mutagenesis methods can be found, among other sources, in U.S. Pat. Nos. 5,605,793; 5,830,721; 5,834,252; WO 95/22625; WO 96/33207; WO 97/20078; WO 97/35966; WO 98/27230; WO 98/42832; WO 99/29902; WO 98/41653; WO 98/41622; WO 98/42727; WO 00/18906; WO 00/04190; WO 00/42561; WO 00/42560; WO 01/23401; WO 01/64864.

Numerous methods for making nucleic acids encoding for polypeptides having a predetermined or randomized sequence are known to those skilled in the art. For example, oligonucleotide primers having a predetermined or randomized sequence can be prepared chemically by solid phase synthesis using commercially available equipments and reagents. Polynucleotide molecules can then be synthesized and amplified using a polymerase chain reaction, digested via endonucleases, ligated together, and cloned into a vector according to standard molecular biology protocols known in the art (e.g., Sambrook et al. Molecular Cloning: A Laboratory Manual (Third Edition), Cold Spring Harbor Press, 2001). These methods, in combination with the mutagenesis methods mentioned above, can be used to generate polynucleotide molecules that encode for engineered cytochrome P450 polypeptides as well as suitable vectors for the expression of these polypeptides in a host expression system.

Engineered cytochrome P450 polypeptides expressed in a host expression system, such as, for example, in a host cell, can be isolated and purified using any one or more of the well-known techniques for protein purification, including, among others, cell lysis via sonication or chemical treatment, filtration, salting-out, and chromatography (e.g., ion-exchange chromatography, gel-filtration chromatography, etc.).

The recombinant P450 polypeptides obtained from mutagenesis of a parental P450 enzyme sequences (e.g., one of SEQ ID NO: 1-7 or engineered variants thereof) can be screened for identifying engineered P450 polypeptides having improved enzyme properties, such as improvements with respect to their catalytic activity, coupling efficiency, regioselectivity and/or stereoselectivity for the oxidation of parthenolide. The improvement resulting from the introduced amino acid mutation(s) in any one or more of these enzyme properties can be then measured according to methods known in the art, as described above.

In some embodiments, a method is provided for oxidizing micheliolide, the method comprising a. contacting micheliolide with an engineered cytochrome P450 polypeptide;

b. allowing for the engineered cytochrome P450 enzyme to catalyze the hydroxylation of a C—H bond within micheliolide, while preserving α-methylene-γ-lactone moiety therein, thereby producing a hydroxylated micheliolide derivative;

c. isolating the hydroxylated micheliolide derivative.

In some embodiments, the C—H bond hydroxylated by the engineered cytochrome P450 polypeptide within the method is attached to carbon C14 in micheliolide.

In some embodiments, the C—H bond hydroxylated by the engineered cytochrome P450 polypeptide within the method is attached to carbon C2 in micheliolide. In this case, and in some embodiment, either the 2(S)- or the 2(R)-hydroxy product is produced in stereomeric excess.

In some embodiments, the engineered cytochrome P450 polypeptide used in the method comprises an amino acid sequence that is at least 60%, 70%, 80%, 85%, 90%, 95%, 99% or more identical to the sequence of one of SEQ ID NO: 1-7.

In some embodiments, the amino acid sequence encompassing the heme domain of the engineered cytochrome P450 polypeptide used in the method comprises has an amino acid sequence that is at least 60%, 70%, 80%, 85%, 90%, 95%, 99% or more identical to the amino acid sequence encompassing the first 500 amino acids in the sequences of one of SEQ ID NO: 1-7 (i.e. residue 1 to residue 500 in these sequences).

As it is known in the art, P450-catalyzed reactions typically require a source of oxygen (as co-substrate) as well as a source of reducing equivalents (i.e., electrons) to drive catalysis. Most typically, and in preferred embodiments, oxygen is provided in the form of molecular oxygen. The source of reducing equivalents can be provided in the form of a soluble cofactor, and in most preferred embodiments, it is provided in the form of reduced nicotinamide adenine dinucleotide phosphate (NADPH), which is the cofactor utilized by the cytochrome P450 enzymes disclosed herein, namely the polypeptides with one of SEQ ID NO: 1-7, and engineered variants thereof, as described above.

Alternative sources of reducing equivalents include but are not limited to, reduced nicotinamide adenine dinucleotide (NADH) or an electrode. Alternatively, chemical compounds that can serve as source of both oxygen and electrons such as for example, hydrogen peroxide ($H_2O_2$) or organic peroxides may also be used.

In some embodiments, the P450 reactions are carried out in the presence of a NADPH cofactor regeneration system or a NADH cofactor regeneration system. Suitable NADPH regeneration systems include but are not limited to, those based on glucoses-6-phosphate dehydrogenase or on $NADP^+$-utilizing phosphite dehydrogenase variants. (van der Donk and Zhao 2003; Zhao and van der Donk 2003) Suitable NADH regeneration systems include but are not limited to, those based on glucose dehydrogenase, phosphite dehydrogenase, or formate dehydrogenase (van der Donk and Zhao 2003; Zhao and van der Donk 2003).

Typically, the P450 reactions are carried out in a buffered aqueous solution. Various buffering agents such as phosphate, acetate, TRIS, MOPS, HEPES, etc. can be used. An organic cosolvent such as, for example, methanol, ethanol, dimethylsulfoxide, dimethylformamide, etc. can be added, provided these cosolvent and their relative concentration in the cosolvent system does not completely inactivate the P450 enzyme.

In carrying out the P450 reactions described herein, the engineered P450 enzymes may be added to the reaction mixture in the form of purified enzymes, whole cells containing the P450 enzymes, and/or cell extracts and/or lysates of such cells.

Typically, the P450 reactions are allowed to proceed until a substantial amount of the substrate is transformed into the product. Product formation (or substrate consumption) can be monitored using standard analytical methods such as, for example, thin-layer chromatography, GC, HPLC, or LC-MS. Experimental parameters such as amount of P450 enzyme added to the reaction mixture, temperature, solvent composition, cofactor concentration, composition of the cofactor regeneration system, etc. can be readily optimized by routine experimentation and a person skilled in the art will be able to identify most suitable reaction conditions according to the substrate and the P450 enzyme utilized in the process.

4.5 Micheliolide Derivatives

The engineered P450 polypeptides provided herein provide a means for introducing a hydroxyl group (—OH) in aliphatic positions of the carbocyclic backbone of micheliolide, such as position C2 or position C14, whose chemical functionalization have never been accomplished before. According to the methods provided herein, the enzymatically installed hydroxyl group can be converted into a variety of other functional groups through versatile methods for chemical hydroxyl group interconversion, such as nucleophilic substitution (e.g., Mitsunobu substitution), alkylation, acylation, deoxyhalogenation, O—H carbene insertion, and the like.

Accordingly, micheliolide derivatives are provided that are modified at the level of carbon atom C2 or C14, or double-modified at the level of carbon atom C2 or C4, or C4 and C14. Furthermore, micheliolide derivatives are provided that are (doubly) functionalized at the level of carbon atoms C2 and C13 or at the level of carbon atoms C14 and C13. Notably, some of these compounds were found to possess significantly improved anticancer activity compared to MCL, while others combined improved anticancer activity with increased water solubility as compared to MCL.

A compound of general formula (A) or a salt thereof is provided:

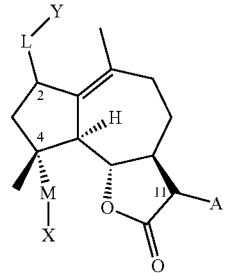

(A)

wherein
A is =$CH_2$ or —$CH_2R^*$ wherein $R^*$ is an amino acid residue bonded to the A methylene via a nitrogen or sulfur atom; or $R^*$ is —$NR^1R^2$, —$NR^1C(O)R^2$, —$NR^1CO_2R^2$, or —$SR^1$, wherein $R^1$ and $R^2$ are independently selected from the group consisting of H and an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or $R^*$ is —$NR^1R^2$, wherein $R^1$ and $R^2$ optionally together with the nitrogen atom form a an optionally substituted 5-12 membered ring, the ring optionally comprising at least one heteroatom or group selected from the group consisting of —CO—, —SO—, —$SO_2$—, and —PO—;

L is —O—, —NH—, —NHC(O)—, —OC(O)—, —OC(O)NH—, —S—, —SO—, —$SO_2$—, —PO—, —$OCH_2$—, or a chemical bond connecting the carbon atom to Y; and Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group, with the proviso that when -L-Y is hydrogen, -M-X is not hydroxyl, nor —$C(O)CH_2CH_3$ and A is not —$CH_2$—$N(CH_3)_2$, wherein -L-Y together with the carbon atom at position C2 optionally forms carbonyl; or Y is absent and L represents a halogen atom, an azido group (—$N_3$), an optionally substituted triazole group, or a group —$NR^3R^4$, where $R^3$ represents a hydrogen atom or an optionally substituted alkyl, alkenyl, or alkynyl group; $R^4$ represents an optionally substituted alkyl, alkenyl, alkynyl, aryl, or heteroaryl group; or where $R^3$ and $R^4$ are connected together to form an optionally substituted heterocyclic group;

M is —O— or —OC(O)— and X represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group.

In some embodiments, the present invention provides compounds of formula (A), wherein wherein L is —OC (O)—; Y is hydrogen, —(C$_6$-C$_{10}$) aryl, -(5-14 membered) heteroaryl, —(C$_1$-C$_6$) alkyl, —CH$_2$—(C$_6$-C$_{10}$) aryl, or —NH—(C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$, or CH$_2$R*, where R* is selected from the group consisting of methylamino (—NH(CH$_3$)), dimethylamino (—N(CH$_3$)$_2$), methylethylamino (—N(CH$_3$)(CH$_2$CH$_3$)), methylpropylamino (—N(CH$_3$)(CH$_2$CH$_2$CH$_3$)), methylisopropylamino (—(CH$_3$)(CH$_2$(CH$_3$)$_2$), (—N(CH$_3$)(CH$_2$CH$_2$OH), pyrrolidine, piperidine, 4-methylpiperidine, 1-phenylmethanamine (—NCH$_2$Ph), and 2-phenylethanamine (—NCH$_2$CHPh); M is —O—, or —OC(O)—; X is hydrogen, —(C$_6$-C$_{10}$) aryl, -(5-14 membered) heteroaryl, (C$_1$-C$_6$) alkyl, —N(CH$_3$)$_2$—(C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen. Preferably, L is —OC(O)—; Y is —(C$_6$-C$_{10}$) aryl, -(5-14 membered) heteroaryl, or —NH—(C$_6$-C$_{10}$) aryl, each of which is optionally substituted with 1 to 3 substituents selected from the group consisting of —CF$_3$, halogen, phenyl, and phenyl substituted with 1 to 2 substituents selected from —CF$_3$ and halogen; A is =CH$_2$; M is —O—, or —OC(O)—; X is hydrogen, —(C$_6$-C$_{10}$) aryl, -(5-14 membered) heteroaryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

In some embodiments, the present invention provides compounds of formula (A), wherein L is —O—; Y is —C(O)—(C$_6$-C$_{10}$) aryl, —C(O)—(5-14 membered) heteroaryl, hydrogen, —CH$_2$—(C$_6$-C$_{10}$) aryl, —C(O)—NH—(C$_6$-C$_{10}$) aryl, or —(C$_1$-C$_6$) alkyl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$, or CH$_2$R*, where R* is selected from the group consisting of methylamino (—NH(CH$_3$)), dimethylamino (—N(CH$_3$)$_2$), methylethylamino (—N(CH$_3$)(CH$_2$CH$_3$)), methylpropylamino (—N(CH$_3$)(CH$_2$CH$_2$CH$_3$)), methylisopropylamino (—(CH$_3$)(CH$_2$(CH$_3$)$_2$), (—N(CH$_3$)(CH$_2$CH$_2$OH), pyrrolidine, piperidine, 4-methylpiperidine, 1-phenylmethanamine (—NCH$_2$Ph), and 2-phenylethanamine (—NCH$_2$CHPh); M is —O—, or —OC(O)—; X is hydrogen, —(C$_6$-C$_{10}$) aryl, -(5-14 membered) heteroaryl, (C$_1$-C$_6$) alkyl, —N(CH$_3$)$_2$—(C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen. Preferably, L is —O—; Y is —(C$_6$-C$_{10}$) aryl, -(5-14 membered) heteroaryl, or —NH—(C$_6$-C$_{10}$) aryl, each of which is optionally substituted with 1 to 3 substituents selected from the group consisting of —CF$_3$, halogen, phenyl, and phenyl substituted with 1 to 2 substituents selected from —CF$_3$ and halogen; A is =CH$_2$; M is —O—, or —OC(O)—; X is hydrogen, —(C$_6$-C$_{10}$) aryl, -(5-14 membered) heteroaryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

In some embodiments, the present invention provides compounds of formula (A), wherein -L-Y is hydrogen, hydroxyl, azide, -(5-14 membered) heteroaryl, amino, halogen, —NH—C(O)—(C$_6$-C$_{10}$) aryl, wherein -(5-14 membered) heteroaryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$; M is —O—; X is hydrogen, or —C(O)—(C$_6$-C$_{10}$) aryl, wherein —C(O)—(C$_6$-C$_{10}$) aryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen. Preferably, -L-Y is hydrogen, hydroxyl, -(5-14 membered) heteroaryl, halogen, wherein -(5-14 membered) heteroaryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$; X is hydrogen, or —C(O)—(C$_6$-C$_{10}$) aryl, wherein —C(O)—(C$_6$-C$_{10}$) aryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

A compound of general formula (B) or a slat thereof is provided:

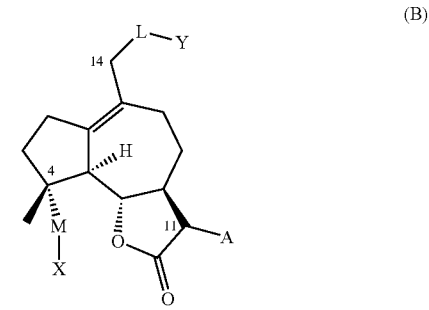

(B)

wherein

A is =CH$_2$ or —CH$_2$R* wherein R* is an amino acid residue bonded to the A methylene via a nitrogen or sulfur atom; or R* is —NR$^1$R$^2$, —NR$^1$C(O)R$^2$, —NR$^1$CO$_2$R$^2$, or —SR$^1$, wherein R$^1$ and R$^2$ are independently selected from the group consisting of H and an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or R* is —NR$^1$R$^2$, wherein R$^1$ and R$^2$ optionally together with the nitrogen atom form a an optionally substituted 5-12 membered ring, the ring optionally comprising at least one heteroatom or group selected from the group consisting of —CO—, —SO—, —SO$_2$—, and —PO—;

L is —O—, —NH—, —NHC(O)—, —OC(O)—, —OC(O)NH—, —S—, —SO—, —SO$_2$—, —PO—, —OCH$_2$—, or a chemical bond connecting the carbon atom to Y; and Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group, with the proviso that when -L-Y is hydrogen, -M-X is not hydroxyl, nor —C(O)CH$_2$CH$_3$ and A is not —CH$_2$—N(CH$_3$)$_2$, wherein -L-Y together with the carbon atom at position C2 optionally forms carbonyl; or Y is absent and L represents a halogen atom, an azido group (—N$_3$), an optionally substituted triazole group, or a group —NR$^3$R$^4$, where R$^3$ represents a hydrogen atom or an optionally substituted alkyl, alkenyl, or alkynyl group; R$^4$ represents an optionally substituted alkyl, alkenyl, alkynyl, aryl, or heteroaryl group; or where R$^3$ and R$^4$ are connected together to form an optionally substituted heterocyclic group;

M is —O— or —OC(O)— and X represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group.

In some embodiments, the present invention provides compounds of formula (B), wherein wherein L is —OC(O)—; Y is hydrogen, —(C$_6$-C$_{10}$) aryl, -(5-14 membered) heteroaryl, —(C$_1$-C$_6$) alkyl, —CH$_2$—(C$_6$-C$_{10}$) aryl, or —NH—(C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$, or CH$_2$R*, where R* is selected from the group consisting of methylamino (—NH(CH$_3$)), dimethylamino (—N(CH$_3$)$_2$), methylethylamino (—N(CH$_3$)(CH$_2$CH$_3$)), methylpropylamino (—N(CH$_3$)(CH$_2$CH$_2$CH$_3$)), methylisopropylamino (—(CH$_3$)(CH$_2$(CH$_3$)$_2$), (—N(CH$_3$)(CH$_2$CH$_2$OH), pyrrolidine, piperidine, 4-methylpiperidine, 1-phenylmethanamine (—NCH$_2$Ph), and 2-phenylethanamine (—NCH$_2$CHPh); M is —O—, or —OC(O)—; X is hydrogen, —(C$_6$-C$_{10}$) aryl, -(5-14 membered) heteroaryl, (C$_1$-C$_6$) alkyl, —N(CH$_3$)$_2$—(C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen. Preferably, L is —OC(O)—; Y is —(C$_6$-C$_{10}$) aryl, -(5-14 membered) heteroaryl, or —NH—(C$_6$-C$_{10}$) aryl, each of which is optionally substituted with 1 to 3 substituents selected from the group consisting of —CF$_3$, halogen, phenyl, and phenyl substituted with 1 to 2 substituents selected from —CF$_3$ and halogen; A is =CH$_2$; M is —O—, or —OC(O)—; X is hydrogen, —(C$_6$-C$_{10}$) aryl, -(5-14 membered) heteroaryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

In some embodiments, the present invention provides compounds of formula (B), wherein L is —O—; Y is —C(O)—(C$_6$-C$_{10}$) aryl, —C(O)— -(5-14 membered) heteroaryl, hydrogen, —CH$_2$—(C$_6$-C$_{10}$) aryl, —C(O)—NH—(C$_6$-C$_{10}$) aryl, or —(C$_1$-C$_6$) alkyl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$, or CH$_2$R*, where R* is selected from the group consisting of methylamino (—NH(CH$_3$)), dimethylamino (—N(CH$_3$)$_2$), methylethylamino (—N(CH$_3$)(CH$_2$CH$_3$)), methylpropylamino (—N(CH$_3$)(CH$_2$CH$_2$CH$_3$)), methylisopropylamino (—(CH$_3$)(CH$_2$(CH$_3$)$_2$), (—N(CH$_3$)(CH$_2$CH$_2$OH), pyrrolidine, piperidine, 4-methylpiperidine, 1-phenylmethanamine (—NCH$_2$Ph), and 2-phenylethanamine (—NCH$_2$CHPh); M is —O—, or —OC(O)—; X is hydrogen, —(C$_6$-C$_{10}$) aryl, -(5-14 membered) heteroaryl, (C$_1$-C$_6$) alkyl, —N(CH$_3$)$_2$— (C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen. Preferably, L is —O—; Y is —(C$_6$-C$_{10}$) aryl, -(5-14 membered) heteroaryl, or —NH—(C$_6$-C$_{10}$) aryl, each of which is optionally substituted with 1 to 3 substituents selected from the group consisting of —CF$_3$, halogen, phenyl, and phenyl substituted with 1 to 2 substituents selected from —CF$_3$ and halogen; A is =CH$_2$; M is —O—, or —OC(O)—; X is hydrogen, —(C$_6$-C$_{10}$) aryl, -(5-14 membered) heteroaryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

In some embodiments, the present invention provides compounds of formula (B), wherein -L-Y is hydrogen, hydroxyl, azide, -(5-14 membered) heteroaryl, amino, halogen, —NH—C(O)—(C$_6$-C$_{10}$) aryl, wherein -(5-14 membered) heteroaryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$; M is —O—; X is hydrogen, or —C(O)—(C$_6$-C$_{10}$) aryl, wherein —C(O)—(C$_6$-C$_{10}$) aryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen. Preferably, -L-Y is hydrogen, hydroxyl, -(5-14 membered) heteroaryl, halogen, wherein -(5-14 membered) heteroaryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$; X is hydrogen, or —C(O)—(C$_6$-C$_{10}$) aryl, wherein —C(O)—(C$_6$-C$_{10}$) aryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

A compound of general formula (I) or salt thereof is provided:

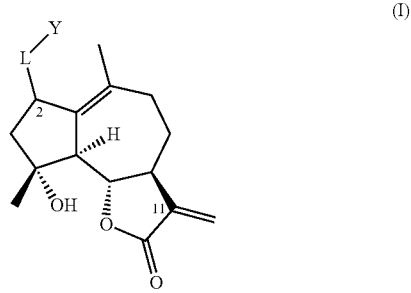

(I)

wherein

L represents —O—, —NH—, —NHC(O)—, —OC(O)—, —OC(O)NH—, —S—, —SO—, —SO$_2$—, —PO—, —OCH$_2$—, or a chemical bond connecting the carbon atom to Y; and Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or Y is absent and L represents a halogen atom, an azido group (—N₃), an optionally substituted triazole group, or L represents a group —NR³R⁴, where R³ represents a hydrogen atom or an optionally substituted alkyl, alkenyl, or alkynyl group; R⁴ represents an optionally substituted alkyl, alkenyl, alkynyl, aryl, or heteroaryl group; or where R³ and R⁴ are connected together to form an optionally substituted heterocyclic group.

A compound of general formula (II) or salt thereof is also provided:

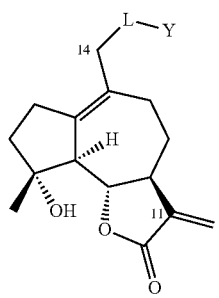

(II)

wherein

L represents —O—, —NH—, —NHC(O)—, —OC(O)—, —OC(O)NH—, —S—, —SO—, —SO₂—, —PO—, —OCH₂—, or a chemical bond connecting the carbon atom to Y; and Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or Y is absent and L represents a halogen atom, an azido group (—N₃), an optionally substituted triazole group, or L represents a group —NR³R⁴, where R³ represents a hydrogen atom or an optionally substituted alkyl, alkenyl, or alkynyl group; R⁴ represents an optionally substituted alkyl, alkenyl, alkynyl, aryl, or heteroaryl group; or where R³ and R⁴ are connected together to form an optionally substituted heterocyclic group.

A compound of general formula (III) or salt thereof is also provided:

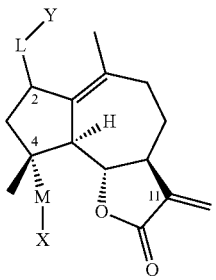

(III)

wherein

L represents —O—, —NH—, —NHC(O)—, —OC(O)—, —OC(O)NH—, —S—, —SO—, —O₂—, —PO—, —OCH₂—, or a chemical bond connecting the carbon atom to Y; and Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or Y is absent and L represents a halogen atom, an azido group (—N₃), an optionally substituted triazole group, or L represents a group —NR³R⁴, where R³ represents a hydrogen atom or an optionally substituted alkyl, alkenyl, or alkynyl group; R⁴ represents an optionally substituted alkyl, alkenyl, alkynyl, aryl, or heteroaryl group; or where R³ and R⁴ are connected together to form an optionally substituted heterocyclic group; and M represents —O—, —NH—, —NHC(O)—, —OC(O)—, —OC(O)NH—, —S—, —SO—, —O₂—, —PO—, —OCH₂—, or a chemical bond connecting the carbon atom to X; and X represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or X is absent and M represents a halogen atom, an azido group (—N₃), an optionally substituted triazole group, or M represents a group —NR³R⁴, where R³ represents a hydrogen atom or an optionally substituted alkyl, alkenyl, or alkynyl group; R⁴ represents an optionally substituted alkyl, alkenyl, alkynyl, aryl, or heteroaryl group; or where R³ and R⁴ are connected together to form an optionally substituted heterocyclic group.

A compound of general formula (IV) or salt thereof is also provided:

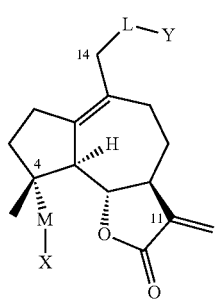

(IV)

wherein

L represents —O—, —NH—, —NHC(O)—, —OC(O)—, —OC(O)NH—, —S—, —SO—, —O₂—, —PO—, —OCH₂—, or a chemical bond connecting the carbon atom to Y; and Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or Y is absent and L represents a halogen atom, an azido group (—N₃), an optionally substituted triazole group, or L represents a group —NR³R⁴, where R³ represents a hydrogen atom or an optionally substituted alkyl, alkenyl, or alkynyl group; R⁴ represents an optionally substituted alkyl, alkenyl, alkynyl, aryl, or heteroaryl group; or where $R^3$ and $R^4$ are connected together to form an optionally substituted heterocyclic group; and M represents —O—, —NH—, —NHC(O)—, —OC(O)—, —OC(O)NH—, —S—, —SO—, —O$_2$—, —PO—, —OCH$_2$—, or a chemical bond connecting the carbon atom to X; and X represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or X is absent and M represents a halogen atom, an azido group (—N$_3$), an optionally substituted triazole group, or M represents a group —NR$^3$R$^4$, where R$^3$ represents a hydrogen atom or an optionally substituted alkyl, alkenyl, or alkynyl group; R$^4$ represents an optionally substituted alkyl, alkenyl, alkynyl, aryl, or heteroaryl group; or where R$^3$ and R$^4$ are connected together to form an optionally substituted heterocyclic group.

A compound of general formula (V) or salt thereof is also provided:

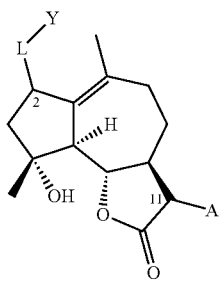

(V)

wherein

A is —CH$_2$R* wherein R* is an amino acid residue bonded to the A methylene via a nitrogen or sulfur atom; or R* is —NR$^1$R$^2$, —NR$^1$C(O)R$^2$, —NR$^1$CO$_2$R$^2$, or —SR$^1$, wherein R$^1$ and R$^2$ are independently selected from the group consisting of H and an optionally substituted alkyl, alkenyl, or alkynyl group, an optionally substituted heteroalkyl, heteroalkenyl, or heteroalkynyl group, an optionally substituted aryl group, an optionally substituted heteroaryl group, and an optionally substituted heterocyclic group; or where R* is —NR$^1$R$^2$, R$^1$ and R$^2$ optionally together with the nitrogen atom form a an optionally substituted 5-12 membered ring, the ring optionally comprising one or more heteroatoms or a group selected from the group consisting of —CO—, —SO—, —SO$_2$—, and —PO—;

L represents —O—, —NH—, —NHC(O)—, —OC(O)—, —OC(O)NH—, —S—, —SO—, —SO$_2$—, —PO—, —OCH$_2$—, or a chemical bond connecting the carbon atom to Y;

Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group;

or Y is absent and L represents a halogen atom, an azido group (—N$_3$), an optionally substituted triazole group, or L represents a group —NR$^3$R$^4$, where R$^3$ represents a hydrogen atom or an optionally substituted alkyl, alkenyl, or alkynyl group; R$^4$ represents an optionally substituted alkyl, alkenyl, alkynyl, aryl, or heteroaryl group; or where R$^3$ and R$^4$ are connected together to form an optionally substituted heterocyclic group.

A compound of general formula (VI) or salt thereof is also provided:

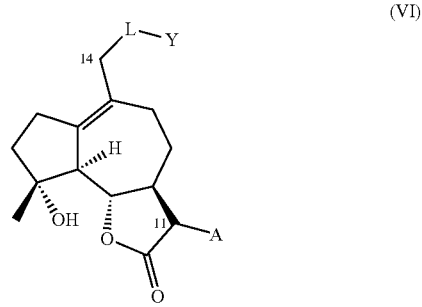

(VI)

wherein,

A is —CH$_2$R* wherein R* is an amino acid residue bonded to the A methylene via a nitrogen or sulfur atom; or R* is —NR$^1$R$^2$, —NR$^1$C(O)R$^2$, —NR$^1$CO$_2$R$^2$, or —SR$^1$, wherein R$^1$ and R$^2$ are independently selected from the group consisting of H and an optionally substituted alkyl, alkenyl, or alkynyl group, an optionally substituted heteroalkyl, heteroalkenyl, or heteroalkynyl group, an optionally substituted aryl group, an optionally substituted heteroaryl group, and an optionally substituted heterocyclic group; or where R* is —NR$^1$R$^2$, R$_1$ and R$_2$ optionally together with the nitrogen atom form a an optionally substituted 5-12 membered ring, the ring optionally comprising one or more heteroatoms or a group selected from the group consisting of —CO—, —SO—, —SO$_2$—, and —PO—;

L represents —O—, —NH—, —NHC(O)—, —OC(O)—, —OC(O)NH—, —S—, —SO—, —SO$_2$—, —PO—, —OCH$_2$—, or a chemical bond connecting the carbon atom to Y;

Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group;

or Y is absent and L represents a halogen atom, an azido group (—N$_3$), an optionally substituted triazole group, or L represents a group —NR$^3$R$^4$, where R$^3$ represents a hydrogen atom or an optionally substituted alkyl, alkenyl, or alkynyl group; R$^4$ represents an optionally substituted alkyl, alkenyl, alkynyl, aryl, or heteroaryl group; or where R$^3$ and R$^4$ are connected together to form an optionally substituted heterocyclic group.

Salts of the compounds provided herein can be prepared according to standard procedures well known in the art, for example, by reacting a compound containing a one or more sufficiently basic functional group with a suitable organic or mineral acid. Similarly, base addition salts can be prepared by reacting a compound containing a one or more sufficiently acid functional group with a suitable organic or mineral base. Examples of inorganic acid addition salts includes fluoride, chloride, bromide, iodide, sulfate, nitrate, bicarbonate, phosphate, and carbonate salts. Examples of organic acid addition salts include acetate, citrate, malonate, tartrate, succinate, lactate, malate, benzoate, ascorbate, α-ketoglutarate, tosylate, and methanesulfonate salts. Examples of base addition salts include lithium, sodium, potassium, calcium, and ammonium salts.

In specific embodiments, the substituent L in the compounds of general formula I and II is —OC(O)— and the substituent Y is phenyl, 4-pyridyl, (4-dimethylamino)phenyl, para-meta-, or orto-fluoro-phenyl, para-, meta-, or ortho-trifluoromethyl-phenyl, (2,4-bis-trifluoromethyl)phenyl, (3,5-bis-trifluoromethyl)phenyl, 1- or 2-naphthyl, 3-N-methyl-indolyl, 5-(4-chlorophenyl)isoxazolyl, 2-(4-bromophenyl)furanyl, 2-(2-(trifluoromethyl)phenyl)furanyl, or thiophene group.

In other specific embodiments, the substituent L in the compounds of general formula I and II is —O— and the substituent Y is (phenyl)methyl, (4-pyridyl)methyl, (4-dimethylaminophenyl)methyl, (para-, meta-, or ortho-fluoro-phenyl)methyl, (para-, meta-, or ortho-trifluoromethyl-phenyl)methyl, (2,4-bis-trifluoromethyl-phenyl)methyl, (3,5-bis-trifluoromethyl-phenyl)methyl, (naphthyl)methyl, (3-N-methyl-indolyl)methyl, (5-(4-chlorophenyl)isoxazolyl)methyl, (2-(4-bromophenyl)furanyl)methyl, (2-(2-(trifluoromethyl)phenyl)furanyl)methyl, or methyl (thiophene) group.

In other specific embodiments, the substituent L in the compounds of general formula I and II is —O— and the substituent Y is a group —CH(Ar')COOR', wherein Ar' is selected from the group consisting of phenyl, 4-pyridyl, (4-dimethylamino)phenyl, para-, meta-, or ortho-fluoro-phenyl, para-, meta-, or ortho-trifluoromethyl-phenyl, (2,4-bis-trifluoromethyl)phenyl, (3,5-bis-trifluoromethyl)phenyl, 1- or 2-naphthyl, 3-N-methyl-indolyl, 5-(4-chlorophenyl)isoxazolyl, 2-(4-bromophenyl)furanyl, 2-(2-(trifluoromethyl)phenyl)furanyl, and thiophene group; and the R' group is selected from the group consisting of methyl, ethyl, propyl, isopropyl, tert-butyl, benzyl, 2-morpholinoethyl, 2-morpholinoethyl, 2-(piperidin-1-yl)ethyl, and 2-(pyrrolidin-1-yl)ethyl group.

In specific embodiments, the substituent L in the compounds of general formula III and IV is —OC(O)—, the substituent Y is phenyl, 4-pyridyl, (4-dimethylamino)phenyl, para-, meta-, or orto-fluoro-phenyl, para-, meta-, or ortho-trifluoromethyl-phenyl, (2,4-bis-trifluoromethyl)phenyl, (3,5-bis-trifluoromethyl)phenyl, 1- or 2-naphthyl, 3-N-methyl-indolyl, 5-(4-chlorophenyl)isoxazolyl, 2-(4-bromophenyl)furanyl, 2-(2-(trifluoromethyl)phenyl)furanyl, or thiophene group, the substituent M is —OC(O)— and the substituent X is phenyl, 4-pyridyl, (4-dimethylamino)phenyl, para-, meta-, or orto-fluoro-phenyl, para-, meta-, or ortho-trifluoromethyl-phenyl, (2,4-bis-trifluoromethyl)phenyl, (3,5-bis-trifluoromethyl)phenyl, 1- or 2-naphthyl, 3-N-methyl-indolyl, 5-(4-chlorophenyl)isoxazolyl, 2-(4-bromophenyl)furanyl, 2-(2-(trifluoromethyl)phenyl)furanyl, or thiophene group.

In other specific embodiments, the substituent L in the compounds of general formula V and VI is —OC(O)—; the substituent Y is selected from the group consisting of phenyl, 4-pyridyl, (4-dimethylamino)phenyl, para-, meta-, or ortho-fluoro-phenyl, para-, meta-, or ortho-trifluoromethyl-phenyl, (2,4-bis-trifluoromethyl)phenyl, (3,5-bis-trifluoromethyl)phenyl, 1- or 2-naphthyl, 3-N-methyl-indolyl, 5-(4-chlorophenyl)isoxazolyl, 2-(4-bromophenyl)furanyl, 2-(2-(trifluoromethyl)phenyl)furanyl, and thiophene group; and the substituent A is —CH$_2$R*, where R* is selected from the group consisting of methylamino (—H(CH$_3$)), dimethylamino (—(CH$_3$)$_2$), methylethylamino (—N(CH$_3$)(CH$_2$CH$_3$)), methylpropylamino (—N(CH$_3$)(CH$_2$CH$_2$CH$_3$)), methylisopropylamino (—N(CH$_3$)(CH$_2$(CH$_3$)$_2$), —N(CH$_3$)(CH$_2$CH$_2$OH), pyrrolidine, piperidine, 4-methylpiperidine, 1-phenylmethanamine (—CH$_2$Ph), and 2-phenylethanamine (—NCH$_2$CH$_2$Ph).

In other specific embodiments, the substituent L in the compounds of general formula V and VI is —O—; the substituent Y is selected from the group consisting of (phenyl)methyl, (4-pyridyl)methyl, (4-dimethylaminophenyl)methyl, para-, meta-, or ortho-fluoro-phenyl)methyl, (para-, meta-, or ortho-trifluoromethyl-phenyl)methyl, (2,4-bis-trifluoromethyl-phenyl)methyl, (3,5-bis-trifluoromethyl-phenyl)methyl, (naphthyl)methyl, (3-N-methyl-indolyl)methyl, (5-(4-chlorophenyl)isoxazolyl)methyl, (2-(4-bromophenyl)furanyl)methyl, (2-(2-(trifluoromethyl)phenyl)furanyl)methyl, methyl(thiophene) group, and a —CH(Ar')COOR' group, wherein Ar' is selected from the group consisting of phenyl, 4-pyridyl, (4-dimethylamino)phenyl, para-, meta-, or ortho-fluoro-phenyl, para-, meta-, or ortho-trifluoromethyl-phenyl, (2,4-bis-trifluoromethyl)phenyl, (3,5-bis-trifluoromethyl)phenyl, 1- or 2-naphthyl, 3-N-methyl-indolyl, 5-(4-chlorophenyl)isoxazolyl, 2-(4-bromophenyl)furanyl, 2-(2-(trifluoromethyl)phenyl)furanyl, and thiophene group; and the R' group is selected from the group consisting of methyl, ethyl, propyl, isopropyl, tert-butyl, benzyl, 2-morpholinoethyl, 2-morpholinoethyl, 2-(piperidin-1-yl)ethyl, and 2-(pyrrolidin-1-yl)ethyl group; and the substituent A is —CH$_2$R*, where R* is selected from the group consisting of methylamino (—NH(CH$_3$)), dimethylamino (—(CH$_3$)$_2$), methylethylamino (—N(CH$_3$)(CH$_2$CH$_3$)), methylpropylamino (—N(CH$_3$)(CH$_2$CH$_2$CH$_3$)), methylisopropylamino (—N(CH$_3$)(CH$_2$(CH$_3$)$_2$), —(CH$_3$)(CH$_2$CH$_2$OH), pyrrolidine, piperidine, 4-methylpiperidine, 1-phenylmethanamine (—NCH$_2$Ph), and 2-phenylethanamine (—NCH$_2$CH$_2$Ph).

A person skilled in the art will promptly recognize that several different chemical methods, including different chemical reagents and reaction conditions, are available for synthesizing the compounds of general formula I and II, once the hydroxylated micheliolide derivatives, i.e. 2-hydroxy-micheliolide (2) and 14-hydroxy-micheliolide (3, respectively, are made available. Accordingly, this invention focuses on the products of these transformations rather than on the specific chemical methods applied to achieve them, which of course can vary. It should be noted, however, that the examples included in this disclosure demonstrate the feasibility of applying common, art-known chemical transformations for hydroxyl group functional interconversion for the preparation of compounds of general formula I, II, III and IV. These include substitution or functionalization of the hydroxyl group in compound 2 and 3 via alkylation, methylation, acylation, nucleophilic substitution (e.g., Mitsunobu substitution), and deoxohalogenation (e.g., deoxofluorination). As described below, compounds of general formula V and VI can be obtained by further modifying the derivatives of general formula I and II, respectively, at the C13 position according to procedures known in the art.

Compounds of general formula I, II, III and IV are prepared by first subjecting micheliolide to a reaction with a suitable P450 polypeptide in order to produce 2-hydroxy-micheliolide (compound 2) or 14-hydroxy-micheliolide (compound 3). Typically, these reactions are carried out in aqueous buffer at near-neutral pH (typically, phosphate buffer, pH 8.0) with varying amount (typically, up to 20%) of an organic solvent (typically, DMSO) to facilitate dissolution of parthenolide in the buffer. Either NAPDH or, most preferably, a NADPH cofactor regeneration system is included to provide the reducing equivalents to support the P450 reaction. Typically, a NADPH cofactor regeneration system is used, which consists of phosphite dehydrogenase, NADP$^+$, and sodium phosphite. The reaction temperature can be from 4 to 50 degree Celsius. The reaction time and concentration of the P450 polypeptide in the reaction mixture can vary widely, in large part depending on the stability, catalytic rate and, catalytic efficiency of the P450 enzyme. Typically, reaction times range from 1 to 48 hours, whereas the P450 catalyst concentration range from 0.1 to 10 mol %. Purification of the hydroxylation products can be achieved by a variety of techniques, such as by normal phase liquid chromatography through silica gel; reverse-phase liquid chromatography through bonded silica gel such as octadecylsilica, octylsilica and the like; and recrystallization using pure organic solvents or solvent mixtures. After isolation, the hydroxylated micheliolide derivatives provided herein (i.e. compounds 2 and 3) can be subjected to suitable chemical reagents and reaction conditions to functionalize or substitute the hydroxyl group in C2 or C14 with a different substituent. As mentioned above, a person skilled in the art will be able to readily select such reagents and reaction conditions for the purpose of preparing compounds of general formula I, II, III and IV from 2- and 14-hydroxy-micheliolide, respectively. For example, 2- and 14-ester derivatives can be prepared via acylation of 2-hydroxy-micheliolide and 14-hydroxy-micheliolide, respectively, with an acid chloride in dichloromethane in the presence of a weakly nucleophilic base (e.g., triethylamine, triisopropylamine, or pyridine). Alternatively, such ester derivatives can be prepared via reaction with a free acid in dichloromethane in presence of a coupling reagent (e.g., dicyclohexylcarbodiimide or DCC, O-(Benzotriazol-1-yl)-N,N,N', N'-tetramethyluronium hexafluorophosphate or HBTU), and weakly nucleophilic base (e.g., triethylamine, triisopropylamine, or pyridine). Optionally, coupling catalysts (e.g., 4-dimethylamino-pyridine or DMAP, 1-Hydroxybenzotriazole or HOBt) can be added to facilitate the esterification reaction.

Doubly substituted micheliolide derivatives of general formula V and VI can be prepared by further modifying the compounds of general formula I and II described above at the reactive position C13 according to procedures known in the art. Procedures that are useful for modification of position C13 in these compounds can be found, among other sources, in the following references (Guzman, Rossi et al. 2006; Hwang, Chang et al. 2006; Nasim and Crooks 2008; Han, Barrios et al. 2009; Neelakantan, Nasim et al. 2009; Woods, Mo et al. 2011). Additional procedures suitable for C13 modification are described in Crooks et. al, U.S. Pat. Nos. 7,312,242; 7,678,904; 8,124,652. Preferably, for the purpose of preparing compounds of general formula V and VI, these aforementioned procedures for C13 modification are chosen so that they do not alter or react with any of the functional groups comprised by the substituents installed in position C2 or C14 of the micheliolide derivatives of formula I or II, respectively. A person skilled in the art will be able to choose or adapt, if necessary, suitable procedures for this purpose.

4.6 Use of Micheliolide Derivatives for Treatment of Cancer and Other Diseases The invention also provides a pharmaceutical composition comprising an effective amount of a compound of general formula (A), (B), (I), (II, (III), (IV, (V) or (VI) or a pharmaceutically acceptable salt, ester or prodrug thereof, in combination with a pharmaceutically acceptable diluent or carrier.

The invention also provides a method of inhibiting cancer cell growth and metastasis of cancer cells, comprising administering to a mammal afflicted with cancer, an amount of a compound of general formula (A), (B), (I), (II, (III), (IV, (V) or (VI), effective to inhibit the growth of the cancer cells.

The invention also provides a method comprising inhibiting cancer cell growth by contacting the cancer cell in vitro or in vivo with an amount of a compound of formula (A), (B), (I), (II, (III), (IV, (V) or (VI), effective to inhibit the growth of the cancer cell.

The invention also provides a compound of general formulae (A), (B), (I), (II, (III), (IV, (V) or (VI) for use in medical therapy (preferably for use in treating cancer, e.g., solid tumors), as well as the use of such compound for the manufacture of a medicament useful for the treatment of cancer and other diseases/disorders described herein.

In one embodiment, the invention provides a method for inhibiting cancer cell growth. In one embodiment, the method comprises administering to a mammal afflicted with cancer an amount of a compound of the invention effective to inhibit the growth of the cancer cells. In one embodiment, the method comprises contacting the cancer cell in vitro or in vivo with an amount of a compound of the invention effective to inhibit the growth of the cancer cell.

In one embodiment, invention provides a method for treating bone marrow for human bone marrow transplant treatment of leukemia in a patient. In one embodiment, the method comprises treating bone marrow with a compound of the invention prior to reintroducing bone marrow into the patient The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the cancer is acute myeloid leukemia (AML), chronic myeloid leukemia (CML), acute lymphoblastic leukemia (ALL), mantle cell lymphoma (MCL), or large B-cell lymphoma.

In one embodiment, the cancer is prostate cancer, a brain cancer, a neuroblastoma, a lung cancer, a breast cancer, a skin cancer, a cervical cancer, a colon cancer, a ovary cancer, or a pancreatic cancer.

The invention further provides methods of treating inflammatory diseases and disorders, including, for example, rheumatoid arthritis, osteoarthritis, allergies (such as asthma), and other inflammatory conditions, such as pain (such as migraine), swelling, fever, psoriasis, inflammatory bowel disease, gastrointestinal ulcers, cardiovascular conditions, including ischemic heart disease and atherosclerosis, partial brain damage caused by stroke, skin conditions (eczema, sunburn, acne), leukotriene-mediated inflammatory diseases of lungs, kidneys, gastrointestinal tract, skin, prostatitis and paradontosis.

The invention further provides methods of treating immune response disorders, whereby the immune response is inappropriate, excessive or lacking. Such disorders include allergic responses, transplant rejection, blood transfusion reaction, and autoimmune disorders including, but not limited to, Addison's disease, alopecia areata, antiphospholipid antibody syndrome (aPL), autoimmune hepatitis, celiac disease—sprue (gluten-sensitive enteropathy), dermatomyositis, Graves' disease, Guillain-Barre syndrome, Hashimoto's disease, hemolytic anemia, idiopathic thrombocytopenic purpura, inflammatory bowel disease (IBD), inflammatory myopathies, multiple sclerosis, myasthenia gravis, pernicious anemia, primary biliary cirrhosis, psoriasis, reactive arthritis, rheumatoid arthritis, scleroderma, Sjögren's syndrome, systemic lupus erythematosus, Type I diabetes and vitiligo.

The compounds disclosed herein are useful for treating cancer. Cancers treatable by the present therapy include the solid and hematological tumors, such as leukemia, breast cancer, lung cancer, prostate cancer, colon cancer, bladder cancer, liver cancer, skin cancer, brain cancer, pancreas cancer, kidney cancer, and bone cancer, comprising administering to a mammal afflicted with the cancer an amount of micheliolide derivative effective to inhibit the viability of cancer cells of the mammal. The micheliolide derivative may be administered as primary therapy, or as adjunct therapy, either following local intervention (surgery, radiation, local chemotherapy) or in conjunction with another chemotherapeutic agent. Hematological cancers, such as the leukemias are disclosed in the Mayo Clinic Family Health Book, D. E. Larson, ed., William Morrow, N.Y. (1990) and include CLL, ALL, CML and the like. Compounds of the present invention may be used in bone marrow transplant procedure to treat bone marrow prior to reintroduction to the patient. In addition, the compounds of the present invention may be used as chemotherapy sensitizers or radiation therapy sensitizers. Accordingly, a patient, or cells, or tissues, derived from a cancer patient, are pre-treated with the compounds prior to standard chemotherapy or radiation therapy.

Within another aspect of the present invention, methods are provided for inhibiting angiogenesis in patients with non-tumorigenic, angiogenesis-dependent diseases, comprising administering a therapeutically effective amount of a composition comprising micheliolide derivative to a patient with a non-tumorigenic angiogenesis-dependent disease, such that the formation of new blood vessels is inhibited. Within other aspects, methods are provided for inhibit reactive proliferation of endothelial cells or capillary formation in non-tumorigenic, angiogenesis-dependent diseases, such that the blood vessel is effectively occluded. Within one embodiment, the anti-angiogenic composition comprising micheliolide derivative is delivered to a blood vessel which is actively proliferating and nourishing a tumor.

In addition to tumors, numerous other non-tumorigenic angiogenesis-dependent diseases, which are characterized by the abnormal growth of blood vessels, may also be treated with the anti-angiogenic micheliolide derivative compositions, or anti-angiogenic factors of the present invention. Anti-angiogenic micheliolide derivative compositions of the present invention can block the stimulatory effects of angiogenesis promoters, reducing endothelial cell division, decreasing endothelial cell migration, and impairing the activity of the proteolytic enzymes secreted by the endothelium. Representative examples of such non-tumorigenic angiogenesis-dependent diseases include corneal neovascularization, hypertrophic scars and keloids, proliferative diabetic retinopathy, arteriovenous malformations, atherosclerotic plaques, delayed wound healing, hemophilic joints, nonunion fractures, Osler-Weber syndrome, psoriasis, pyogenic granuloma, scleroderma, trachoma, menorrhagia, retrolental fibroplasia and vascular adhesions. The pathology and treatment of these conditions is disclosed in detail in published PCT application PCT/CA94/00373 (WO 95/03036). Topical or directed local administration of the present compositions is often the preferred mode of administration of therapeutically effective amounts of parthenolide derivative, i.e., in depot or other controlled release forms.

Anti-angiogenic compositions of the present invention may also be utilized in a variety of other manners. For example, they may be incorporated into surgical sutures in order to prevent stitch granulomas, implanted in the uterus (in the same manner as an IUD) for the treatment of menorrhagia or as a form of female birth control, administered as either a peritoneal lavage fluid or for peritoneal implantation in the treatment of endometriosis, attached to a monoclonal antibody directed against activated endothelial cells as a form of systemic chemotherapy, or utilized in diagnostic imaging when attached to a radioactively labelled monoclonal antibody which recognizes active endothelial cells. The magnitude of a prophylactic or therapeutic dose of micheliolide derivative, an analog thereof or a combination thereof, in the acute or chronic management of cancer, i.e., prostate or breast cancer, will vary with the stage of the cancer, such as the solid tumor to be treated, the chemotherapeutic agent(s) or other anticancer therapy used, and the route of administration. The dose, and perhaps the dose frequency, will also vary according to the age, body weight, and response of the individual patient. In general, the total daily dose range for micheliolide derivative and its analogs, for the conditions described herein, is from about 0.5 mg to about 2500 mg, in single or divided doses. Preferably, a daily dose range should be about 1 mg to about 100 mg, in single or divided doses, most preferably about 5-50 mg per day. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective amount" or "an effective sensitizing amount" are encompassed by the above-described dosage amounts and dose frequency schedule.

Any suitable route of administration may be employed for providing the patient with an effective dosage of micheliolide derivative (e.g., oral, sublingual, rectal, intravenous, epidural, intrathecal, subcutaneous, transcutaneous, intramuscular, intraperitoneal, intracutaneous, inhalation, transdermal, nasal spray, nasal gel or drop, and the like). While it is possible that, for use in therapy, micheliolide derivative or its analogs may be administered as the pure chemicals, as by inhalation of a fine powder via an insufflator, it is preferable to present the active ingredient as a pharmaceutical formulation. The invention thus further provides a pharmaceutical formulation comprising micheliolide derivative or an analog thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the agent from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. U.S. Pat. No. 4,788,603, or Bawa et al. U.S. Pat. Nos. 4,931,279; 4,668,506 and 4,713,224. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof. The polymer matrix can be coated onto, or used to form, a medical prosthesis, such as a stent, valve, shunt, graft, or the like.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds provided herein may be administered via a liquid spray, such as via a plastic bottle atomizer. Typical of these are the Mistometer® (Wintrop) and the Medihaler® (Riker).

For topical administration to the eye, the compounds can be administered as drops, gels (U.S. Pat. No. 4,255,415), gums (see U.S. Pat. No. 4,136,177) or via a prolonged-release ocular insert.

The term "treatment" refers to any treatment of a pathologic condition in a mammal, particularly a human, and includes: (i) preventing the pathologic condition from occurring in a subject which may be predisposed to the condition but has not yet been diagnosed with the condition and, accordingly, the treatment constitutes prophylactic treatment for the disease condition; (ii) inhibiting the pathologic condition, i.e., arresting its development; (iii) relieving the pathologic condition, i.e., causing regression of the pathologic condition; or (iv) relieving the conditions mediated by the pathologic condition.

The term "therapeutically effective amount" refers to that amount of a compound of the invention that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable salts" includes, but is not limited to, salts well known to those skilled in the art, for example, mono-salts (e.g., alkali metal and ammonium salts) and poly salts (e.g., di- or tri-salts,) of the compounds of the invention. Pharmaceutically acceptable salts of compounds of formulas I, II, III, IV, V or VI are where, for example, an exchangeable group, such as hydrogen in —OH, —NH—, or —P(=O)(OH)—, is replaced with a pharmaceutically acceptable cation (e.g., a sodium, potassium, or ammonium ion) and can be conveniently be prepared from a corresponding compound of formula I, II, III, IV, V or VI by, for example, reaction with a suitable base. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds provided herein may contain one or more chiral centers.

Accordingly, the compounds are intended to include racemic mixtures, diastereomers, enantiomers, and mixture enriched in one or more stereoisomer. When a group of substituents is disclosed herein, all the individual members of that group and all subgroups, including any isomers, enantiomers, and diastereomers are intended to be included in this disclosure. Additionally, all isotopic forms of the compounds disclosed herein are intended to be included in this disclosure. For example, it is understood that any one or more hydrogens in a molecule disclosed herein can be replaced with deuterium or tritium.

A person skilled in the art will also appreciate that starting materials, biological materials, reagents, synthetic methods, purification methods, analytical methods, assay methods, and biological methods other than those specifically exemplified can be employed in the practice of the invention. All art-known functional equivalents of any such materials and methods are intended to be included in the invention.

Unless defined otherwise herein, all technical and scientific terms used herein have the same meaning as commonly understood by one of ordinary skill in the art to which this disclosure pertains.

The following examples are offered by way of illustration and not by way of limitation.

5. EXAMPLES

5.1 Example 1: Isolation of Engineered P450 Polypeptides for Micheliolide Hydroxylation Initial studies, demonstrate that CYP102A1 variant FL #62 (SEQ ID NO: 2) is capable of efficiently oxidizing MCL, supporting about 280 total turnovers (TTN) and producing a mixture of 2(R)-hydroxy-MCL (compound 2), 14-hydroxy-MCL (compound 3), 14-CHO-MCL (compound 4) in 82:5:2 ratio (FIG. 1 and Table 1). These oxyfunctionalized derivatives of MCL provide valuable intermediates, not accessible via currently available synthetic methods, for re-elaboration of MCL scaffold by chemoenzymatic means.

A collection of FL #62-derived P450 variants prepared by active site mutagenesis (Zhang, El Damaty et al. 2011; Zhang, Shafer et al. 2012) was screened for activity on methoxy-functionalized probes derived from 2 and 3. Based on their relative activity on these MCL-based probes, selected P450 variants were tested for improved activity and selectivity toward micheliolide hydroxylation at position C2 and/or C14. Typically, micheliolide hydroxylation activity was determined by reactions with the P450 variant (1 µM in purified form or in cell lysate) in buffered solution (50 mM potassium phosphate, pH 8.0) in the presence of 1 mM parthenolide and a NADPH cofactor regeneration system (2 µM phosphite dehydrogenase, 150 µM NADP$^+$, 50 mM sodium phosphite). The enzymatic reactions were extracted with dichloromethane and analyzed by gas chromatography. As described in Table 1, several P450 variants derived from CYP102A1 (SEQ ID NO: 1) or FL #62 (SEQ ID NO: 2) were found to exhibit improved activity and/or selectivity in the hydroxylation of micheliolide.

TABLE 1

| | | % conversion | | |
|---|---|---|---|---|
| | Total products | 2(R)—OH-MCL | 14-CHO-MCL | 14-OH-MCL |
| CYP102A1 (SEQ ID NO. 1) | 21 | 10 | 1 | 4 |
| #62 (SEQ ID NO. 2) | 95 | 82 | 2 | 5 |
| #46 (SEQ ID NO. 3) | 100 | 22 | 31 | 43 |
| #47 (SEQ ID NO. 4) | 100 | 69 | 13 | 6 |
| IA1 | 60 | 43 | 4 | 7 |
| IB1 | 29 | 22 | 0 | 6 |
| IB3 | 49 | 44 | 0 | 4 |
| IC3 | 9 | 6 | 1 | 1 |
| ID1 | 85 | 76 | 2 | 6 |
| ID3 | 2 | 1 | 0 | 0 |
| ID5 | 34 | 26 | 2 | 5 |
| IE3 | 15 | 11 | 1 | 3 |
| IE8 | 37 | 24 | 0 | 12 |
| IF5 | 69 | 61 | 1 | 5 |
| IG1 | 42 | 26 | 11 | 4 |
| IIA4 | 30 | 22 | 2 | 6 |
| IIA12 | 10 | 5 | 4 | 0 |
| IIB4 | 9 | 3 | 1 | 3 |
| IIC1 | 26 | 22 | 2 | 2 |
| IIE2 | 21 | 6 | 9 | 5 |
| IIE12 | 21 | 11 | 9 | 1 |
| IIF8 | 77 | 60 | 4 | 10 |
| IIH8 | 100 | 64 | 13 | 22 |
| IIIA1 | 11 | 7 | 1 | 3 |
| IIIB5 | 39 | 23 | 7 | 7 |
| IIIC1 | 29 | 17 | 2 | 9 |
| IIID4 | 100 | 88 | 5 | 5 |
| IIIG5 | 5 | 2 | 1 | 1 |
| IVA9 | 55 | 45 | 3 | 4 |
| IVB9 | 10 | 5 | 2 | 2 |
| IVD3 | 16 | 13 | 1 | 1 |
| IVF8 | 10 | 3 | 1 | 4 |
| IVH10 | 52 | 46 | 1 | 3 |
| VA2 | 34 | 29 | 1 | 2 |
| VB2 | 27 | 15 | 2 | 8 |
| VC3 | 4 | 2 | 1 | 1 |
| VD7 | 47 | 43 | 1 | 2 |
| VD12 | 5 | 3 | 0 | 2 |
| VE10 | 33 | 30 | 1 | 1 |
| VH2 | 100 | 84 | 9 | 5 |
| VIA1 | 71 | 66 | 2 | 3 |
| VIC9 | 35 | 21 | 1 | 12 |
| VIE5 | 33 | 23 | 0 | 9 |

In addition, the following FL #62-derived variants were identified as promising catalyst for C2- or C14-hydroxylation in MCL:

| P450 | Active-site mutations (vs FL#62) | 2-OH-MCL | 14-OH-MCL |
|---|---|---|---|
| V-F10 (SEQ ID NO. 5) | F78, A81, A82 | 95% | 5% |
| V-H10 (SEQ ID NO. 6) | N78, F81, A82 | 35% | 65% |
| VIII-B1 (SEQ ID NO. 7) | T74, N78, F81, F87, A180 | 17% | 83% |

Experimental Details.

The P450 enzymes were expressed from pCWori-based vectors and purified by ion-exchange chromatography according to established procedures (Zhang, El Damaty et al. 2011; Zhang, Shafer et al. 2012). P450 concentration was determined from CO binding difference spectra (8450–500=91,000 M$^{-1}$ cm$^{-1}$). Site-saturation libraries were prepared using mutagenizing primers (NNK codon at target position) according to standard cloning procedures as described for example in (Zhang, El Damaty et al. 2011; Zhang, Shafer et al. 2012). To determine total turnover numbers and regioselectivity of the P450 variants, analytical-scale reactions (1 mL) were carried out using 0.2-1 µM P450, 1.5 mM micheliolide, 2 µM PTDH, 100 NM NADP$^+$, and 50 mM sodium phosphite in potassium phosphate buffer (50 mM, pH 8.0). The P450 variants were characterized either in purified form or directly from cell lysates. After 12 hours at 4° C., the reaction mixtures were added with 500 µM guaiacol (as internal standard), extracted with dichloromethane and analyzed by gas chromatography (GC). GC analyses were carried out on a Shimadzu GC2010, an FID detector, a Restek RTX-5 column (15 m×0.25 mm×0.25µm film), and the following separation program: 200° C. inlet, 300° C. detector, 130° C. oven, 12° C./min ramp to 290° C., and 290° C. for 2 min. TTN values were calculated based on the total amount of oxidation products as quantified based on the calibration curves generated using purified 2-4. Initial product formation rates were measured from 1 mL scale reactions containing 1 mM micheliolide, 0.1-1.0 µM purified P450, and 1 mM NADPH in potassium phosphate buffer (50 mM, pH 8.0) at room temperature. After 60 seconds, the samples were added with 500 µM Guaiacol and extracted with dichloromethane. Cofactor oxidation rate in the presence of parthenolide was measured by monitoring NADPH depletion at 340 nm (ε=6.22 mM$^{-1}$ cm$^{-1}$) using 0.1-0.5 μM purified P450, 1.0 mM micheliolide, and 200 μM NADPH. Coupling efficiency was calculated from the ratio between the initial product formation rate and the initial NADPH oxidation rate.

5.2 Example 2: Synthesis of 2-Hydroxy-Micheliolide and 14-Hydroxy-Micheliolide Using Purified Enzyme This example demonstrates how engineered P450 polypeptides provided herein are useful for enabling the synthesis of the derivative 2-hydroxy-micheliolide and 14-hydroxy-micheliolide at preparative scales (FIG. 1).

General Conditions for Enzymatic Reactions:

To phosphate buffer (50 mM, pH 8.0) was added P450 (2 μM), micheliolide (1 mM), NADP$^+$ (150 μM), PTDH (2 μM), and sodium phosphite (50 mM, pH 8.0). After stirring for 12 hours at room temperature, the reactions were extracted with dichloromethane (3×30 mL) and separated via centrifugation. The combined organic layers were dried over sodium sulfate, concentrated under reduced pressure, and purified by silica gel flash chromatography (10 to 60% ethyl acetate in hexanes).

To prepare 2(R)-hydroxy-micheliolide (2), 14-hydroxy-micheliolide (3) and 14-CHO-micheliolide (4), purified P450 variant II-H8 (final conc: 2.5 μM; 0.26 mol %) was dissolved in 400 mL 50 mM phosphate buffer (pH 8.0) in the presence of micheliolide (100 mg, final conc: 0.95 mM), PTDH (2 μM), NADP$^+$ (150 μM), and sodium phosphite (50 mM). The reaction mixture was stirred for 12 hours at 4° C. The crude product was extracted with dichloromethane (3×80 mL). The collected organic layers were dried with sodium sulfate, concentrated under vacuum, and purified by flash chromatography (hexanes/ethyl acetate: 1/2) to afford 2 (64 mg, 62%), 3 (22 mg, 21%) and 4 (13 mg, 11%). 2(R)-hydroxy-micheliolide (2): $^1$H NMR (500 MHz, CDCl$_3$) δ=1.32 (s, 3H), 1.34-1.43 (m, 1H), 1.91-1.95 (m, 4H), 2.13 (d, 1H, J=13.8 Hz), 2.21-2.30 (m, 2H), 2.34 (dd, 2H, J=14.5, 27.1 Hz), 2.72 (t, 1H, J=9.7 Hz), 3.02 (d, 1H, J=10.3 Hz), 3.73 (t, 1H, J=10.1 Hz), 4.64 (t, 1H, J=5.8 Hz), 5.30 (s, 1H), 5.50 (d, 1H, J=1.9 Hz), 6.22 (d, 1H, J=2.7 Hz); $^{13}$C NMR (126 MHz, CDCl$_3$) δ=24.07, 24.61, 25.86, 35.59, 48.59, 49.88, 58.52, 71.91, 77.93, 83.65, 119.60, 136.25, 138.22, 138.76, 169.45; MS (ESI) calcd for C$_{15}$H$_{20}$O$_4$ m/z: 264.32; found: 287.2 [M+Na]$^+$, 551.2 [2M+Na]$^+$, 567.2 [2M+K]$^+$. The 2(R) configuration was assigned based on the observed strong NOE signal (2.6%) between the 5(H) proton and 2P(H) proton and the total absence of NOE signal between 6(H) proton and 2a(H) proton; these values were compared with the ones in MCL, where the NOE signal between the 5(H) proton and 2P(H) proton was around 3.2% and the NOE signal between 6(H) proton and 2a(H) proton was around 2.9%, therefore indicating the presence of the hydroxyl group in position 2(R). 14-hydroxy-micheliolide (3): $^1$H NMR (500 MHz, CDCl$_3$) δ 1.27-1.36 (m, 4H), 1.74-1.80 (m, 1H), 1.84 (dd, 1H, J=7.8, 16.5 Hz), 2.13-2.21 (m, 3H), 2.26-2.36 (m, 2H), 2.52 (d, 1H, J=8.4 Hz), 2.56 (d, 1H, J=8.2 Hz), 2.61-2.73 (m, 2H), 2.80 (d, 1H, J=10.5 Hz), 3.81 (t, 1H, J=10.3 Hz), 4.08 (s, 1H), 5.51 (d, 1H, J=2.9 Hz), 6.21 (d, 1H, J=3.2 Hz); $^{13}$C NMR (126 MHz, CDCl$_3$) δ=22.80, 25.85, 28.97, 30.35, 38.30, 50.08, 58.80, 65.53, 80.04, 84.06, 119.67, 134.32, 136.75, 138.71, 169.55; MS (ESI) calcd for C$_{15}$H$_{20}$O$_4$ m/z: 264.32; found: 287.2 [M+Na]$^+$, 551.2 [2M+Na]$^+$. 14-CHO-micheliolide (4): $^1$H NMR (500 MHz, CDCl$_3$): δ=1.31-1.40 (m, 4H), 1.81 (t, 1H, J=15.5 Hz), 1.96-1.99 (m, 2H), 2.24 (d, 1H, J=13.5 Hz), 2.76-2.80 (m, 3H), 3.07 (d, 1H, J=10.5 Hz), 3.17 (d, 1H, J=7.0 Hz), 3.35 (d, 1H, J=3.5 Hz), 3.85 (t, 1H, J=10.5 Hz), 5.56 (s, 1H), 6.26 (s, 1H), 10.0 (s, 1H); $^{13}$C NMR (126 MHz, CDCl$_3$) δ=26.1, 26.8, 28.0, 32.3, 40.1, 48.6, 58.4, 78.9, 80.3, 122.4, 138.9, 141.2, 170.0, 173.2, 188.9; MS (ESI) calcd for C$_{15}$H$_{18}$O$_4$ m/z: 262.31; found: 263.4 [M+H]$^+$, 285.3 [M+Na]$^+$, 301.3 [M+K]$^+$, 547.2 [2M+Na]$^+$.

5.3 Example 3: Synthesis of 2-Hydroxy-Micheliolide and 14-Hydroxy-Micheliolide Using Whole-Cell Systems This example demonstrates how whole-cell systems containing engineered P450 polypeptides provided herein, are useful for enabling the synthesis of the derivative 2-hydroxy-micheliolide and 14-hydroxy-micheliolide at preparative scales.

General Conditions for Whole-Cell Reactions:

E. coli cells (DH5α) were transformed with a pCWori-based plasmid encoding for the desired P450 under IPTG inducible promoter and a second, pAcyc-based plasmid encoding for the phosphite dehydrogenase (PTDH) enzyme under an arabinose-inducible promoter. Cells were grown in TB medium containing ampicillin (50 mg/L) and chloramphenicol (34 mg/L) until OD$_{600}$ reached 1.0. The cells were then induced with IPTG (0.2 mM) and arabinose (0.1%) and harvested after 24 hours. Cells were then resuspended in phosphate buffer and permeabilized via two cycles of freezing/thawing. Micheliolide (100 mg) and phosphite (50 mM) were added to the cell suspension, which was stirred for 12 hours. The micheliolide hydroxylation products were extracted using dichloromethane and purified via flash chromatography as described above.

E. coli cells expressing P450 variant II-H8 were utilized for the synthesis of 2(R)-hydroxy-micheliolide (2), 14-hydroxy-micheliolide and 14-Cho-micheliolide by incubating a suspension of these cells (from 0.5 L culture) with micheliolide (100 mg). Under unoptimized conditions, 2(R)-hydroxy-micheliolide (2) was isolated from these reactions in 58% yield, 14-hydroxy-micheliolide (3) was isolated from these reactions in 18% yield and 14-CHO-micheliolide (4) was isolated from these reactions in 6% yield.

5.4 Example 4: Synthesis of C2-Substituted Micheliolide Derivatives

Figure 2:
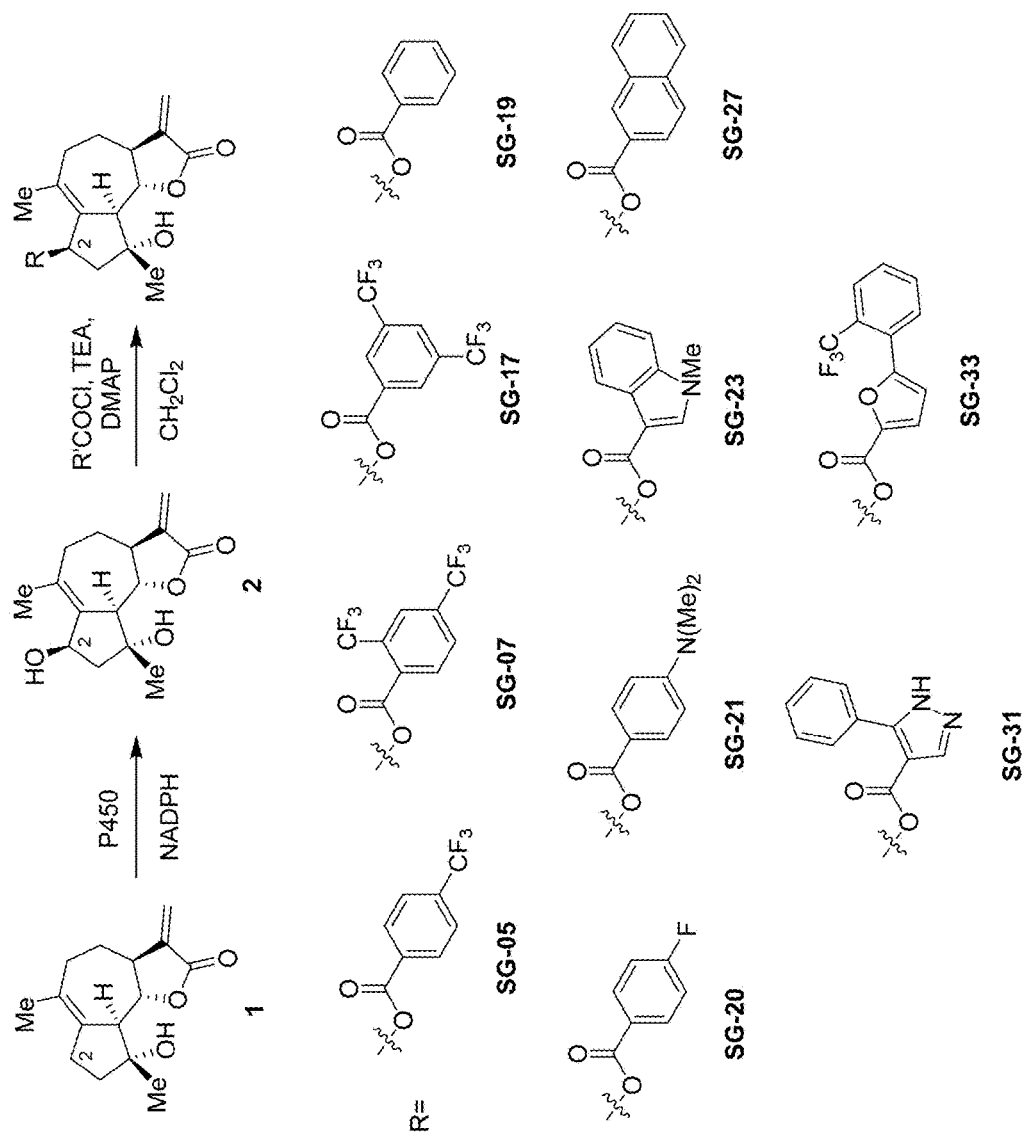
FIG. 2 depicts the synthesis and chemical structures of C2-substituted derivatives of micheliolide prepared according to the methods provided herein.

This example describes and demonstrates the preparation of compounds of general formula I according to the methods provided herein. In particular, this example illustrates how C2-substituted micheliolide analogs could be prepared by coupling selective P450-catalyzed hydroxylation of the C2 site in micheliolide followed by chemical acylation (FIG. 2).

General Conditions for Acylation of 2(R)-Hydroxy-Micheliolide:

To a solution of compound 2 in 3 mL of anhydrous dichloromethane under argon atmosphere was added 4-dimethylaminopyridine (1 equiv.), triethylamine (5 equiv.), and the corresponding acid chloride (5 equiv.). Reaction was stirred at room temperature until complete disappearance of the starting material (ca. 2 hours). At this point, the reaction mixture was added with saturated sodium bicarbonate solution (5 mL) and extracted with dichloromethane (3×5 mL). The combined organic layers were dried over sodium sulfate, concentrated under reduced pressure, and the ester product was isolated by silica gel flash chromatography (5 to 40% ethyl acetate in hexanes). Chemical structures of representative C2-substituted derivatives prepared according to the aforementioned procedure are provided in FIG. 2. Reagent concentration and characterization data for the 2-substituted micheliolide derivatives are provided below.

SG-05: Standard procedure was applied using 2(R)—OH-MCL (30 mg, 0.11 mmol), 4-dimethylaminopyridine (14 mg, 0.11 mmol), triethylamine (74 μL, 0.56 mmol), and 4-(trifluoromethyl)benzoyl chloride (17 μL, 0.11 mmol). Isolated SG-05: 24 mg, 49% yield. $^1$H NMR (500 MHz, CDCl$_3$): δ=1.34 (s, 3H), 1.39-1.48 (m, 1H), 1.70 (s, 3H), 2.01 (dd, 1H, J=8.6, 12.5 Hz), 2.18 (d, 1H, J=11.8 Hz), 2.34-2.45 (m, 3H), 2.59 (dd, 1H, J=7.8, 12.7 Hz), 2.79 (t, 1H, J=9.3 Hz), 3.11 (d, 1H, J=8.2 Hz), 3.87 (t, 1H, J=10.1 Hz), 5.57 (d, 1H, J=2.7 Hz), 5.84 (t, 1H, J=7.5 Hz), 6.28 (d, 1H, J=3.1 Hz), 7.71 (d, 2H, J=8.1 Hz), 8.14 (d, 2H, J=8.0 Hz); $^{13}$C NMR (126 MHz, CDCl$_3$) δ=24.15, 24.28, 25.79, 35.80, 45.52, 48.51, 58.27, 74.58, 83.95, 120.35, 125.46, 130.00 (4C), 130.86, 133.19, 134.47, 134.73, 138.26, 139.18, 164.89, 169.31; $^{19}$F NMR (376 MHz, CDCl$_3$): δ=−0.72; MS (ESI) calcd for C$_{23}$H$_{23}$F$_3$O$_5$ m/z: 436.43; found: 459.2 [M+Na]$^+$, 895.3 [2M+Na]$^+$.

SG-07: Standard procedure was applied using 2(R)—OH-MCL (30 mg, 0.11 mmol), 4-dimethylaminopyridine (14 mg, 0.11 mmol), triethylamine (74 μL, 0.56 mmol), and 2,4-bis(trifluoromethyl)benzoyl chloride (21 μL, 0.11 mmol). Isolated SG-07: 22 mg, 39% yield. $^1$H NMR (500 MHz, CDCl$_3$): δ=1.33 (s, 3H), 1.39-1.47 (m, 1H), 1.74 (s, 3H), 2.06 (dd, 1H, J=8.5, 13.2 Hz), 2.16 (d, 1H, J=13.7 Hz), 2.34-2.35 (m, 2H), 2.63 (dd, 1H, J=7.8, 12.9 Hz), 2.69 (br s, 1H), 2.75 (t, 1H, J=9.6 Hz), 3.07 (d, 1H, J=9.6 Hz), 3.86 (t, 1H, J=10.1 Hz), 5.55 (d, 1H, J=1.6 Hz), 5.89 (t, 1H, J=7.4 Hz), 6.27 (d, 1H, J=2.1 Hz), 7.83 (d, 1H, J=8.0 Hz), 7.88 (d, 1H, J=8.0 Hz), 8.00 (s, 1H); $^{13}$C NMR (126 MHz, CDCl$_3$) δ=24.11, 24.26, 25.81, 35.62, 45.10, 48.26, 58.17, 75.75, 83.83, 115.01, 120.41, 124.04, 124.07, 128.75, 129.45, 129.72, 130.22, 130.45, 133.17, 133.44, 134.62, 138.19, 139.67, 165.06, 169.25, 182.96; $^{19}$F NMR (376 MHz, CDCl$_3$): δ=−0.86, 2.90; MS (ESI) calcd for C$_{24}$H$_{22}$F$_6$O$_5$ m/z: 504.43; found: 527.1 [M+Na]+, 543.1 [M+K]+, 1031.3 [2M+Na]+.

SG-17: Standard procedure was applied using 2(R)—OH-MCL (30 mg, 0.11 mmol), 4-dimethylaminopyridine (14 mg, 0.11 mmol), triethylamine (74 μL, 0.56 mmol), and 3,5-bis(trifluoromethyl)benzoyl chloride (20 μL, 0.11 mmol). Isolated SG-17: 33 mg, 58% yield. $^1$H NMR (500 MHz, CDCl$_3$): δ=1.35 (s, 3H), 1.45 (dd, 1H, J=14.0, 26.6 Hz), 1.70 (s, 3H), 2.02 (dd, 1H, J=8.6, 12.5 Hz), 2.20 (dd, 1H, J=2.3, 13.8 Hz), 2.33-2.41 (m, 1H), 2.47 (t, 1H, J=15.2 Hz), 2.60 (dd, 1H, J=7.8, 12.8 Hz), 2.69 (s, 1H), 2.82 (t, 1H, J=10.4 Hz), 3.14 (d, 1H, J=10.3 Hz), 3.88 (t, 1H, J=10.1 Hz), 5.58 (d, 1H, J=2.9 Hz), 5.88 (t, 1H, J=7.7 Hz), 6.29 (d, 1H, J=3.3 Hz), 8.08 (s, 1H), 8.46 (s, 2H); $^{13}$C NMR (126 MHz, CDCl$_3$) δ=24.03, 24.39, 25.80, 35.71, 45.40, 48.22, 58.49, 75.46, 83.75, 120.46, 124.03, 126.84, 129.71, 130.52, 131.45, 131.95, 132.17, 132.51, 132.86, 134.30, 138.32, 139.57, 163.43, 169.23; $^{19}$F NMR (376 MHz, CDCl$_3$): δ=−0.51; MS (ESI) calcd for C$_{24}$H$_{22}$F$_6$O$_5$ m/z: 504.43; found: 527.2 [M+Na]$^+$, 543.2 [M+K]$^+$, 1031.4 [2M+Na]$^+$.

SG-19: Standard procedure was applied using 2(R)—OH-MCL (30 mg, 0.11 mmol), 4-dimethylaminopyridine (14 mg, 0.11 mmol), triethylamine (74 μL, 0.56 mmol), and benzoyl chloride (13 μL, 0.11 mmol). Isolated SG-19: 15 mg, 36% yield. $^1$H NMR (500 MHz, CDCl$_3$): δ=1.25 (s, 3H), 1.34 (dd, 1H, J=9.3, 15.8 Hz), 1.70 (s, 3H), 2.01 (dd, 1H, J=8.7, 13.4 Hz), 2.18 (d, 1H, J=11.4 Hz), 2.34-2.42 (m, 2H), 2.60 (dd, 1H, J=9.1, 16.3 Hz), 2.67 (bs s, 1H), 2.78 (t, 1H, J=10.7), 3.11 (d, 1H, J=8.9 Hz), 3.85 (t, 1H, J=10.1 Hz), 5.52 (d, 1H, J=7.2 Hz), 5.84 (t, 1H, J=9.4 Hz), 6.23 (d, 1H, J=4.9 Hz), 7.45 (t, 2H, J=11.4 Hz), 7.57 (t, 1H, J=10.8 Hz), 8.03 (d, 2H, J=9.8 Hz); $^{13}$C NMR (126 MHz, CDCl$_3$) δ=22.8, 25.7, 38.2, 45.5, 50.0, 58.9, 74.5, 83.6, 119.7, 128.4 (2C), 128.7, 129.5 (2C), 130.0, 133.1, 138.5, 138.9, 139.2, 140.0, 166.5, 169.4; MS (ESI) calcd for C$_{22}$H$_{24}$O$_5$ m/z: 368.43; found: 391.3 [M+Na]$^+$, 759.3 [M+Na]$^+$.

SG-20: Standard procedure was applied using 2(R)—OH-MCL (30 mg, 0.11 mmol), 4-dimethylaminopyridine (14 mg, 0.11 mmol), triethylamine (74 μL, 0.56 mmol), and 4-fluorobenzoyl chloride (13 μL, 0.11 mmol). Isolated SG-20: 17 mg, 38% yield. $^1$H NMR (500 MHz, CDCl$_3$): δ=1.34 (s, 3H), 1.44 (dd, 1H, J=11.1, 22.5 Hz), 1.70 (s, 3H), 1.99 (dd, 1H, J=8.6, 12.6 Hz), 2.17 (dd, 1H, J=2.3, 13.8 Hz), 2.30-2.47 (m, 3H), 2.57 (dd, 1H, J=7.8, 12.7 Hz), 2.77 (t, 1H, J=10.5 Hz), 3.09 (dd, 1H, J=2.2, 10.2 Hz), 3.86 (t, 1H, J=10.2 Hz), 5.55 (t, 1H, J=7.1 Hz), 5.80 (t, 1H, J=7.7 Hz), 6.27 (d, 1H, J=3.3 Hz), 7.05-7.16 (m, 2H), 8.04 (dd, 2H, J=5.5, 8.7 Hz); $^{13}$C NMR (126 MHz, CDCl$_3$) δ=24.07, 24.27, 25.80, 35.79, 45.80, 48.55, 58.35, 74.27, 84.00, 115.75 (2C), 120.51, 126.21, 131.18, 132.27 (2C), 138.39, 139.02, 164.84, 165.35, 167.04, 169.45; $^{19}$F NMR (376 MHz, CDCl$_3$): δ −43.0; MS (ESI) calcd for C$_{22}$H$_{23}$FO$_5$ m/z: 386.42; found: 409.3 [M+Na]$^+$, 425.2 [M+K]$^+$, 795.4 [2M+Na]$^+$, 811.4 [2M+K]$^+$.

SG-21: Standard procedure was applied using 2(R)—OH-MCL (30 mg, 0.11 mmol), 4-dimethylaminopyridine (14 mg, 0.11 mmol), triethylamine (74 μL, 0.56 mmol), and 4-(dimethylamino)benzoyl chloride (21 mg, 0.11 mmol). Isolated SG-21: 9 mg, 18% yield. $^1$H NMR (500 MHz, CDCl$_3$): δ=1.31-1.39 (m, 4H), 1.69 (s, 3H), 1.88 (dd, 1H, J=8.4, 15.3 Hz), 1.91 (dd, 1H, J=9.3, 11.2 Hz), 2.12-2.25 (m, 1H), 2.42 (t, 1H, J=10.8 Hz), 2.58-2.62 (m, 1H), 2.65-2.73 (m, 2H), 2.85 (d, 1H, J=8.8 Hz), 3.04 (s, 6H), 3.85 (t, 1H, J=7.6 Hz), 5.50 (s, 1H), 5.80 (t, 1H, J=11.6 Hz), 6.22 (d, 1H, J=5.7 Hz), 6.66 (d, 2H, J=12.4 Hz), 7.89 (d, 2H, J=11.9 Hz); $^{13}$C NMR (126 MHz, CDCl$_3$) δ=22.8, 25.7, 293, 30.7, 38.2, 40.1 (2C), 45.1, 50.1, 58.9, 72.8, 83.8, 110.8, 114.2, 119.6, 122.4, 130.6, 131.3 (2C), 138.6, 139.1, 153.3, 166.8, 169.5; MS (ESI) calcd for C$_{24}$H$_{29}$NO$_5$ m/z: 411.50; found: 434.3 [M+Na]$^+$, 450.2 [M+K]$^+$, 845.4 [2M+Na]$^+$, 861.2 [2M+K]$^+$.

SG-23: Standard procedure was applied using 2(R)—OH-MCL (30 mg, 0.11 mmol), 4-dimethylaminopyridine (14 mg, 0.11 mmol), triethylamine (74 μL, 0.56 mmol), and 1-methylindole-3-carbonyl chloride (21 mg, 0.11 mmol), previously synthesized as described. Isolated SG-23: 18 mg, 37% yield. $^1$H NMR (500 MHz, CDCl$_3$): δ=1.53 (s, 3H), 1.59-1.63 (m, 1H), 1.84 (s, 3H), 2.15 (dd, 1H, J=6.4, 15.2 Hz), 2.28 (d, 1H, J=11.4 Hz), 2.42-2.54 (m, 2H), 2.68 (dd, 1H, J=9.7, 18.4 Hz), 2.84 (t, 1H, J=7.6 Hz), 3.15 (d, 1H, J=6.7 Hz), 3.82-3.94 (m, 5H), 5.51 (d, 1H, J=4.2 Hz), 5.88 (t, 1H, J=11.5 Hz), 6.22 (d, 1H, J=3.7 Hz), 7.28-7.37 (m, 3H), 7.79 (s, 1H), 8.10 (d, 1H, J=12.4 Hz); $^{13}$C NMR (126 MHz, CDCl$_3$) δ=22.8, 25.7, 29.3, 30.9, 33.5, 38.3, 45.1, 50.1, 58.9, 60.4, 72.3, 83.8, 109.9, 119.6, 121.5, 122.0, 122.9, 126.5, 130.6, 135.3, 137.2, 138.6, 139.2, 164.9, 169.5; MS (ESI) calcd for C$_{25}$H$_{27}$NO$_5$ m/z: 421.49; found: 444.3 [M+Na]$^+$, 865.5 [2M+Na]$^+$.

SG-27: Standard procedure was applied using 2(R)—OH-MCL (30 mg, 0.11 mmol), 4-dimethylaminopyridine (14 mg, 0.11 mmol), triethylamine (74 μL, 0.56 mmol), and 2-naphthylcarbonyl chloride (21 mg, 0.11 mmol), previously synthesized as described. Isolated SG-27: 20 mg, 41% yield. $^1$H NMR (500 MHz, CDCl$_3$): δ=1.37 (s, 3H), 1.41 (q, 1H, J=9.5 Hz), 1.74 (s, 3H), 2.08 (dd, 1H, J=6.4, 18.5 Hz), 2.18 (d, 1H, J=12.4 Hz), 2.37 (d, 1H, J=13.3 Hz), 2.47 (t, 1H, J=11.0 Hz), 2.61 (dd, 1H, J=6.7, 15.8 Hz), 2.82 (t, 1H, J=9.7

Hz), 3.14 (d, 1H, J=11.8 Hz), 3.89 (t, 1H, J=10.5 Hz), 5.57 (d, 1H, J=3.4 Hz), 5.89 (t, 1H, J=8.8 Hz), 6.28 (d, 1H, J=4.1 Hz), 7.53-7.61 (m, 2H), 7.88 (d, 2H, J=8.5 Hz), 7.96 (d, 1H, J=8.6 Hz), 8.04 (d, 1H, J=9.1 Hz), 8.58 (s, 1H); $^{13}$C NMR (126 MHz, CDCl$_3$) δ=24.2, 24.3, 25.8, 35.8, 45.6, 48.6, 58.3, 74.0, 84.0, 120.2, 125.2, 126.7, 127.2, 127.7, 128.2, 128.3, 129.3, 129.5, 131.0, 131.1, 132.5, 135.5, 138.3, 138.9, 166.2, 169.4; MS (ESI) calcd for $C_{26}H_{26}O_5$ m/z: 418.49; found: 441.4 [M+Na]$^+$, 457.3 [M+K]$^+$, 859.6 [2M+Na]$^+$, 875.4 [2M+K]$^+$.

SG-31: Standard procedure was applied using 2(R)—OH-MCL (30 mg, 0.11 mmol), 4-dimethylaminopyridine (14 mg, 0.11 mmol), triethylamine (74 μL, 0.56 mmol), and 5-phenylpyrazole-4-carbonyl chloride (23 mg, 0.11 mmol), previously synthesized as described. Isolated SG-31: 6 mg, 12% yield. $^1$H NMR (500 MHz, CDCl$_3$): δ=1.37 (s, 3H), 1.51 (dd, 2H, J=6.6, 18.9 Hz), 1.74 (s, 3H), 2.06 (dd, 1H, J=7.2, 14.9 Hz), 2.18 (d, 1H, J=10.5 hz), 2.35-2.52 (m, 3H), 2.62 (dd, 3H, J=9.4, 15.7 Hz), 2.81 (t, 1H, J=8.9 Hz), 3.19 (d, 1H, J=10.2 Hz), 3.89 (t, 1H, J=10.5 Hz), 5.49 (d, 1H, J=9.5 Hz), 6.22 (d, 1H, J=9.8 Hz), 7.38-7.49 (m, 3H), 7.61-7.68 (m, 2H), 8.06 (s, 1H); $^{13}$C NMR (126 MHz, CDCl$_3$) δ=22.2, 22.6, 25.6, 30.2, 30.8, 38.2, 50.0, 59.2, 72.8, 83.2, 111.0, 119.7, 128.1 (2C), 128.2, 129.1 (2C), 129.3, 129.6, 129.9, 132.5, 139.8, 140.4, 163.0, 169.9; MS (ESI) calcd for $C_{25}H_{26}N_2O_5$ m/z: 434.49; found: 457.3 [M+Na]$^+$, 473.3 [M+K]$^+$, 891.5 [2M+Na]$^+$, 907.5 [2M+K]$^+$.

SG-33: Standard procedure was applied using 2(R)—OH-MCL (30 mg, 0.11 mmol), 4-dimethylaminopyridine (14 mg, 0.11 mmol), triethylamine (74 μL, 0.56 mmol), and 5-(2-(trifluoromethyl)phenyl)furan-2-carbonyl chloride (30 mg, 0.11 mmol), previously synthesized as described. Isolated SG-33: 22 mg, 38% yield. $^1$H NMR (500 MHz, CDCl$_3$): δ=1.32 (s, 3H), 1.42 (dd, 1H, J=10.5, 19.4 Hz), 1.74 (s, 3H), 2.03 (dd, 1H, J=3.5, 11.4 Hz), 2.17 (d, 1H, J=15.0 Hz), 2.33-2.41 (m, 2H), 2.57 (dd, 2H, J=5.2, 12.8 Hz), 2.77 (t, 1H, J=9.5 Hz), 3.10 (d, 1H, J=10.5 Hz), 3.85 (t, 1H, J=10.5 Hz), 5.56 (d, 1H, J=3.0 Hz), 5.80 (t, 1H, J=8.8 Hz), 6.27 (d, 1H, J=3.0 Hz), 6.75 (d, 1H, J=4.2 hz), 7.26 (d, 1H, J=3.9 Hz), 7.51 (t, 1H, J=7.5 Hz), 7.62 (t, 1H, J=7.5 Hz), 7.76-7.84 (m, 2H); $^{13}$C NMR (126 MHz, CDCl$_3$) δ=24.2, 24.3, 25.8, 29.3, 35.7, 45.4, 48.5, 58.2, 74.1, 84.0, 119.5, 120.2, 122.4, 125.8, 129.1, 130.7, 130.8, 130.9, 131.8, 132.5, 133.3, 138.3, 139.2, 143.8, 144.8, 158.2, 169.4; $^{19}$F NMR (376 MHz, CDCl$_3$): δ=−11.3; MS (ESI) calcd for $C_{27}H_{25}F_3O_6$ m/z: 502.49; found: 525.1 [M+Na]$^+$, 541.1 [M+K]$^+$, 1027.3 [2M+Na]$^+$, 1043.2 [2M+K]$^+$.

5.5 Example 5: Synthesis of C14-Substituted Micheliolide Derivatives

Figure 3:
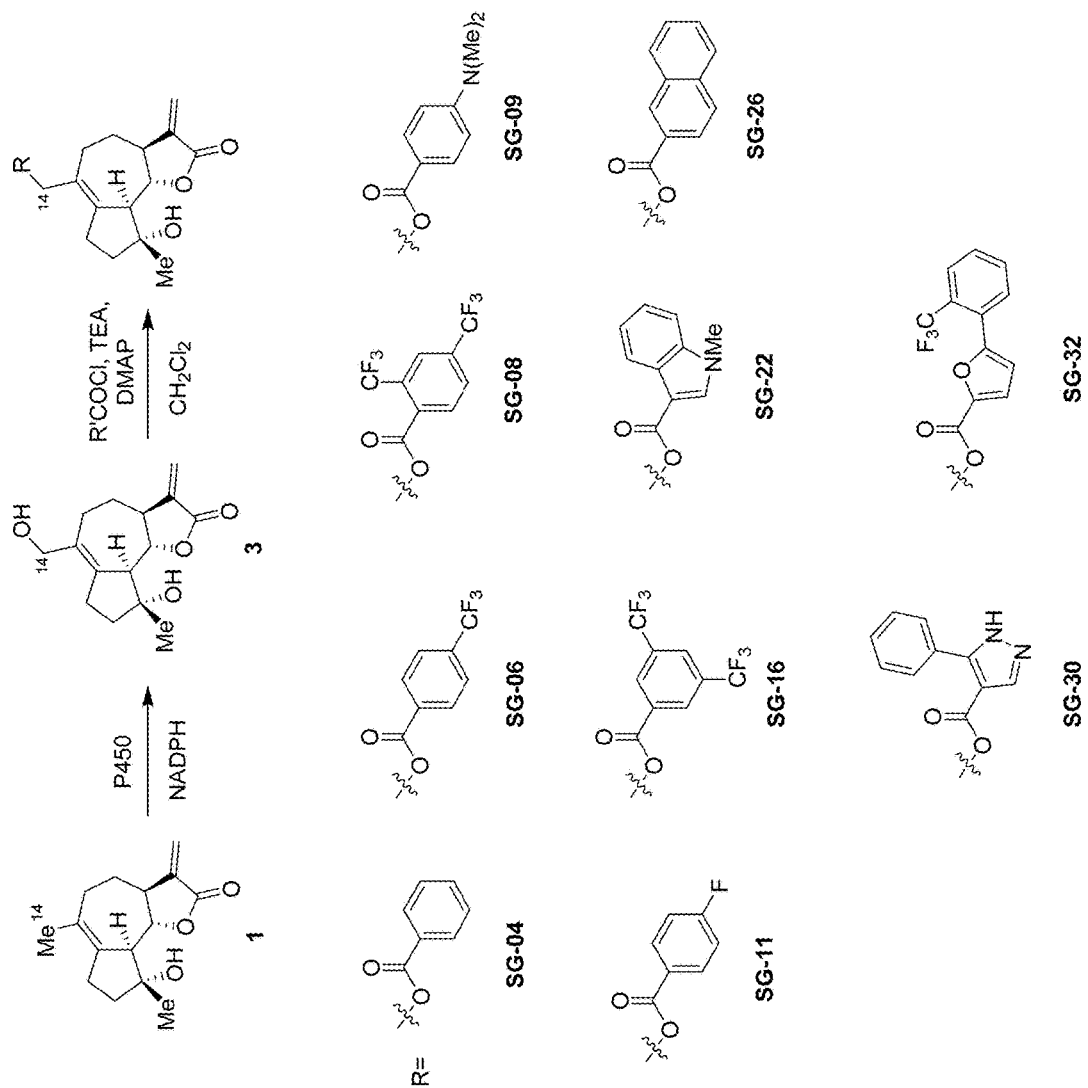
FIG. 3 depicts the synthesis and chemical structures of C14-substituted derivatives of micheliolide prepared according to the methods provided herein.

This example describes and demonstrates the preparation of compounds of general formula II according to the methods provided herein. In particular, this example illustrates how C14-substituted micheliolide analogs could be prepared by coupling selective P450-catalyzed hydroxylation of the C14 site in micheliolide followed by chemical acylation (FIG. 3).

General Conditions for Acylation of 14-Hydroxy-Micheliolide:

To a solution of compound 3 in 3 mL of anhydrous dichloromethane under argon atmosphere was added 4-dimethylaminopyridine (1 equiv.), triethylamine (5 equiv.), and the corresponding acid chloride (5 equiv.). Reaction was stirred at room temperature until complete disappearance of the starting material (ca. 2 hours). At this point, the reaction mixture was added with saturated sodium bicarbonate solution (5 mL) and extracted with dichloromethane (3×5 mL). The combined organic layers were dried over sodium sulfate, concentrated under reduced pressure, and the ester product was isolated by silica gel flash chromatography (5 to 40% ethyl acetate in hexanes). Chemical structures of representative C14-substituted derivatives prepared according to the aforementioned procedure are provided in FIG. 3. Reagent concentration and characterization data for the 14-substituted micheliolide derivatives are provided below.

SG-04: To a solution of 14-OH-MCL (30 mg, 0.11 mmol) in 3 mL of anhydrous DCM under Ar atmosphere was added 4-dimethylaminopyridine (14 mg, 0.11 mmol), triethylamine (74 μL, 0.56 mmol), and benzoyl chloride (13 μL, 0.11 mmol). Reaction was stirred at r.t (or at 40° C. if needed) until disappearance of the starting material (from 2 to 72 h). At this point, the reaction mixture was added with saturated sodium bicarbonate solution (5 mL) and extracted with DCM (3×5 mL). The combined organic layers were dried over $Na_2S_2O_4$, concentrated under reduced pressure, and the ester product was isolated by flash chromatography on silica gel (eluting mixture from 5% EtOAc in n-Hexane to 40% EtOAc in n-Hexane) to obtain 20 mg of the desired product (48% yield). $^1$H NMR (500 MHz, CDCl$_3$): δ=1.32-1.40 (m, 1H), 1.35 (s, 3H), 1.81-1.86 (m, 1H), 1.87-1.92 (m, 1H), 2.18 (d, 1H, J=13.5 Hz), 2.27 (t, 1H, J=14.2 Hz), 2.40-2.48 (m, 2H), 2.61 (d, 1H, J=16.1 Hz), 2.66-2.74 (m, 2H), 2.86 (d, 1H, J=10.6 Hz), 3.86 (t, 1H, J=10.3 Hz), 4.78 (s, 2H), 5.52 (d, 1H, J=2.9 Hz), 6.23 (d, 1H, J=3.2 Hz), 7.45 (t, 2H, J=7.4 Hz), 7.57 (t, 1H, J=7.4 Hz), 8.03 (d, 2H, J=7.6 Hz); $^{13}$C NMR (126 MHz, CDCl$_3$) δ=22.87, 25.70, 29.38, 30.86, 38.25, 50.06, 58.98, 67.65, 80.12, 83.69, 119.72, 128.46 (2C), 129.60 (2C), 130.04, 130.13, 133.10, 138.52, 140.01, 166.54, 169.46; MS (ESI) calcd for $C_{22}H_{24}O_5$ m/z: 368.43; found: 391.3 [M+Na]$^+$, 407.2 [M+K]$^+$, 759.3 [2M+Na]$^+$.

SG-06: Standard procedure was applied using 14-OH-MCL (30 mg, 0.11 mmol), 4-dimethylaminopyridine (14 mg, 0.11 mmol), triethylamine (74 μL, 0.56 mmol), and 4-(trifluoromethyl)benzoyl chloride (17 μL, 0.11 mmol). Isolated SG-06: 37 mg, 74% yield. $^1$H NMR (500 MHz, CDCl$_3$): δ=1.32-1.38 (m, 4H), 1.81-1.93 (m, 2H), 2.19 (d, 1H, J=13.5 Hz), 2.28 (t, 1H, J=14.2 Hz), 2.40-2.48 (m, 1H), 2.58 (d, 1H, J=16.3 Hz), 2.68 (d, 1H, J=8.5 Hz) 2.70-2.74 (m, 1H), 2.87 (d, 1H, J=10.5 Hz), 3.85 (t, 1H, J=10.3 Hz), 4.82 (s, 2H), 5.52 (d, 1H, J=2.7 Hz), 6.23 (d, 1H, J=3.1 Hz), 7.71 (d, 2H, J=8.1 Hz), 8.14 (d, 2H, J=8.0 Hz); $^{13}$C NMR (126 MHz, CDCl$_3$) δ=22.86, 25.69, 29.42, 30.89, 38.22, 50.03, 59.01, 68.22, 80.10, 83.57, 119.78, 124.67, 125.52, 129.58, 130.01 (4C), 133.33, 138.50, 140.65, 165.31, 169.38; $^{19}$F NMR (376 MHz, CDCl$_3$): δ=−0.73; MS (ESI) calcd for $C_{23}H_{23}F_3O_5$ m/z: 436.43; found: 459.2 [M+Na]$^+$, 475.2 [M+K]$^+$, 895.4 [2M+Na]$^+$.

SG-08: Standard procedure was applied using 14-OH-MCL (30 mg, 0.11 mmol), 4-dimethylaminopyridine (14 mg, 0.11 mmol), triethylamine (74 μL, 0.56 mmol), and 2,4-bis(trifluoromethyl)benzoyl chloride (21 μL, 0.11 mmol). Isolated SG-08: 35 mg, 60% yield. $^1$H NMR (500 MHz, CDCl$_3$): δ=1.30-1.38 (m, 4H), 1.80-1.91 (m, 2H), 2.17 (d, 1H, J=13.1 Hz), 2.28 (t, 1H, J=14.3 Hz), 2.40-2.48 (m, 1H), 2.54 (d, 1H, J=16.1 Hz), 2.63-2.73 (m, 3H), 2.85 (d, 1H, J=10.5 Hz), 3.83 (t, 1H, J=10.3 Hz), 4.77 (d, 1H, J=11.5 Hz), 4.87 (d, 1H, J=11.5 Hz), 5.52 (d, 1H, J=1.5 Hz), 6.23 (d, 1H, J=1.9 Hz), 7.89 (s, 2H), 7.99 (s, 1H); $^{13}$C NMR (126 MHz, CDCl$_3$) δ=22.77, 25.62, 29.38, 31.36, 38.14, 49.89, 59.04, 69.62, 80.07, 83.54, 119.83, 124.01, 128.87, 128.94, 129.32, 129.53, 130.93, 133.28, 133.55, 134.60, 138.38, 141.75, 165.84, 169.38; $^{19}$F NMR (376 MHz, CDCl$_3$):

δ=−0.86, 2.72; MS (ESI) calcd for $C_{24}H_{22}F_6O_5$ m/z: 504.43; found: 527.1 [M+Na]$^+$, 543.1 [M+K]$^+$, 1031.3 [2M+Na]$^+$.

SG-09: Standard procedure was applied using 14-OH-MCL (30 mg, 0.11 mmol), 4-dimethylaminopyridine (14 mg, 0.11 mmol), triethylamine (74 μL, 0.56 mmol), and 4-(dimethylamino)benzoyl chloride (21 mg, 0.11 mmol). Isolated SG-09: 19 mg, 41% yield. $^1$H NMR (500 MHz, CDCl$_3$): δ=1.31-1.39 (m, 4H), 1.79-1.91 (m, 2H), 2.16 (d, 1H, J=12.1 Hz), 2.23 (t, 1H, J=14.4 Hz), 2.38-2.46 (m, 1H), 2.58-2.73 (m, 4H), 2.85 (d, 1H, J=10.5 Hz), 3.04 (s, 6H), 3.85 (t, 1H, J=10.3 Hz), 5.51 (d, 1H, J=2.6 Hz), 6.22 (d, 1H, J=3.1 Hz), 6.66 (d, 2H, J=8.5 Hz), 7.89 (d, 2H, J=8.8 Hz); $^{13}$C NMR (126 MHz, CDCl$_3$) δ=22.89, 25.71, 29.33, 30.73, 38.39, 40.24 (2C), 50.18, 58.93, 66.82, 80.08, 83.82, 110.87, 119.62, 130.67, 131.31 (4C), 138.71, 139.05, 153.31, 166.87, 169.62; MS (ESI) calcd for $C_{24}H_{29}NO_5$ m/z: 411.50; found: 434.3 [M+Na]$^+$, 450.2 [M+K]$^+$, 845.4 [2M+Na]$^+$, 861.2 [2M+K]$^+$.

SG-11: Standard procedure was applied using 14-OH-MCL (30 mg, 0.11 mmol), 4-dimethylaminopyridine (14 mg, 0.11 mmol), triethylamine (74 μL, 0.56 mmol), and 4-fluorobenzoyl chloride (13 μL, 0.11 mmol). Isolated SG-11: 26 mg, 61% yield. $^1$H NMR (500 MHz, CDCl$_3$): δ=1.32-1.39 (m, 4H), 1.80-1.92 (m, 2H), 2.16-2.19 (m, 2H), 2.26 (t, 1H, J=20.0 Hz), 2.40-2.47 (m, 1H), 2.58 (d, 1H, J=16.0 Hz), 2.64-2.74 (m, 2H), 2.86 (d, 1H, J=10.2 Hz), 3.85 (t, 1H, J=10.3 Hz), 2.41 (s, 2H), 5.52 (d, 1H, J=2.8 Hz), 6.23 (d, 1H, J=3.1 Hz), 7.12 (t, 2H, J=8.5 Hz), 8.05 (dd, 2H, J=3.4, 10.6 Hz); $^{13}$C NMR (126 MHz, CDCl$_3$) δ=22.87, 25.69, 29.39, 30.87, 38.23, 50.05, 58.99, 67.79, 80.11, 83.64, 115.54, 115.71, 119.75, 126.36, 129.88, 132.11, 132.18 (2C), 138.47, 140.22, 166.22 (d, J=161.6 Hz), 169.25; $^{19}$F NMR (376 MHz, CDCl$_3$): δ=−42.93; MS (ESI) calcd for $C_{22}H_{23}FO_5$ m/z: 386.42; found: 409.2 [M+Na]$^+$, 425.2 [M+K]$^+$, 795.3 [2M+Na]$^+$.

SG-16: Standard procedure was applied using 14-OH-MCL (30 mg, 0.11 mmol), 4-dimethylaminopyridine (14 mg, 0.11 mmol), triethylamine (74 μL, 0.56 mmol), and 3,5-bis(trifluoromethyl)benzoyl chloride (20 μL, 0.11 mmol). Isolated SG-16: 42 mg, 79% yield. $^1$H NMR (500 MHz, CDCl$_3$): δ=1.29-1.41 (m, 4H), 1.80-1.88 (m, 1H), 1.91 (dd, 1H, J=7.9, 16.6 Hz), 2.20 (d, 1H, J=13.6 Hz), 2.29 (t, 1H, J=14.2 Hz), 2.46 (dt, 1H, J=12.6, 16.7 Hz), 2.57 (dd, 1H, J=2.5, 15.9 Hz), 2.64-2.78 (m, 3H), 2.88 (d, 1H, J=10.2 Hz), 3.86 (t, 1H, J=10.3 Hz), 4.81-4.91 (m, 2H), 5.52 (d, 1H, J=2.9 Hz), 6.23 (d, 1H, J=3.2 Hz), 8.07 (s, 1H), 8.45 (s, 2H); $^{13}$C NMR (126 MHz, CDCl$_3$) δ=22.85, 25.69, 29.56, 30.78, 38.19, 49.96, 58.97, 68.96, 80.03, 83.47, 119.99, 121.56, 123.86, 126.49, 128.94, 129.70, 131.92, 132.27, 132.43, 132.82, 138.23, 141.31, 163.79, 169.25; $^{19}$F NMR (376 MHz, CDCl$_3$): δ=−0.57; MS (ESI) calcd for $C_{24}H_{22}F_6O_5$ m/z: 504.43; found: 527.2 [M+Na]$^+$, 543.2 [M+K]$^+$, 1031.4 [2M+Na]$^+$.

SG-22: Standard procedure was applied using 14-OH-MCL (30 mg, 0.11 mmol), 4-dimethylaminopyridine (14 mg, 0.11 mmol), triethylamine (74 μL, 0.56 mmol), and 1-methylindole-3-carbonyl chloride (21 mg, 0.11 mmol). The acid chloride was freshly synthesized as follows: to a suspension of 1-methylindole-3-carboxylic acid (100 mg, 0.57 mmol) in 5 mL of anhydrous toluene under Ar atmosphere was added thionyl chloride (62 μL, 0.86 mmol) and the reaction mixture was stirred under reflux for 12 h, then cooled at r.t. and evaporated under reduced pressure. The remaining residue was used without any further purification in the next step. Isolated SG-22: 27 mg, 56% yield. $^1$H NMR (500 MHz, CDCl$_3$): δ=1.37-1.42 (m, 4H), 1.59 (br s, 1H), 1.83 (dd, 1H, J=7.8, 15.4 Hz), 1.89 (dd, 1H, J=6.5, 12.8 Hz), 2.20 (d, 1H, J=11.4 Hz), 2.29 (t, 1H, J=10.6 Hz), 2.41-2.52 (m, 1H), 2.64 (s, 1H), 2.69-2.78 (m, 2H), 2.84 (d, 1H, J=9.5 Hz), 3.82-3.89 (m, 4H), 4.79 (s, 2H), 5.51 (d, 1H, J=4.8 Hz), 6.22 (d, 1H, J=5.1 Hz), 7.28-7.33 (m, 2H), 7.36 (d, 1H, J=9.4 Hz), 7.79 (s, 1H), 8.11 (d, 1H, J=9.4 Hz); $^{13}$C NMR (126 MHz, CDCl$_3$) δ=22.8, 25.7, 29.3, 30.9, 33.5, 38.3, 50.1, 60.4, 66.3, 80.1, 83.8, 106.8, 109.9, 119.6, 121.5, 122.0, 122.9, 126.5, 130.6, 135.3, 137.2, 138.6, 139.2, 164.9, 169.5; MS (ESI) calcd for $C_{25}H_{27}NO_5$ m/z: 421.49; found: 444.3 [M+Na]$^+$, 465.5 [2M+Na]+, 881.3 [2M+K]$^+$.

SG-26: Standard procedure was applied using 14-OH-MCL (30 mg, 0.11 mmol), 4-dimethylaminopyridine (14 mg, 0.11 mmol), triethylamine (74 μL, 0.56 mmol), and 2-naphthylcarbonyl chloride (21 mg, 0.11 mmol), previously synthesized as described. Isolated SG-26: 33 mg, 69% yield. $^1$H NMR (500 MHz, CDCl$_3$): δ=1.34-1.42 (m, 4H), 1.89 (dd, 1H, J=6.3, 12.4 Hz), 1.92 (dd, 1H, J=9.4, 15.3 Hz), 2.20 (d, 1H, J=13.5 Hz), 2.30 (t, 1H, J=15.0 Hz), 2.46-2.48 (m, 1H), 2.65-2.67 (m, 2H), 2.70-2.75 (m, 2H), 2.88 (d, 1H, J=10.5 Hz), 3.87 (t, 1H, J=10.5 Hz), 4.85 (s, 2H), 5.52 (d, 1H, J=2.5 Hz), 6.23 (d, 1H, J=3.2 Hz), 7.55 (t, 1H, J=8.9 Hz), 7.60 (t, 1H, J=9.4 Hz), 7.89 (d, 2H, J=10.5 Hz), 7.96 (d, 1H, J=8.8 Hz), 8.04 (d, 1H, J=9.3 Hz), 8.59 (s, 1H); $^{13}$C NMR (126 MHz, CDCl$_3$) δ=22.9, 25.7, 29.4, 30.8, 38.2, 50.0, 59.0, 67.7, 80.1, 83.7, 119.7, 125.1, 126.7, 127.3, 127.8, 128.2, 128.3, 129.3, 130.0, 131.1, 132.4, 135.5, 138.5, 140.0, 166.7, 169.4; MS (ESI) calcd for $C_{26}H_{26}O_5$ m/z: 418.49; found: 441.4 [M+Na]$^+$, 457.3 [M+K]$^+$, 859.6 [2M+Na]$^+$, 875.5 [2M+K]$^+$.

SG-30: Standard procedure was applied using 14-OH-MCL (30 mg, 0.11 mmol), 4-dimethylaminopyridine (14 mg, 0.11 mmol), triethylamine (74 μL, 0.56 mmol), and 5-phenylpyrazole-4-carbonyl chloride (23 mg, 0.11 mmol), previously synthesized as described. Isolated SG-30: 17 mg, 34% yield. $^1$H NMR (500 MHz, CDCl$_3$): C=1.18 (q, 1H, J=8.8 Hz), 1.32 (s, 3H), 1.72-1.88 (m, 2H), 1.96-2.14 (m, 3H), 2.35-2.42 (m, 3H), 2.54 (dd, 1H, J=5.6, 17.4 Hz), 2.68 (t, 1H, J=9.8 Hz), 2.80 (d, 1H, J=10.5 Hz), 3.77 (t, 1H, J=10.5 Hz), 4.63 (s, 2H); 5.49 (d, 1H, J=4.4 Hz), 6.22 (d, 1H, J=4.2 Hz), 7.40-7.45 (m, 3H), 7.62-7.69 (m, 2H), 8.06 (s, 1H); $^{13}$C NMR (126 MHz, CDCl$_3$) δ=22.8, 25.5, 29.2, 30.8, 38.2, 50.0, 58.8, 66.8, 80.0, 83.7, 11.0, 114.9, 119.7, 128.1 (2C), 129.2 (2C), 129.5, 129.6, 129.9, 138.5, 139.8, 140.4, 163.1, 169.6; MS (ESI) calcd for $C_{25}H_{26}N_2O_5$ m/z: 434.49; found: 457.3 [M+Na]$^+$, 473.3 [M+K]$^+$, 869.6 [2M+H]$^+$, 891.5 [2M+Na]$^+$, 907.5 [2M+K]$^+$.

SG-32: Standard procedure was applied using 14-hydroxy-micheliolide (30 mg, 0.11 mmol), 4-dimethylaminopyridine (14 mg, 0.11 mmol), triethylamine (74 μL, 0.56 mmol), and 5-(2-(trifluoromethyl)phenyl)furan-2-carbonyl chloride (30 mg, 0.11 mmol), previously synthesized as described. Isolated SG-32: 35 mg, 62% yield. $^1$H NMR (500 MHz, CDCl$_3$): C=1.35-1.39 (m, 4H), 1.80-1.89 (m, 2H), 2.16-2.35 (m, 2H), 2.39-2.51 (m, 1H), 2.62 (d, 2H, J=15.2 Hz), 2.70 (dd, 2H, J=6.8, 16.7 Hz), 2.85 (d, 1H, J=10.5 Hz), 3.85 (t, 1H, J=10.5 Hz), 4.78 (dd, 2H, J=8.8, 15.3 Hz), 5.52 (d, 1H, J=2.5 Hz), 6.23 (d, 1H, J=3.0 Hz), 6.78 (d, 1H, J=3.0 Hz), 7.26 (d, 1H, J=2.9 Hz), 7.52 (t, 1H, J=7.5 Hz), 7.62 (t, 1H, J=8.0 Hz), 7.79 (t, 2H, J=7.5 Hz); $^{13}$C NMR (126 MHz, CDCl$_3$) δ=22.8, 25.6, 29.3, 29.7, 30.7, 38.2, 50.0, 58.9, 67.5, 80.1, 83.6, 111.8, 119.5, 119.7, 126.7, 127.4, 128.8, 129.1, 129.7, 130.6, 131.9, 138.5, 140.3, 144.4, 154.1, 158.5, 169.4; $^{19}$F NMR (376 MHz, CDCl$_3$): δ=−3.15; MS (ESI) calcd for $C_{27}H_{25}F_3O_6$ m/z: 502.49; found: 525.3 [M+Na]$^+$, 541.3 [M+K]$^+$, 1043.3 [2M+K]$^+$.

5.6 Example 6: Synthesis of C2,C4-Di-Substituted Micheliolide Derivatives

Figure 4:
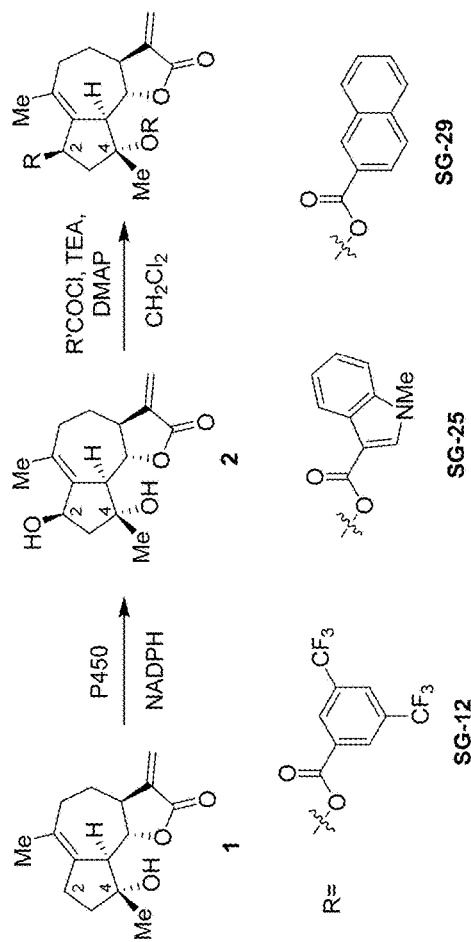
FIG. 4 depicts the synthesis and chemical structure of C2,C4-disubstituted and C4,C14-disubstituted micheliolide derivatives prepared according to the methods provided herein.
Figure 4:
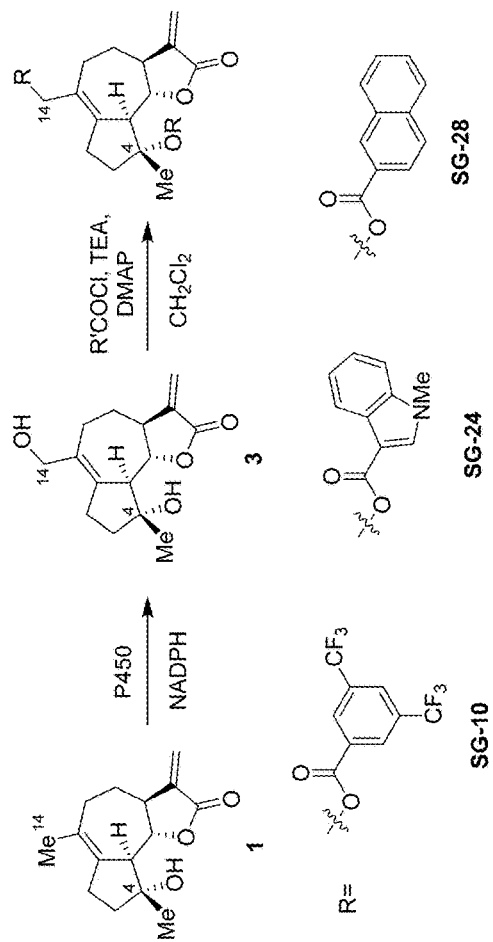

This example describes and demonstrates the preparation of compounds of general formula III according to the methods provided herein. In particular, this example illustrates how C2,C4-disubstituted micheliolide analogs could be prepared by coupling selective P450-catalyzed hydroxylation of the C2 site in micheliolide followed by chemical acylation (FIG. 4).

General Conditions for Acylation of 2,4-Di-Hydroxy-Micheliolide:

To a solution of compound 2 in 3 mL of anhydrous dichloromethane under argon atmosphere was added 4-dimethylaminopyridine (1 equiv.), triethylamine (5 equiv.), and the corresponding acid chloride (5 equiv.). Reaction was stirred at room temperature until complete disappearance of the starting material (from 2 to 12 hours). At this point, the reaction mixture was added with saturated sodium bicarbonate solution (5 mL) and extracted with dichloromethane (3×5 mL). The combined organic layers were dried over sodium sulfate, concentrated under reduced pressure, and the ester product was isolated by silica gel flash chromatography (5 to 40% ethyl acetate in hexanes). Chemical structures of representative C2,C4-disubstituted derivatives prepared according to the aforementioned procedure are provided in FIG. 4. Reagent concentration and characterization data for the 2,4-di-substituted micheliolide derivatives are provided below.

SG-12: Standard procedure was applied using 2(R)—OH-MCL (30 mg, 0.11 mmol), 4-dimethylaminopyridine (14 mg, 0.11 mmol), triethylamine (74 µL, 0.56 mmol), and 3,5-bis(trifluoromethyl)benzoyl chloride (101 µL, 0.56 mmol). Isolated SG-12: 18 mg, 21% yield. $^1$H NMR (500 MHz, CDCl$_3$): δ=1.53 (dd, 1H, J=10.2, 21.5 Hz), 1.72 (s, 3H), 1.77 (s, 3H), 2.26 (d, 1H, J=13.8 Hz), 2.42-2.46 (m, 2H), 2.50-2.60 (m, 1H), 2.94 (t, 1H, J=9.0 Hz), 3.33 (dd, 1H, J=7.9, 13.7 Hz), 3.68 (d, 1H, J=8.8 Hz), 3.95 (t, 1H, J=10.0 Hz), 5.58 (d, 1H, J=2.4 Hz), 5.99 (t, 1H, J=6.6 Hz), 6.30 (d, 1H, J=2.9 Hz), 8.03 (s, 1H), 8.05 (s, 1H), 8.40 (s, 2H), 8.47 (s, 2H); $^{13}$C NMR (126 MHz, CDCl$_3$) δ=20.27, 24.21, 25.95, 35.68, 43.55, 48.64, 56.88, 75.44, 81.88, 87.16, 119.97, 121.69, 121.78, 123. 129.61, 89, 123.95, 126.28, 126.33, 126.59, 128.25, 129.73, 129.87, 131.96, 132.03, 132.17, 132.30, 132.44, 133.19, 138.49, 141.49, 163.04, 163.36, 169.29; $^{19}$F NMR (376 MHz, CDCl$_3$): δ=−0.57 (4F); MS (ESI) calcd for $C_{33}H_{24}F_{12}O_6$ m/z: 744.53; found: 767.2 [M+Na]$^+$.

SG-25: Standard procedure was applied using 2(R)—OH-MCL (30 mg, 0.11 mmol), 4-dimethylaminopyridine (14 mg, 0.11 mmol), triethylamine (74 µL, 0.56 mmol), and 1-methylindole-3-carbonyl chloride (105 mg, 0.56 mmol), previously synthesized as described. Isolated SG-25: 11 mg, 17% yield. $^1$H NMR (500 MHz, CDCl$_3$): δ=1.38-1.50 (m, 1H), 1.62 (s, 3H), 1.69 (s, 3H), 2.14-2.22 (m, 2H), 2.27-2.41 (m, 1H), 2.52-2.63 (m, 1H), 2.64-2.70 (m, 1H), 2.70-2.86 (m, 2H), 3.37 (d, 1H, J=12.4 Hz), 3.81 (s, 3H), 3.82 (s, 3H), 3.92 (t, 1H, J=10.2 Hz), 5.52 (d, 1H, J=4.2 Hz), 5.89 (d, 1H, J=5.4 Hz), 7.27-7.39 (m, 6H), 7.82 (s, 1H), 7.92 (s, 1H), 8.16 (d, 1H, J=12.4 Hz), 8.26 (dd, 1H, J=9.4, 17.5 Hz); $^{13}$C NMR (126 MHz, CDCl$_3$) δ=19.0, 19.1, 25.9, 29.7, 30.0, 31.0 (2C), 33.4, 37.1, 45.6, 50.6, 57.9, 74.5, 87.7, 106.8, 107.9, 109.6, 109.9, 118.8, 121.7, 122.0, 122.8, 126.5, 126.8, 131.1, 135.4, 136.0, 137.2, 137.6, 139.3, 164.3, 164.9, 170.1; MS (ESI) calcd for $C_{35}H_{34}N_2O_6$ m/z: 578.67; found: 601.3 [M+Na]$^+$, 1179.5 [2M+Na]$^+$.

SG-29: Standard procedure was applied using 2(R)—OH-MCL (30 mg, 0.11 mmol), 4-dimethylaminopyridine (14 mg, 0.11 mmol), triethylamine (74 µL, 0.56 mmol), and 2-naphthylcarbonyl chloride (105 mg, 0.56 mmol), previously synthesized as described. Isolated SG-29: 23 mg, 36% yield. $^1$H NMR (500 MHz, CDCl$_3$): δ=1.47 (s, 3H), 1.67 (q, 1H, J=12.5 Hz), 1.77 (s, 3H), 2.12-2.28 (m, 2H), 2.41 (t, 1H, J=11.4 Hz), 2.56-2.63 (m, 1H), 2.71 (d, 1H, J=13.2 Hz), 2.82-2.96 (m, 1H), 3.47 (d, 1H, J=14.1 Hz), 4.04 (t, 1H, J=15.5 Hz), 5.54 (d, 1H, J=3.9 Hz), 5.92 (t, 1H, J=9.8 Hz), 6.28 (d, 1H, J=3.4 Hz), 7.51-7.62 (m, 4H), 7.80-7.90 (m, 4H), 7.92-8.09 (m, 4H), 8.62 (s, 1H), 8.72 (s, 1H); $^{13}$C NMR (126 MHz, CDCl$_3$) δ=18.6, 18.7, 25.9, 30.0, 31.0, 36.7, 50.4, 57.9, 67.9, 82.2, 88.7, 119.1, 125.1, 125.3, 126.4, 126.7, 127.6, 127.8, 128.0, 128.1, 128.4, 128.7, 129.3, 129.6, 130.8, 130.9, 131.1, 131.4, 132.5, 132.6, 133.5, 135.4, 135.6, 137.8, 139.1, 166.3, 166.7; MS (ESI) calcd for $C_{37}H_{32}O_6$ m/z: 572.66; found: 595.2 [M+Na]$^+$, 1167 [2M+Na]$^+$.

5.7 Example 7: Synthesis of C4,C14-Di-Substituted Micheliolide Derivatives

This example describes and demonstrates the preparation of compounds of general formula IV according to the methods provided herein. In particular, this example illustrates how C4,C14-disubstituted micheliolide analogs could be prepared by coupling selective P450-catalyzed hydroxylation of the C14 site in micheliolide followed by chemical acylation (FIG. 4).

General Conditions for Acylation of 4,14-Di-Hydroxy-Micheliolide:

To a solution of compound 3 in 3 mL of anhydrous dichloromethane under argon atmosphere was added 4-dimethylaminopyridine (1 equiv.), triethylamine (5 equiv.), and the corresponding acid chloride (5 equiv.). Reaction was stirred at room temperature until complete disappearance of the starting material (from 2 to 12 hours). At this point, the reaction mixture was added with saturated sodium bicarbonate solution (5 mL) and extracted with dichloromethane (3×5 mL). The combined organic layers were dried over sodium sulfate, concentrated under reduced pressure, and the ester product was isolated by silica gel flash chromatography (5 to 40% ethyl acetate in hexanes). Chemical structures of representative C4,C14-disubstituted derivatives prepared according to the aforementioned procedure are provided in FIG. 4. Reagent concentration and characterization data for the 4,14-di-substituted micheliolide derivatives are provided below.

SG-10: Standard procedure was applied using 14-OH-MCL (30 mg, 0.11 mmol), 4-dimethylaminopyridine (14 mg, 0.11 mmol), triethylamine (74 µL, 0.56 mmol), and 3,5-bis(trifluoromethyl)benzoyl chloride (101 µL, 0.56 mmol). Isolated SG-10: 30 mg, 35% yield. $^1$H NMR (500 MHz, CDCl$_3$): δ=1.43 (dd, 1H, J=12.5, 25.2 Hz), 1.73 (s, 3H), 2.15 (dd, 1H, J=12.1, 21.6 Hz), 2.26 (d, 1H, J=13.2 Hz), 2.35 (t, 1H, J=14.3 Hz), 2.61-2.64 (m, 2H), 2.74-2.78 (m, 1H), 2.85-2.90 (m, 2H), 3.41 (d, 1H, J=10.2 Hz), 3.94 (t, 1H, J=10.1 Hz), 4.91 (q, 2H, J=11.8 Hz), 5.54 (d, 1 h, J=2.0 Hz), 6.26 (d, 1H, J=2.9 Hz), 8.04 (s, 1H), 8.08 (s, 1H), 8.46 (s, 2H), 8.50 (s, 2H); $^{13}$C NMR (126 MHz, CDCl$_3$) δ=18.64, 25.71, 29.89, 30.97, 36.39, 50.21, 57.51, 68.89, 81.72, 89.91, 119.54, 121.73, 121.84, 123.90, 124.01, 126.08, 126.14, 126.18, 126.58, 126.76, 129.74, 129.90, 130.33, 131.97, 132.16, 132.24, 132.49, 133.50, 138.38, 138.56, 163.05, 163.85, 169.35; $^{19}$F NMR (376 MHz, CDCl$_3$):

δ=−0.57 (4F); MS (ESI) calcd for $C_{33}H_{24}F_{12}O_6$ m/z: 744.53; found: 767.1 [M+Na]⁺, 783.1 [M+K]⁺.

SG-24: Standard procedure was applied using 14-OH-MCL (30 mg, 0.11 mmol), 4-dimethylaminopyridine (14 mg, 0.11 mmol), triethylamine (74 μL, 0.56 mmol), and 1-methylindole-3-carbonyl chloride (105 mg, 0.56 mmol), previously synthesized as described. Isolated SG-24: 28 mg, 43% yield. ¹H NMR (500 MHz, CDCl₃): δ=1.41 (dd, 1H, J=6.5, 13.8 Hz), 1.65 (s, 3H), 2.19-2.23 (m, 2H), 2.25-2.41 (m, 1H), 2.52-2.63 (m, 1H), 2.75 (dd, 2H, J=9.8, 19.6 Hz), 2.81-2.89 (m, 2H), 3.39 (d, 1H, J=11.2 Hz), 3.78-3.86 (m, 6H), 3.95 (t, 1H, J=12.5 Hz), 4.87 (s, 2H), 5.50 (d, 1H, J=4.6 Hz), 6.22 (d, 1H, J=5.5 Hz), 7.27-7.37 (m, 6H), 7.79 (s, 1H), 7.86 (s, 1H), 8.13 (d, 1H, J=11.4 Hz), 8.23 (d, 1H, J=10.2 Hz); ¹³C NMR (126 MHz, CDCl₃) δ=19.0, 25.9, 29.7, 31.0, 33.3 (2C), 33.4, 37.1, 50.6, 60.4, 66.5, 82.5, 87.7, 106.8, 107.9, 109.6, 109.9, 118.8 (2C), 121.5, 121.7, 122.0, 122.5, 122.8, 126.5, 126.8, 131.16, 135.4, 136.0, 137.2, 137.6, 139.3, 164.3, 164.9, 170.1; MS (ESI) calcd for $C_{35}H_{34}N_2O_6$ m/z: 578.67; found: 601.3 [M+Na]⁺, 617.3 [M+K]⁺, 1179.5 [2M+Na]⁺, 1195.3 [2M+K]⁺.

SG-28: Standard procedure was applied using 14-OH-MCL (30 mg, 0.11 mmol), 4-dimethylaminopyridine (14 mg, 0.11 mmol), triethylamine (74 μL, 0.56 mmol), and 2-naphthylcarbonyl chloride (105 mg, 0.56 mmol), previously synthesized as described. Isolated SG-28: 33 mg, 51% yield. ¹H NMR (500 MHz, CDCl₃): δ=1.48 (q, 1H, J=13.0 Hz), 1.74 (s, 3H), 2.15 (q, 1H, J=12.4 Hz), 2.28 (d, 1H, J=11.6 Hz), 2.39 (t, 1H, J=13.1 Hz), 2.61-2.70 (m, 1H), 2.72 (d, 1H, J=15.0 Hz), 2.86 (dd, 1H, J=6.9, 17.4 Hz), 2.89-2.93 (m, 2H), 3.43 (d, 1H, J=10.5 Hz), 4.01 (t, 1H, J=10 Hz), 4.91 (s, 2H), 5.54 (d, 1H, J=3.5 Hz), 6.27 (1H, J=4.4 Hz), 7.51-7.62 (m, 4H), 7.82-7.91 (m, 4H), 7.93 (d, 1H, J=4.2 Hz), 8.05 (d, 1H, J=3.9 Hz), 8.06-8.09 (m, 2H), 8.61 (s, 1H), 8.72 (s, 1H); ¹³C NMR (126 MHz, CDCl₃) δ=25.9, 30.0, 31.0, 36.7, 50.4, 57.9, 67.9, 82.2, 88.7, 119.1, 15.1, 125.3, 126.4, 126.7, 127.6, 127.8, 128.0, 128.2, 128.4, 128.7, 129.3, 129.6, 130.2, 130.8, 131.1, 131.4, 131.7, 132.5, 132.6, 133.4, 135.4, 135.6, 137.8, 139.1, 166.1, 166.7, 170.5; MS (ESI) calcd for $C_{37}H_{32}O_6$ m/z: 572.66; found: 595.2 [M+Na]⁺.

5.8 Example 8: Synthesis of C2- and C14-Substituted Micheliolide Derivatives Via Other Hydroxyl Group Functionalization Methods This example further demonstrates the preparation of compounds of general formula I and II according to the methods provided herein. In particular, this example illustrates how C2- and C14-substituted micheliolide analogs could be prepared by coupling selective P450-catalyzed hydroxylation of the C2 or C14 site in micheliolide followed by chemical functionalization/interconversion of the enzymatically installed hydroxyl group (—OH).

Beside acylation, as shown in the Examples 4, 5, 6 and 7, other chemistries for functionalization/interconversion of a hydroxyl group can be coupled to P450-catalyzed micheliolide hydroxylation in order to obtain C2- or C14-substituted micheliolide derivatives according to the invention (Examples 8 and 9). These additional chemical methods include, but are not limited to, —OH group alkylation, oxidation, dehydration, Mitsunobu substitution, O—H carbene insertion, and deoxyhalogenation.

Figure 5:
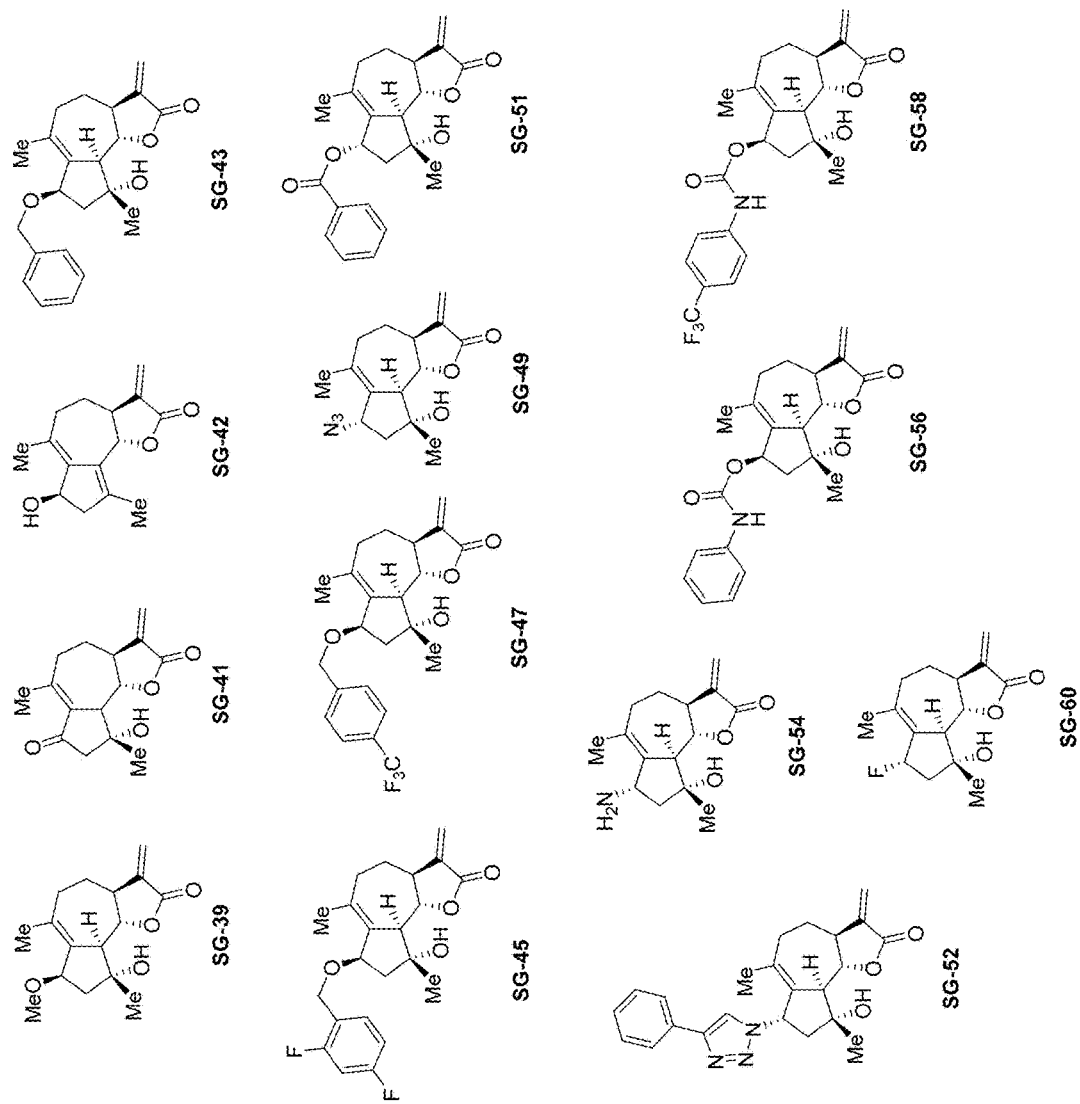
FIG. 5 depicts the chemical structures of C2-substituted derivatives of micheliolide prepared according to the methods provided herein.
Figure 6:
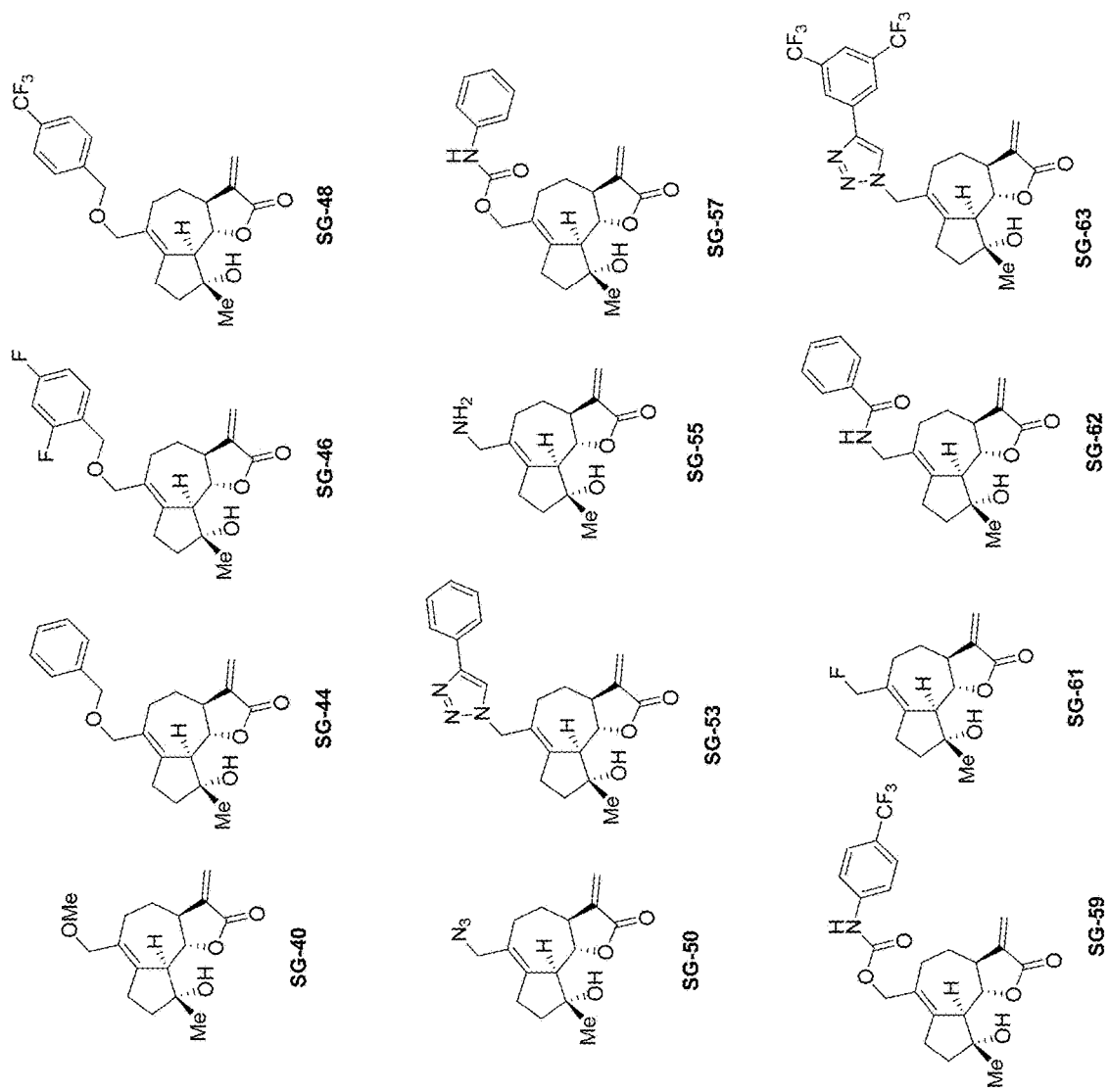
FIG. 6 depicts the chemical structures of C14-substituted derivatives of micheliolide prepared according to the methods provided herein.

For example, the enzymatically produced 2(R)-hydroxy-micheliolide and 14-hydroxy-micheliolide can be converted to 2(R)-methoxy- and 14-methoxy-derivatives via alkylation with MeI in the presence of Ag₂O as a catalyst, to afford SG-39 and SG-40 (FIGS. 5 and 6).

The keto-derivative SG-41 in FIG. 5 was obtained via reaction of the enzymatically produced 2(R)-hydroxy-micheliolide in the presence of CrO₃ as oxidizing agent.

Tertiary alcohols, like the hydroxy substituent in position 4 of the micheliolide scaffold, can be selectively dehydrated even in the presence of a primary alcohol and/or a secondary alcohol, using appropriate acidic conditions. These studies indicate that a slightly acidic solution of p-toluenesulfonic acid in DCM is useful for the selective dehydration of the C4-hydroxy group in the chemoenzymatically produced 2(R)-hydroxy-micheliolide, thus leaving untouched the newly introduced C2-hydroxy group, to bring to the formation of SG-42 (FIG. 4).

Another well established method for conversion an alcohol to an ether derivative is through direct alkylation. As illustrated by SG-43, SG-44, SG-45, SG-46, SG-47 and SG-48 (FIGS. 5 and 6), C2- and C14-substituted micheliolide derivatives could be readily obtained via alkylation of enzymatically prepared 2- and 14-hydroxy-micheliolide with the corresponding alkyl halide in the presence of KI. These studies indicate that a variety of alkyl halides and substituted derivatives thereof can be utilized for the purpose of preparing micheliolide analogs within the scope of the invention.

The Mitsunobu reaction is a powerful tool for the transformation of primary and secondary alcohols into esters, ethers, thioethers and various other compounds. Here, the focus is on the direct transformation of the enzymatically obtained 2(R)-hydroxy-micheliolide and 14-hydroxy-micheliolide into the corresponding 2(S)-azido-micheliolide and 14-azido-micheliolide through the activation of the alcohol groups by the phosphonium intermediate generated by the interaction of TPP and DEAD. DPPA complete the reaction with the formation of 2(S)-azido-micheliolide SG-49 (FIG. 5), with clear inversion of configuration, and 14-hydroxy-micheliolie SG-50 (FIG. 6).

Another useful variant of the Mitsunobu reaction allows for the direct esterification of the enzymatically prepared 2(R)-hydroxy-micheliolide in the presence of TPP and DEAD to allow the formation of SG-51, with clear inversion of configuration at C2, as illustrated in FIG. 5.

An established strategy for converting an alcohol to a carbamate derivative (i.e. R—OH→R—O(CO)NH—R') involves reacting the alcohol with a desired isocyanate reagent (e.g., aryl or alkyl isocyanate compound) in the presence of DBTDL. Accordingly, as illustrated by the successful preparation of SG-56, SG-57, SG-58 and SG-59 (FIGS. 5 and 6), C2- and C14-carbamate derivarives of micheliolide could be readily afforded upon reaction of the enzymatically produced 2(R)-hydroxy-micheliolide (2) and 14-hydroxy-micheliolide (3), respectively, with a isocyanate reagent in the presence of CBTCL. These studies indicate that a variety of isocyanate reagents can be utilized for the purpose of preparing micheliolide analogs within the scope of the invention.

The fluorination with aminosulfuranes is a useful chemical reaction that allows the transformation of oxidized organic compounds into organofluorine compounds. Accordingly to the present invention, the chemoenzymatically introduced hydroxyl group of the 2(R)-hydroxy-micheliolide can be replaced by a fluoride through the use of DUST, with clear inversion of configuration, thus leading to 2(S)-fluoro-micheliolide SG-60 (FIG. 5). The same procedure can be applied on 14-hydroxy-micheliolide for the obtainment of 14-fluoro-micheliolide SG-61, as shown in FIG. 6.

General Conditions for the Alkylation (Methylation) of 2(R)-Hydroxy-Micheliolide and 14-Hydroxy-Micheliolide:

To a stirred solution of 2(R)—OH-MCL or 14-OH-MCL (0.02 mmol) in dry DMF at r.t. an excess of $Ag_2O$ (0.1 mmol) was added and the reaction mixture was stirred 10 min at r.t. MeI (0.1 mmol) was then added and the reaction was warmed to 50° C. After 24 h, the TLC showed the formation of a new product. Few drops of $H_2O$ were added to quench the reaction mixture and then $Ag_2O$ was filtered away. The remaining organic solvent was evaporated at Hi-Vacuum and the obtained crude product was purified by flash chromatography on silica gel (eluting mixture EtOAc 50% in n-Hexane).

General Conditions for the Oxidation of 2(R)-Hydroxy-Micheliolide:

$CrO_3$ (0.9 mmol) was added portion wise to $H_2O$ (105 μL) and the resulting solution cooled at 0° C. Conc. $H_2SO_4$ (30 μL) was added dropwise and the solution stirred for 15 min. The resulting red solution was added dropwise to a solution of 2(R)—OH-MCL (0.11 mmol) in Acetone (750 μL) at 0° C. and stirred for 1 h. $H_2O$ (2 mL) and $Et_2O$ (2 mL) were added, the phases were separated and the organic layer was concentrated and purified by flash chromatography on silica gel (eluting mixture EtOAc 30% in n-Hexane).

General Conditions for the Dehydration of Position $C_4$-$C_5$ of 2(R)-Hydroxy-Micheliolide:

p-toluene-sulfonic acid (0.22 mmol) was added to a solution of 2(R)—OH-MCL (0.11 mmol) in anhydrous DCM (2 mL) at r.t. and stirred for 12 h.; $H_2O$ (5 mL) was added to the reaction mixture and the aqueous phase was extracted with EtOAc (3×). The collected organic fractions were dried in vacuo and the crude product was purified by flash chromatography on silica gel (eluting mixture EtOAc 20% in n-Hexane).

General Conditions for the Direct Alkylation of 2(R)- and 14-Hydroxy-Micheliolide:

2(R)—OH-MCL or 14-OH-MCL (0.04 mmol) were dissolved in anhydrous DMF (1 mL) under a Ar atmosphere, then anhydrous $K_2CO_3$ (0.07 mmol) and a catalytic amount of KI were added, followed by benzyl bromide (0.04 mmol). The reaction was stirred at r.t. 12 h. The solvent was then evaporated and the residue taken up in $NaHCO_3$ saturated solution and extracted with EtOAc (3×). The collected organic phases ware dried over $Na_2SO_4$ and the solvent was removed in vacuo. The resulting crude product was purified by flash chromatography on silica gel (eluting mixture 50% EtOAc in n-Hexane).

General Conditions for the Azido Group Introduction into 2(R)- and 14-Hydroxy-Micheliolide Through Mitsunobu Reaction:

To a solution of 2(R)—OH-MCL or 14-OH-MCL (0.04 mmol), TPP (0.08 mmol) and DPPA (0.08 mmol) in anhydrous THF cooled at 0° C. under Ar atmosphere DEAD (0.08 mmol) was added dropwise. The reaction was warmed at r.t. and stirred 12 h. Disappearance of the starting material on TLC indicates the completion of the reaction. The reaction mixture was evaporated and the crude was purified by flash chromatography on silica gel (eluting mixture 40% EtOAc in n-Hexane).

General Conditions for the Mitsunobu Esterification of 2(R)-Hydroxy-Micheliolide:

To a solution of 2(R)—OH-MCL (0.04 mmol), TPP (0.16 mmol) and benzoic acid (0.17 mmol) in anhydrous THF cooled at 0° C. under Ar atmosphere DEAD (0.16 mmol) was added dropwise. The reaction was warmed at r.t. and stirred for 12 h. $NaHCO_3$ saturated solution was added to the reaction mixture and the aqueous phase was extracted with DCM (2×); the collected organic phases were dried over $Na_2SO_4$, concentrated in vacuo and the crude product was purified by flash chromatography on silica gel (eluting mixture EtOAc 20% in n-Hexane).

General Conditions for Carbamate Derivatization of 2(R)-Hydroxy-Micheliolide and 14-Hydroxy-Micheliolide:

To a solution of 2(R)—OH-MCL or 14-OH-MCL (0.05 mmol), and the appropriate isocyanate (0.07 mmol) in anhydrous DCM (2 mL) under Ar atmosphere DBTDL (dibuthyltin dilaurate) (20% mol) was added and the reaction was stirred at r.t. 12 h. The disappearance of the SM on TLC indicated the completion of the reaction. A saturated solution of $NaHCO_3$ was added and the aqueous phase was extracted with DCM (3×). The collected organic layers were dried over $Na_2SO_4$, concentrated in vacuo and the crude product was purified by flash chromatography on silica gel (eluting mixture EtOAc 50% in n-Hexane).

General Conditions for the Fluorination of 2(R)- and 14-Hydroxy-Micheliolide:DAST (0.22 mmol) was added dropwise to a solution of 2(R)—OH-MCL or 14-OH-MCL in anhydrous DCM (2 mL) under Ar atmosphere cooled at −78° C. The reaction was warmed to 0° C. and stirred until total disappearance of the SM was observed in TLC. The reaction was added of a saturated solution of $NaHCO_3$ and extracted with DCM (3×). The collected organic fractions were dried over $Na_2SO_4$, concentrated in vacuo and the crude product was purified by flash chromatography on silica gel (eluting mixture EtOAc 25% in n-Hexane).

SG-39: standard procedure was applied using 2(R)—OH-MCL (5 mg, 0.02 mmol), $Ag_2O$ (23 mg, 0.1 mmol) and MeI (7 mL, 0.1 mmol) to obtain the desired product as a colorless oil (0.6 mg, 12% yield); $^1H$ NMR (500 MHz, $CDCl_3$): δ=0.88-0.92 (m, 1H), 1.09 (s, 3H), 1.50 (s, 3H), 1.72-1.88 (m, 2H), 2.10-2.19 (m, 1H), 2.32-2.42 (m, 1H), 2.51 (d, 1H, J=8.5 Hz), 2.55-2.66 (m, 1H), 2.71 (t, 1H, J=9.0 Hz), 2.82 (d, 1H, J=8.0 Hz), 3.79 (s, 3H), 3.80-3.88 (m, 1H), 4.60 (s, 1H), 5.52 (d, 1H, J=3.0 Hz), 6.22 (d, 1H, J=3.0 Hz); $^{13}C$ NMR (126 MHz, $CDCl_3$) δ=19.9, 26.4, 27.2, 37.8, 49.5, 50.6, 58.2, 58.9, 79.7, 80.0, 85.3, 119.7, 125.8, 134.2, 140.9, 170.4; MS (ESI) calcd for $C_{16}H_{22}O_4$ m/z: 278.35; found: 301.2 $[M+Na]^+$, 579.5 $[2M+Na]^+$.

SG-40: standard procedure was applied using 14-OH-MCL (5 mg, 0.02 mmol), $Ag_2O$ (23 mg, 0.1 mmol) and MeI (7 mL, 0.1 mmol) to obtain the desired compound as a colorless oil (1.2 mg, 23% yield); $^1H$ NMR (500 MHz, $CDCl_3$): δ=1.25-1.38 (m, 4H), 1.54 (t, 1H, J=9.0 Hz), 1.79-1.85 (m, 3H), 2.10-2.16 (m, 2H), 2.30-2.35 (m, 1H), 2.52-2.62 (m, 2H), 2.70 (t, 1H, J=9.0 Hz), 2.82 (d, 1H, J=10.5 Hz), 3.30 (s, 3H), 3.85 (s, 2H), 5.52 (d, 1H, J=3.0 Hz), 6.22 (d, 1H, J=3.0 Hz); $^{13}C$ NMR (126 MHz, $CDCl_3$) δ=22.8, 25.7, 29.7, 30.6, 38.3, 50.2, 57.9, 58.8, 76.2, 80.3, 84.2, 119.7, 132.2, 137.9, 139.1, 169.9; MS (ESI) calcd for $C_{16}H_{22}O_4$ m/z: 278.35; found: 301.3 $[M+Na]^+$, 317.2 $[M+K]^+$, 579.3 $[2M+Na]^+$.

SG-41: standard procedure was applied using 2(R)—OH-MCL (30 mg, 0.11 mmol), $CrO_3$ (90 mg, 0.9 mmol) in $H_2O$ (105 μL) and conc. $H_2SO_4$ (30 μL) to obtain the desired product as a colorless oil (7 mg, 24% yield); $^1H$ NMR (500 MHz, $CDCl_3$): C=1.42-1.50 (m, 1H), 1.61 (s, 3H), 2.03-2.17 (m, 2H), 2.18 (s, 3H), 2.28-2.37 (m, 1H), 2.49 (br s, 1H), 2.52-2.64 (m, 1H), 2.70 (s, 1H, J=5.5 Hz), 2.85-2.97 (m, 1H), 3.02 (dd, 1H, $J_1$=10.0 Hz, $J_2$=2.5 Hz), 4.43 (t, 1H, J=11.0 Hz), 5.54 (d, 1H, J=3.0 Hz), 6.26 (d, 1H, J=3.0 Hz); $^{13}C$ NMR (126 MHz, $CDCl_3$) δ 20.4, 24.6, 25.8, 35.4, 48.5, 49.8, 71.8, 77.3, 82.5, 119.6, 126.3, 138.3, 163.5, 170.2, 207.0; MS (ESI) calcd for $C_{15}H_{18}O_4$ m/z: 262.31; found: 263.4 [M+H]$^+$, 285.3 [M+Na]$^+$, 547.2 [2M+Na]$^+$.

SG-42: standard procedure was applied using 2(R)—OH-MCL (30 mg, 0.11 mmol) and p-toluene-sulfonic acid (19 mg, 0.22 mmol) to obtain the desired product as a yellow solid (6 mg, 32% yield); $^1$H NMR (500 MHz, CDCl$_3$): δ=1.34-1.48 (m, 1H), 1.39 (s, 3H), 1.93 (s, 3H), 2.11 (t, 1H, J=14.0 Hz), 2.32-2.40 (m, 2H), 2.41 (br s, 1H), 2.68-2.76 (m, 2H), 2.84 (t, 1H, J=8.5 Hz), 4.15 (t, 1H, J=9.5 Hz), 5.55 (d, 1H, J=6.5 Hz), 5.92 (s, 1H), 6.25 (d, 1H, J=3.5 Hz); $^{13}$C NMR (126 MHz, CDCl$_3$) δ 20.1, 21.6, 25.8, 35.4, 42.9, 52.8, 69.8, 79.5, 119.8, 123.3, 124.6, 128.4, 139.5, 160.2, 170.6; MS (ESI) calcd for $C_{15}H_{18}O_3$ m/z: 246.31; found: 247.3 [M+H]$^+$, 263.3 [M+Na]$^+$, 285.3 [M+K]$^+$, 493.3 [2M+H]$^+$, 515.3 [2M+Na]$^+$.

SG-43: standard procedure was applied using 2(R)—OH-MCL (10 mg, 0.04 mmol), $K_2CO_3$ (11 mg, 0.07 mmol), a catalytic amount of KI and benzyl bromide (5 μL, 0.04 mmol) to obtain the desired product as a colorless oil (4 mg, 30% yield). $^1$H NMR (500 MHz, CDCl$_3$): C=1.23 (s, 3H), 1.26-1.48 (m, 1H), 1.61 (s, 3H), 2.00 (t, 1H, J=9.5 Hz), 2.15 (d, 1H, J=10.5 Hz), 2.17-2.42 (m, 3H), 2.57 (t, 1H, J=9.5 Hz), 2.74 (t, 1H, J=8.0 Hz), 3.08 (d, 1H, J=7.5 Hz), 3.85 (t, 1H, J=10.5 Hz), 4.68 (s, 2H), 5.02 (d, 1H, J=5.5 Hz), 5.76 (t, 1H, J=8.0 Hz), 6.25 (d, 1H, J=5.0 Hz), 7.42 (t, 2H, J=8.0 Hz), 7.61 (t, 1H, J=7.5 Hz), 7.71 (d, 2H, J=9.5 Hz); $^{13}$C NMR (126 MHz, CDCl$_3$) δ 22.5, 25.6, 29.2, 38.1, 50.3, 58.8, 62.6, 75.2, 80.3, 81.8, 83.7, 119.8, 124.3, 128.6 (2C), 129.2 (2C), 130.0, 133.1, 138.9, 140.4, 169.8; MS (ESI) calcd for $C_{22}H_{26}O_4$ m/z: 354.4; found: 377.5 [M+Na]$^+$, 393.3 [M+K]$^+$.

SG-44: standard procedure was applied using 14-OH-MCL (20 mg, 0.08 mmol), $K_2CO_3$ (22 mg, 0.14 mmol), a catalytic amount of KI and benzyl bromide (10 μL, 0.08 mmol) to obtain the desired compound as a colorless oil (10 mg, 38% yield). $^1$H NMR (500 MHz, CDCl$_3$): δ=1.35-1.37 (m, 1H), 1.36 (s, 3H), 1.82-1.90 (m, 2H), 2.18 (d, 1H, J=13.5 Hz), 2.29 (t, 1H, J=15 Hz), 2.39-2.50 (m, 2H), 2.60 (d, 1H, J=13 Hz), 2.62-2.74 (m, 2H), 2.86 (d, 1H, J=10.5 Hz), 3.85 (t, 1H, J=10.5 Hz), 4.05 (s, 2H), 4.50 (s, 2H), 5.52 (d, 1H, J=3.0 Hz), 6.23 (d, 1H, J=3.0 Hz), 7.38 (d, 2H, J=8.0 Hz), 7.48 (t, 2H, J=7.5 Hz), 7.52 (t, 1H, J=7.0 Hz); $^{13}$C NMR (126 MHz, CDCl$_3$) δ 22.8, 25.7, 29.3, 30.8, 38.2, 50.0, 58.9, 67.6, 69.2, 80.1, 83.6, 119.7, 127.5, 128.4, 129.5, 133.1, 137.2, 138.5, 140.0, 169.4; MS (ESI) calcd for $C_{22}H_{26}O_4$ m/z: 354.4; found: 393.3 [M+K]$^+$.

SG-45: standard procedure was applied using 2(R)—OH-MCL (10 mg, 0.04 mmol), $K_2CO_3$ (11 mg, 0.07 mmol), a catalytic amount of KI and 2,4-di-fluorobenzyl bromide (6 μL, 0.04 mmol) to obtain the desired product as a colorless oil (6 mg, 46% yield). $^1$H NMR (500 MHz, CDCl$_3$): δ=1.38 (s, 3H), 1.41-1.45 (m, 1H), 1.74 (s, 3H), 2.06 (dd, 1H, $J_1$=8.0 Hz, $J_2$=3.0 Hz), 2.15 (d, 1H, J=10.0 Hz), 2.34 (s, 2H), 2.63 (dd, 2H, $J_1$=8.0 Hz, $J_2$=3.5 Hz), 2.74 (t, 1H, J=10.0 Hz), 3.06 (d, 1H, J=9.5 Hz), 3.85 (t, 1H, J=9.8 Hz), 4.60 (s, 2H), 5.55 (d, 1H, J=3.5 Hz), 5.88 (t, 1H, J=7.0 Hz), 6.26 (d, 1H, J=3.5 Hz), 7.83 (d, 1H, J=8.0 Hz), 7.88 (d, 1H, J=8.0 Hz), 7.99 (s, 1H); $^{13}$C NMR (126 MHz, CDCl$_3$) δ 24.1, 24.2, 25.8, 35.6, 45.1, 48.2, 58.1, 65.6, 75.7, 83.8, 86.2, 120.4, 124.0 (d, J=21.4 Hz), 128.7, 129.6 (d, J=37.8 Hz), 130.2, 130.4, 133.3 (d, J=34.2 Hz), 134.6, 138.1, 139.6, 169.2; $^{19}$F NMR (376 MHz, CDCl$_3$): δ −0.86, 2.90; MS (ESI) calcd for $C_{24}H_{24}F_2O_4$ m/z: 390.43; found: 413.4 [M+Na]$^+$, 803.4 [2M+Na]$^+$.

SG-46: standard procedure was applied using 14-OH-MCL (20 mg, 0.08 mmol), $K_2CO_3$ (22 mg, 0.14 mmol), a catalytic amount of KI and 2,4-di-fluorobenzyl bromide (13 μL, 0.08 mmol) to obtain the desired compound as a colorless oil (15 mg, 53% yield). $^1$H NMR (500 MHz, CDCl$_3$): δ=1.28-1.36 (m, 4H), 1.84-1.36 (m, 2H), 2.16 (d, 1H, J=13.2 Hz), 2.27 (t, 1H, J=14.5 Hz), 2.39-2.50 (m, 1H), 2.53 (d, 1H, J=16.0 Hz), 2.63-2.73 (m, 3H), 2.85 (d, 1H, J=10.0 Hz), 3.83 (t, 1H, J=10.5 Hz), 4.46 (dd, 2H, $J_1$=15.0 Hz, $J_2$=8.0 Hz), 4.78 (s, 2H), 5.51 (d, 1H, J=1.5 Hz), 6.23 (d, 1H, J=2.0 Hz), 7.89 (s, 1H), 7.99 (s, 2H); $^{13}$C NMR (126 MHz, CDCl$_3$) δ 22.7, 25.6, 29.3, 31.3, 38.1, 49.8, 59.0, 64.3, 69.6, 80.0, 83.5, 86.2, 119.4, 123.5, 127.9, 128.2, 131.4, 132.7, 134.5, 138.2, 142.6, 169.2; $^{19}$F NMR (376 MHz, CDCl$_3$): δ −0.86, 2.72; MS (ESI) calcd for $C_{24}H_{24}F_2O_4$ m/z: 390.43; found: 413.4 [M+Na]$^+$, 803.4 [2M+Na]$^+$.

SG-47: standard procedure was applied using 2(R)—OH-MCL (10 mg, 0.04 mmol), $K_2CO_3$ (11 mg, 0.07 mmol), a catalytic amount of KI and 4-$CF_3$-benzyl bromide (7 μL, 0.04 mmol) to obtain the desired product as a colorless oil (4 mg, 25% yield). $^1$H NMR (500 MHz, CDCl$_3$): δ=1.35 (s, 3H), 1.38-1.48 (m, 1H), 1.70 (s, 3H), 2.01 (dd, 1H, $J_1$=12.5 Hz, $J_2$=4.5 Hz), 2.18 (d, 1H, J=11.5 Hz), 2.34-2.42 (m, 3H), 2.60 (t, 1H, J=8.0 Hz), 2.78 (t, 1H, J=9.5 Hz), 3.11 (d, 1H, J=8.0 Hz), 3.86 (t, 1H, J=10.0 Hz), 4.61 (s, 2H), 5.56 (d, 1H, J=2.5 Hz), 5.84 (t, 1H, J=7.5 Hz), 6.27 (d, 1H, J=3.0 Hz), 7.70 (d, 2H, J=8.0 Hz), 8.14 (d, 2H, J=8.0 Hz); $^{13}$C NMR (126 MHz, CDCl$_3$) δ 24.1, 24.2, 25.7, 35.7, 45.5, 48.5, 58.2, 74.5, 80.2, 82.8, 83.9, 120.3, 125.4, 130.0 (4C), 130.8, 132.6 (d, J=113.4 Hz), 134.6 (d, J=32.3 Hz), 138.2, 139.1, 169.3; $^{19}$F NMR (376 MHz, CDCl$_3$): δ −0.72; MS (ESI) calcd for $C_{23}H_{25}F_3O_4$ m/z: 424.44; found: 445.3 [M+Na]$^+$.

SG-48: standard procedure was applied using 14-OH-MCL (20 mg, 0.08 mmol), $K_2CO_3$ (22 mg, 0.14 mmol), a catalytic amount of KI and 4-$CF_3$-benzyl bromide (14 μL, 0.08 mmol) to obtain the desired compound as a colorless oil (10 mg, 41% yield). $^1$H NMR (500 MHz, CDCl$_3$): δ=1.32-1.39 (m, 4H), 1.83-1.90 (m, 2H), 2.19 (d, 1H, J=13.5 Hz), 2.27 (t, 1H, J=13.5 Hz), 2.45 (t, 1H, J=4.0 Hz), 2.58 (d, 1H, J=16.5 Hz), 2.68-2.75 (m, 3H), 2.86 (d, 1H, J=10.5 Hz), 3.87 (t, 1H, J=10.5 Hz), 4.68 (s, 2H), 5.01 (s, 2H), 5.51 (d, 1H, J=2.5 Hz), 6.22 (d, 1H, J=3.0 Hz), 7.71 (d, 2H, J=8.0 Hz), 8.14 (d, 2H, J=8.0 Hz); $^{13}$C NMR (126 MHz, CDCl$_3$) δ 22.8, 25.4, 29.4, 30.8, 38.2, 50.0, 59.0, 68.2, 71.2, 80.1, 83.5, 119.7, 125.4 (t, J=97.5 Hz), 129.5 (2C), 130.0 (2C), 134.4 (t, J=102.4 Hz), 138.4 (2C), 140.6 (2C), 169.3; $^{19}$F NMR (376 MHz, CDCl$_3$): δ −0.73; MS (ESI) calcd for $C_{23}H_{25}F_3O_4$ m/z: 424.44; found: 445.3 [M+Na]$^+$.

SG-49: standard procedure was applied using 2(R)—OH-MCL (10 mg, 0.04 mmol), TPP (20 mg, 0.08 mmol), DPPA (16 μL, 0.08 mmol) and DEAD (12 μL, 0.08 mmol) to obtain the desired product as a colorless oil (2 mg, 13% yield). $^1$H NMR (500 MHz, CDCl$_3$): δ=1.30-1.38 (m, 4H), 1.82-1.70 (m, 2H), 2.18 (d, 1H, J=9.5 Hz), 2.27-2.41 (m, 2H), 2.48 (d, 1H, J=8.5 Hz), 2.54 (dd, 1H, $J_1$=18.0 Hz, $J_2$=4.2 Hz), 2.71 (t, 1H, J=9.5 Hz), 2.85 (d, 1H, J=10.0 Hz), 3.80-3.95 (m, 2H), 5.53 (d, 1H, J=3.0 Hz), 5.22 (t, 1H, J=7.5 Hz), 6.22 (d, 1H, J=5.0 Hz); $^{13}$C NMR (126 MHz, CDCl$_3$) δ 23.5, 29.7, 32.1, 35.7, 51.8, 56.1, 59.8, 65.5, 80.0, 82.6, 121.8, 125.3, 138.8, 139.8, 169.3; MS (ESI) calcd for $C_{15}H_{19}N_3O_4$ m/z: 289.34; found: 290.2 [M+H]$^+$, 312.2 [M+Na]$^+$, 328.2 [M+K]$^+$, 579.3 [2M+H]$^+$, 601.3 [2M+K]$^+$.

SG-50: standard procedure was applied using 14-OH-MCL (20 mg, 0.08 mmol), TPP (40 mg, 0.16 mmol), DPPA (32 μL, 0.16 mmol) and DEAD (24 μL, 0.16 mmol) to obtain the desired compound as a colorless oil (15 mg, 68% yield). $^1$H NMR (500 MHz, CDCl$_3$): δ=1.30-1.39 (m, 4H), 1.84-1.90 (m, 2H), 2.17 (d, 1H, J=8.5 Hz), 2.28-2.39 (m, 2H), 2.47 (d, 1H, J=12.5 Hz), 2.51-2.57 (m, 1H), 2.73 (t, 1H, J=7.5 Hz), 2.86 (d, 1H, J=8.0 Hz), 3.82-3.89 (m, 2H), 4.21 (q, 1H, J=8.0 Hz), 5.51 (d, 1H, J=3.0 Hz), 6.23 (d, 1H, J=3.0 Hz); $^{13}$C NMR (126 MHz, CDCl$_3$) δ 22.6, 25.5, 29.7, 32.1, 38.1, 49.8, 56.1, 58.8, 80.0, 83.6, 119.8, 129.3, 138.3, 140.1, 169.3; MS (ESI) calcd for C$_{15}$H$_{19}$N$_3$O$_4$ m/z: 289.34; found: 290.2 [M+H]$^+$, 312.2 [M+Na]$^+$, 328.2 [M+K]$^+$, 579.3 [2M+H]$^+$, 601.3 [2M+K]$^+$.

SG-51: standard procedure was applied using 2(R)—OH-MCL MCL (10 mg, 0.04 mmol), TPP (40 mg, 0.16 mmol) benzoic acid (19 μL, 0.17 mmol) and DEAD (24 μL, 0.16 mmol) to obtain the desired product as a colorless oil (10 mg, 36% yield). $^1$H NMR (500 MHz, CDCl$_3$): δ=1.21 (s, 3H), 1.30-1.48 (m, 1H), 1.70 (s, 3H), 2.00 (dd, 1H, J$_1$=9.5 Hz, J$_2$=3.0 Hz), 2.18 (d, 1H, J=10.5 Hz), 2.34-2.42 (m, 3H), 2.60 (t, 1H, J=7.5 Hz), 2.78 (t, 1H, J=7.0 Hz), 3.10 (d, 1H, J=4.5 Hz), 3.85 (t, 1H, J=10.5 Hz), 5.51 (d, 1H, J=3.0 Hz), 5.84 (t, 1H, J=7.5 Hz), 6.23 (d, 1H, J=3.0 Hz), 7.45 (t, 2H, J=8.0 Hz), 7.57 (t, 1H, J=7.5 Hz), 8.03 (d, 2H, J=7.5 Hz); $^{13}$C NMR (126 MHz, CDCl$_3$) δ 22.8, 25.4, 25.7, 38.2, 45.5, 50.0, 58.9, 74.5, 83.6, 119.7, 128.4 (2C), 129.5 (2C), 130.0, 133.1, 138.5 (2C), 140.0 (2C), 166.5, 169.4; MS (ESI) calcd for C$_{22}$H$_{24}$O$_5$ m/z: 368.43; found: 391.3 [M+Na]$^+$, 759.3 [2M+Na]$^+$.

SG-56: standard procedure was applied using 2(R)—OH-MCL MCL (12 mg, 0.05 mmol), phenyl isocyanate (8 μL, 0.07 mmol) and DBTDL (20% mol) to obtain the desired product as a white solid (10 mg, 86% yield). $^1$H NMR (500 MHz, CDCl$_3$): δ=1.25-1.34 (m, 4H), 1.77 (s, 3H), 2.00 (dd, 1H, J$_1$=12.5, J$_2$=4.0 Hz), 2.15 (d, 1H, J=12.0 Hz), 2.32-2.35 (m, 3H), 2.50 (dd, 1H, J$_1$=12.5 Hz, J$_2$=5.0 Hz), 2.73 (t, 1H, J=10.0 Hz), 3.02 (d, 1H, J=9.0 Hz), 3.83 (t, 1H, J=10.0 Hz), 5.55 (d, 1H, J=3.0 Hz), 5.64 (t, 1H, J=7.5 Hz), 6.26 (d, 1H, J=3.0 Hz), 6.66 (s, 1H, NH), 7.06 (t, 1H, J=7.0 Hz), 7.30 (t, 2H, J=7.5 Hz), 7.36-7.38 (m, 2H); $^{13}$C NMR (126 MHz, CDCl$_3$) δ 24.2, 24.7, 25.8, 29.3, 35.7, 45.7, 48.5, 58.2, 74.0, 83.9, 118.5, 120.2, 123.5, 129.1 (4C), 131.0, 137.7, 138.3, 139.0, 169.3; MS (ESI) calcd for C$_{22}$H$_{25}$NO$_5$ m/z: 383.44; found: 406.3 [M+Na]$^+$, 789.4 [2M+Na]$^+$.

SG-57: standard procedure was applied using 14-OH-MCL (24 mg, 0.10 mmol), phenyl isocyanate (16 μL, 0.14 mmol) and DBTDL (20% mol) to obtain the desired compound as a white solid (20 mg, 87% yield). $^1$H NMR (500 MHz, CDCl$_3$): δ=1.34 (s, 3H), 1.60-1.68 (m, 1H), 1.78-1.90 (m, 2H), 2.14-2.24 (m, 2H), 2.33 (d, 1H, J=7.5 Hz), 2.37-2.43 (m, 1H), 2.53 (d, 1H, J=16.0 Hz), 2.62-2.72 (m, 2H), 2.83 (d, 1H, J=10.5 Hz), 3.83 (t, 1H, J=10.5 Hz), 4.62 (s, 2H), 5.51 (s, 1H), 6.22 (d, 1H, J=3.5 Hz), 6.73 (br. s, 1H, NH), 7.06 (t, 1H, J=7.0 Hz), 7.30 (t, 2H, J=8.0 Hz), 7.36-7.39 (m, 2H); $^{13}$C NMR (126 MHz, CDCl$_3$) δ 22.6, 25.6, 29.2, 30.8, 38.2, 50.0, 58.9, 67.9, 80.1, 83.6, 118.6, 119.7, 123.6, 129.1 (4C), 130.0, 137.7, 138.4, 140.1, 169.5; MS (ESI) calcd for C$_{22}$H$_{25}$NO$_5$ m/z: 383.44; found: 406.3 [M+Na]$^+$, 789.4 [2M+Na]$^+$.

SG-58: standard procedure was applied using 2(R)—OH-MCL (12 mg, 0.05 mmol), 4-CF$_3$-phenyl isocyanate (10 μL, 0.07 mmol) and DBTDL (20% mol) to obtain the desired product as a white solid (14 mg, 90% yield). $^1$H NMR (500 MHz, CDCl$_3$): δ=1.29 (s, 3H), 1.45-1.51 (m, 1H), 1.77 (s, 3H), 2.01 (dd, 1H, J$_1$=13.0 Hz, J$_2$=4.5 Hz), 2.16 (dd, 1H, J$_1$=14.0 Hz, J$_2$=2.5 Hz), 2.35 (s, 2H), 2.51 (dd, 1H, J$_1$=13.0 Hz, J$_2$=5.0 Hz), 2.73 (t, 1H, J=9.0 Hz), 3.02 (d, 1H, J=10.0 Hz), 3.84 (t, 1H, J=10.0 Hz), 5.55 (d, 1H, J=3.0 Hz), 5.65 (t, 1H, J=7.5 Hz), 6.26 (d, 1H, J=3.5 Hz), 6.86 (s, 1H, NH), 7.50 (d, 2H, J=8.5 Hz), 7.56 (d, 2H, J=8.5 Hz); $^{13}$C NMR (126 MHz, CDCl$_3$) δ 24.1, 24.2, 25.7, 35.7, 45.7, 48.5, 58.2, 74.0, 83.8, 116.1, 118.0 (2C), 120.3, 123.0, 126.3 (2C), 130.8, 133.6, 138.2, 139.3, 140.9, 152.6, 169.2; $^{19}$F NMR (376 MHz, CDCl$_3$): δ 0.37; MS (ESI) calcd for C$_{23}$H$_{24}$F$_3$NO$_5$ m/z: 451.44; found: 475.4 [M+Na]$^+$, 925.6 [2M+Na]$^+$.

SG-59: standard procedure was applied using 14-OH-MCL (24 mg, 0.10 mmol), 4-CF$_3$-phenyl isocyanate (20 μL, 0.14 mmol) and DBTDL (20% mol) to obtain the desired compound as a white solid (29 mg, 93% yield). $^1$H NMR (500 MHz, CDCl$_3$): δ=1.32-1.39 (m, 4H), 1.83-1.90 (m, 2H), 215-2.25 (m, 2H), 2.36-2.41 (m, 1H), 2.52 (d, 1H, J=16.0 Hz), 2.63-2.72 (m, 2H), 2.83 (d, 1H, J=10.5 Hz), 3.83 (t, 1H, J=10.0 Hz), 4.64 (s, 2H), 5.51 (d, 1H, J=2.5 Hz), 6.22 (d, 1H, J=3.0 Hz), 6.94 (s, 1H, NH), 7.50 (d, 2H, J=8.5 Hz), 7.55 (d, 2H, J=8.5 Hz); $^{13}$C NMR (126 MHz, CDCl$_3$) δ 22.8, 25.6, 29.9, 30.9, 38.2, 49.9, 58.9, 68.2, 80.1, 83.6, 118.0 (2C), 119.8, 123.0, 125.3 (J=138.5 Hz), 126.3 (2C), 129.7, 138.4, 140.5, 140.9, 153.1, 169.4; $^{19}$F NMR (376 MHz, CDCl$_3$): δ 0.36; MS (ESI) calcd for C$_{23}$H$_{24}$F$_3$NO$_5$ m/z: 451.44; found: 475.4 [M+Na]$^+$, 925.6 [2M+Na]$^+$.

SG-60: standard procedure was applied using 2(R)—OH-MCL (10 mg, 0.04 mmol) and DAST (15 μL, 0.22 mmol) to obtain the desired product as a colorless oil (3 mg, 29% yield). $^1$H NMR (500 MHz, CDCl$_3$): δ=1.21-1.34 (m, 4H), 1.36-1.42 (m, 1H), 1.51-1.58 (m, 1H), 1.83 (dd, 1H, J$_1$=8.4 Hz, J$_2$=3.0 Hz), 1.95-2.06 (m, 1H), 2.24-2.31 (m, 3H), 2.39 (d, 1H, J=14.0 Hz), 2.61-2.70 (m, 2H), 2.937 (t, 1H, J=7.5 Hz), 5.11 (d, 1H, J=3.5 Hz), 5.55 (d, 1H, J=3.0 Hz), 6.25 (d, 1H, J=3.0 Hz); $^{13}$C NMR (126 MHz, CDCl$_3$) δ 22.8, 30.5, 31.5, 33.2 (d, J=54.3 Hz), 37.7, 46.5, 64.5 (d, J=60.2 Hz), 79.6, 82.4, 115.4, 121.1, 123.7, 124.0, 137.6, 168.2; $^{19}$F NMR (376 MHz, CDCl$_3$): δ −179. 6; MS (ESI) calcd for C$_{15}$H$_{19}$FO$_3$ m/z: 266.31; found: 289.2 [M+Na]$^+$, 555.3 [2M+Na]$^+$.

SG-61: standard procedure was applied using 14-OH-MCL (20 mg, 0.08 mmol) and DAST (30 μL, 0.44 mmol) to obtain the desired compound as a colorless oil (8 mg, 41% yield). $^1$H NMR (500 MHz, CDCl$_3$): δ=1.23-1.39 (m, 4H), 1.78-1.90 (m, 2H), 2.12-2.24 (m, 2H), 2.34 (br. s, 1H), 2.50-2.54 (m, 1H), 2.61 (d, 1H, J=13.5 Hz), 2.72 (t, 1H, J=9.5 Hz), 2.84 (t, 1H, J=9.0 Hz), 3.83 (t, 1H, J=9.0 Hz), 4.82 (d, 2H, J=47.5 Hz), 5.53 (d, 1H, J=3.0 Hz), 6.23 (d, 1H, J=3.0 Hz); $^{13}$C NMR (126 MHz, CDCl$_3$) δ 22.7, 25.6, 28.9, 29.8, 38.1, 49.9, 59.0, 79.9, 83.7 (d, J=54.5), 85.2, 119.8, 130.8, 138.4, 140.1, 147.3, 169.4; $^{19}$F NMR (376 MHz, CDCl$_3$): δ −217. 3; MS (ESI) calcd for C$_{15}$H$_{19}$FO$_3$ m/z: 266.31; found: 289.2 [M+Na]$^+$, 555.3 [2M+Na]$^+$.

5.9 Example 9: Synthesis of C2- and C14-Substituted Micheliolide Derivatives Via Successive Transformations of the Previously Inserted Functional Groups This example describes and demonstrates the preparation of compounds of general formula I and II according to the methods provided herein. In particular, it demonstrates how C2- and C14-substituted micheliolide analogs, coming from the enzymatic insertion of the hydroxyl group followed by chemical transformation of the same, could be further functionalized by reacting the functional groups already in place at the C2 or C14 site in micheliolide, thus gaining the access to a number of totally different micheliolide derivatives.

According to the present invention, the azido group (—N$_3$) can be further functionalized thanks to the enormous versatility of the same: the Huisgen reaction, the aza-Wittig reaction, the Sundberg cyclization, the Boyer and Boyer-Aubé rearrangements, the Curtius rearrangement, are only some of the organic reactions that can be performed starting from a primary or secondary azide. In particular, the present invention focus on the cycloaddition with an alkyne to generate a triazole derivative, or the direct reduction to amine (—NH$_2$) followed by amide formation through the coupling with a (hetero)aromatic or aliphatic carboxylic acid (FIGS. 5 and 6).

An established strategy for the synthesis of triazole-containing compounds is the cycloaddition of primary or secondary azides with alkynes. In the present invention, the chemoenzymatically-derived 2(S)-azido-micheliolide and 14-azido-micheliolide were reacted with (substituted)phenylacetylene in the presence of copper sulfate and sodium ascorbate to get SG-52 and SG-53 (FIGS. 5 and 6).

The Staudinger reaction is a well-known procedure for the direct reduction of azides to the corresponding amines, therefore capable of increasing the amount of applicable chemistry on azide-containing compounds. The chemoenzymatically-obtained 2(S)-azido-micheliolide and 14-azido-micheliolide can be reduced to the corresponding amine-containing derivatives in the presence of TPP to allow the formation of SG-54 and SG-55 (FIGS. 5 and 6), two excellent starting point for further functionalization of the micheliolide scaffolds.

A useful chemical transformation of amine-containing compounds is the coupling with a carboxylic acid, whereas the acidic function can contain an aliphatic, an aromatic or an aminoacidic group, in order to form an amide bond. The huge variety of coupling agents available nowadays allows for the reaction between a great number of different amines and carboxylic acids. The present invention provides the method for the obtainment of amide-containing micheliolide derivative SG-62, as illustrated in FIG. 6, starting from 14-amino-micheliolide, DCC and Et$_3$N.

General conditions for the cycloaddition of 2(S)-azido-micheliolide and 14-azido-micheliolide: to a solution of 2(S)-azido-MCL or 14-azido-MCL (0.04 mmol) and phenylacetylene (0.06 mmol) in a 1:1 DCM/H$_2$O mixture, copper sulfate pentahydrate (0.06 mmol) and sodium ascorbate (0.26 mmol) were added at r.t. The reaction was stirred for 12 h followed by extraction wit DCM (3×). The combined organic solvents were dried over Na$_2$SO$_4$, concentrated in vacuo and purified by flash chromatography on silica gel (eluting mixture EtOAc 100%).

General conditions for the Staudinger reduction of 2(S)-azido-micheliolide and 14-azido-micheliolide: a solution of 2(S)-azido-MCL or 14-azido-MCL (0.06 mmol) and TPP (0.06 mmol) in dry THF was stirred at r.t. for 6 h and then warmed up at 45° C. for 12 h. Disappearance of the starting material indicated the completion of the reaction. A saturated solution of NaHCO$_3$ was added to the reaction mixture and the aqueous phase was extracted with EtOAc (3×). The combined organic phases were dried over Na$_2$SO$_4$, evaporated in vacuo and the crude product was purified by flash chromatography on silica gel (eluting mixture MeOH 5% in EtOAc).

General conditions for the coupling reaction of 14-NH$_2$-micheliolide: DCC (0.06 mmol) and triethylamine (0.06 mmol) were added to a solution of 14-NH$_2$-MCL (0.03 mmol) in anhydrous DMF cooled to 0° C. and the mixture was stirred 1 h at 0° C.; a solution of benzyl alcohol (0.06 mmol) and triethylamine (0.06 mmol) in anhydrous DMF was added to the previous reaction mixture. The solution was allowed to warm up to r.t. and stirred 12 h. The reaction was directly concentrated in vacuo and the crude product was purified by flash chromatography on silica gel (eluting mixture EtOAc 20% in n-Hexane).

SG-52: standard procedure was applied using 2(S)-azido-MCL (10 mg, 0.04 mmol), phenylacetylene (6 μL, 0.06 mmol) in a 1:1 DCM/H$_2$O mixture (3 mL), copper sulfate pentahydrate (13 mg, 0.06 mmol) and sodium ascorbate (52 mg, 0.26 mmol) to obtain the desired product as a colorless oil (3 mg, 23% yield). $^1$H NMR (500 MHz, CDCl$_3$): δ=1.34-1.42 (m, 4H), 1.89-1.97 (m, 3H), 2.04-2.16 (m, 3H), 2.34 (d, 1H, J=11.0 Hz), 2.49-2.58 (m, 1H), 2.69 (t, 1H, J=4.5 Hz), 2.75-2.79 (m, 1H), 2.90 (d, 1H, J=10.5 Hz), 3.88 (t, 1H, J=8.0 Hz), 4.98 (d, 1H, J=3.0 Hz), 5.18 (d, 1H, J=7.0 Hz), 6.21 (d, 1H, J=3.5 Hz), 7.34-7.44 (m, 3H), 7.66 (s, 1H), 7.83 (d, 2H, J=7.5 Hz); $^{13}$C NMR (126 MHz, CDCl$_3$) δ 22.9, 29.9, 30.7, 38.7, 49.8, 55.0, 59.0, 59.9, 65.4, 80.1, 81.3, 119.1, 120.0, 125.7, 128.2, 128.3, 128.8, 128.9, 130.3, 138.0, 140.8, 148.2, 169.2; MS (ESI) calcd for C$_{23}$H$_{25}$N$_3$O$_3$ m/z: 391.47; found: 392.3 [M+H]$^+$, 414.3 [M+Na]$^+$, 430.3 [M+K]$^+$, 805.4 [2M+Na]$^+$.

SG-53: standard procedure was applied using 2(S)-azido-MCL (20 mg, 0.08 mmol), phenylacetylene (12 μL, 0.12 mmol) in a 1:1 DCM/H$_2$O mixture (3 mL), copper sulfate pentahydrate (26 mg, 0.12 mmol) and sodium ascorbate (104 mg, 0.52 mmol) to obtain the desired product as a colorless oil (10 mg, 37% yield). $^1$H NMR (500 MHz, CDCl$_3$): δ=1.36-1.42 (m, 4H), 1.89-1.97 (m, 2H), 2.03-2.14 (m, 3H), 2.35 (d, 1H, J=16.5 Hz), 2.50-2.58 (m, 1H), 2.67-2.77 (m, 2H), 2.92 (d, 1H, J=10.5 Hz), 3.85 (t, 1H, J=10.5 Hz), 4.93-5.02 (m, 2H), 5.48 (d, 1H, J=3.0 Hz), 6.21 (d, 1H, J=3.5 Hz), 7.34 (t, 1H, J=7.0 Hz), 7.43 (t, 2H, J=7.5 Hz), 7.65 (s, 1H), 7.83 (d, 2H, J=7.5 Hz); $^{13}$C NMR (126 MHz, CDCl$_3$) δ 21.0, 22.9, 29.9, 30.8, 38.1 47.1, 55.0, 59.0, 80.1, 83.3, 118.9, 120.0, 125.7 (2C), 128.2, 128.3, 128.9 (2C) 130.3, 138.0, 140.8, 148.1, 169.3; MS (ESI) calcd for C$_{23}$H$_{25}$N$_3$O$_3$ m/z: 391.47; found: 392.3 [M+H]$^+$, 414.3 [M+Na]$^+$, 430.3 [M+K]$^+$, 805.4 [2M+Na]$^+$.

SG-54: standard procedure was applied using 2(S)-azido-MCL (15 mg, 0.06 mmol) and TPP (12 mg, 0.06 mmol) to obtain the desired product as a colorless oil (2 mg, 14% yield); $^1$H NMR (500 MHz, CDCl$_3$): δ=1.16-1.29 (m, 4H), 1.44 (d, 2H, J=17.0 Hz), 1.602 (s, 1H), 1.75 (d, 2H, J=3.6 Hz), 1.90-1.93 (m, 3H), 2.12 (s, 1H), 2.17 (s, 1H), 2.55 (s, 1H), 2.58 (s, 1H), 3.00 (s, 1H), 3.24 (s, 1H), 5.03 (s, 1H), 5.62 (s, 1H), 6.28 (s, 1H); $^{13}$C NMR (126 MHz, CDCl$_3$) δ 18.4, 25.6, 28.3, 33.2, 48.5, 52.9, 55.0, 61.4, 78.9, 82.0, 120.6, 121.7, 127.8, 137.2, 170.5; MS (ESI) calcd for C$_{15}$H$_{21}$NO$_3$ m/z: 263.34; found: 264.4 [M+H]$^+$, 286.3 [M+Na]$^+$.

SG-55: standard procedure was applied using 14-azido-MCL (30 mg, 0.12 mmol) and TPP (24 mg, 0.12 mmol) to obtain the desired product as a colorless oil (8 mg, 23% yield). $^1$H NMR (500 MHz, CDCl$_3$): δ=110-1.22 (m, 2H), 1.27 (d, 1H, J=10.5 Hz), 1.43 (s, 1H), 1.51 (s, 1H), 1.60-1.66 (m, 1H), 1.68-2.00 (m, 2H), 2.13 (qd, 1H, J$_1$=12.8, J$_2$=11.1 Hz), 2.40-2.55 (m, 1H), 2.95-3.05 (m, 2H), 3.27-3.36 (m, 1H), 4.60 (t, 1H, J=10.5 Hz), 5.17-5.28 (m, 1H); $^{13}$C NMR (126 MHz, CDCl$_3$) δ 25.8, 27.0, 30.1, 32.4, 40.4, 47.9, 50.1, 58.4, 80.6, 81.7, 121.5, 137.2, 138.9, 140.0, 170.1; MS (ESI) calcd for C$_{15}$H$_{21}$NO$_3$ m/z: 263.34; found: 264.2 [M+H]$^+$, 286.3 [M+Na]$^+$, 302.3 [M+K]$^+$.

SG-62: standard procedure was applied using 14-amino MCL (10 mg, 0.04 mmol), DCC (6 mg, 0.06 mmol), triethylamine (8 μL, 0.12 mmol) and benzyl alcohol (4 mg, 0.06 mmol) to obtain the desired product as yellowish oil (2 mg, 18% yield). $^1$H NMR (500 MHz, CDCl$_3$): 0.80 (s, 1H), 1.20 (s, 3H), 1.30 (dt, 1H, J$_1$=12.5, J$_2$=7.0 Hz), 1.55 (dt, 1H, J$_1$=12.5, J$_2$ 6.9 Hz), 1.61-1.68 (m, 1H), 1.72-1.78 (m, 1H), 1.85-1.90 (m, 1H), 1.96 (dt, 1H, J$_1$=12.5, J$_2$=7.0 Hz), 2.17-2.22 (m, 2H), 2.24-2.30 (m, 1H), 2.50 (d, 1H, J=10.6 Hz), 2.95-3.04 (m, 1H), 3.85 (s, 2H), 4.70 (d, 1H, J=0.6 Hz), 5.55 (dd, 1H, J$_1$=1.9, J$_2$=0.8 Hz), 6.32 (dd, 1H, J$_1$=1.9, $J_2$=0.8 Hz), 7.37 (t, 2H, J=7.4 Hz), 7.44-7.48 (m, 1H), 7.68 (dd, 2H, $J_2$=7.5, $J_2$ 1.4 Hz); $^{13}$C NMR (126 MHz, CDCl$_3$) δ 25.8, 27.0, 31.2, 34.3, 37.5, 44.9, 49.9, 58.6, 80.2, 80.9, 120.6, 128.4 (2C), 131.5, 134.7 (2C), 139.4 (2C), 141.2, 143.0, 169.9, 170.7; MS (ESI) calcd for $C_{22}H_{25}NO_4$ m/z: 367.45; found: 390.2 [M+Na]$^+$, 757.5 [2M+Na]$^+$.

Figure 7:
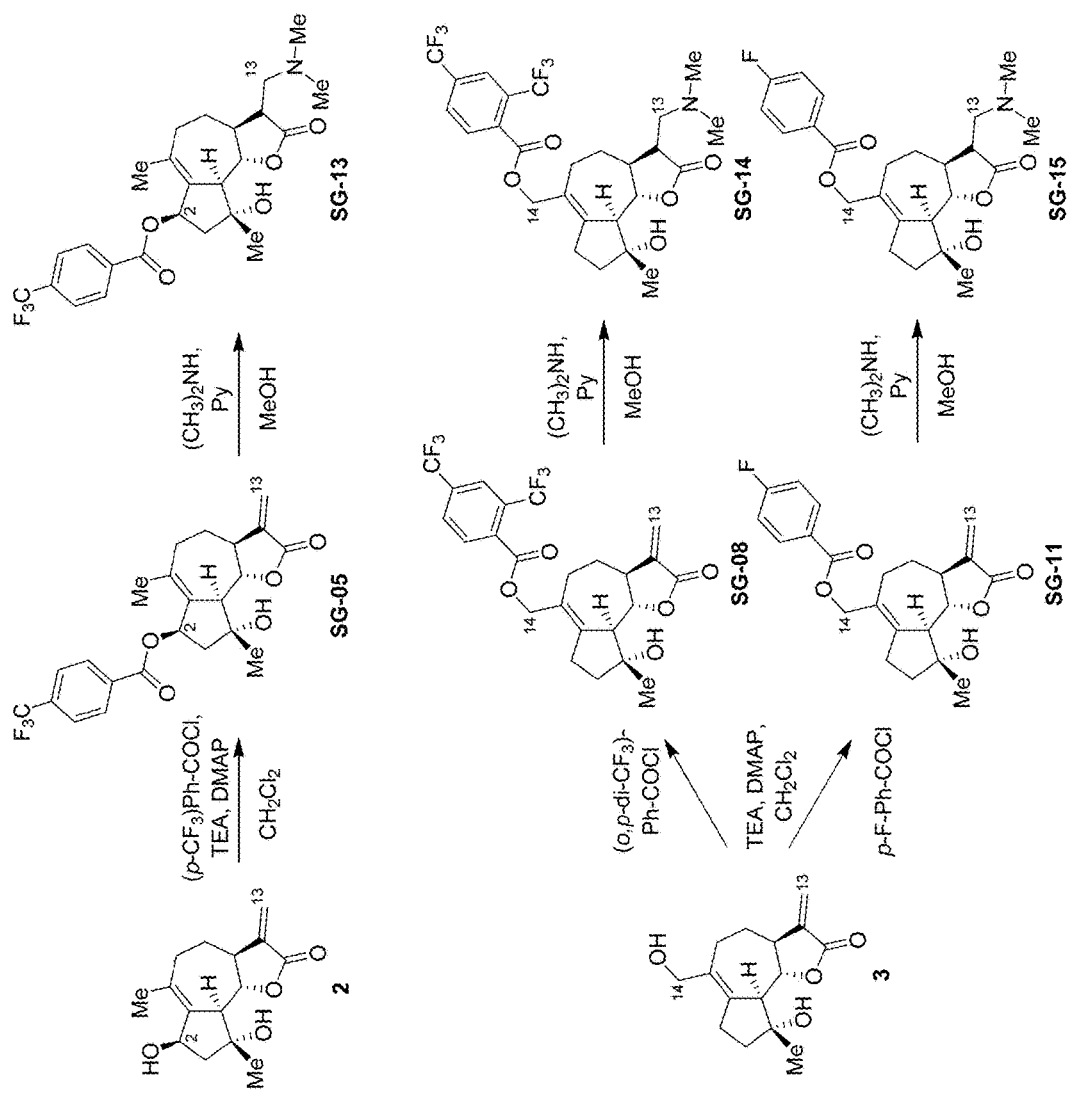
FIG. 7 depicts the synthesis of C2,C13-disubstituted and C13,C14-disubstituted micheliolide derivatives according to the methods provided herein.

5.10 Example 10: Synthesis of C2,C13- and C14,C13-Disubstituted Micheliolide Derivatives This example describes and demonstrates the preparation of compounds of general formula V according to the methods provided herein. In particular, it demonstrates how disubstituted micheliolide derivatives, such as 2,13-disubstituted micheliolide derivatives, can be prepared via chemoenzymatic functionalization of position C2 followed by chemical functionalization of position C13 (FIG. 7). Analogously, compounds of general formula VI can be prepared via chemoenzymatic functionalization of position C14 followed by similar procedures for C13 functionalization.

It is well known that the α-methylene-γ-lactone in parthenolide exhibits electrophilic reactivity and that the C13 site in this molecule can thus undergo Michael addition with nucleophilic reagents such as, for example, amine- or thiol-containing reagents. In particular, primary and secondary amines readily add to this site of the molecule (C13) under standard reaction conditions to yield C13-substituted amine-adducts (Guzman, Rossi et al. 2006; Nasim and Crooks 2008; Neelakantan, Nasim et al. 2009). Although this type of modification was not found to lead to significant improvements in the anticancer activity of parthenolide, it can be useful to improve its limited water-solubility (Guzman, Rossi et al. 2006; Nasim and Crooks 2008; Neelakantan, Nasim et al. 2009). Here is demonstrated that is possible to apply the same sort of chemistry to micheliolide analogues of general formula I and II, given the presence of a α-methylene-γ-lactone moiety (FIG. 7).

Since the chemoenzymatic functionalization at either the C2 or C14 site of micheliolide as described herein are remote with respect to the C13 site. Both C2- and C14-substituted micheliolide analogs can be further modified at position C13, e.g., via nucleophilic addition of an amine reagent to the α-methylene-γ-lactone moiety, to yield C2,C13- and C13,C14-substituted micheliolide analogs within the scope of the invention. An exemplary procedure for the preparation of doubly substituted micheliolide derivatives of this type is provided in FIG. 7. Because of the presence of basic amino group in these molecules, salt forms of these molecules can be then prepared via addition of an appropriate acid, which could be beneficial to further improve the water solubility and oral bioavailability of these compounds.

To illustrate this aspect of the invention, an improved C2-modified micheliolide derivative, SG-05, was made react with dimethylamine to yield the corresponding dimethylamino adduct SG-13, while two improved C14-modified micheliolide derivatives, SG-08 and SG-11, were reacted in the same way to yield the corresponding dimethylamino derivatives SG-14 and SG-15.

General Conditions for the Synthesis of Dimethylamino Derivative of 2(S)-Azido-Micheliolide and 14-Azido-Micheliolide:

To a solution of a compound of general formula I or II (0.07 mmol) in 10 mL of absolute EtOH under Ar atmosphere was added dimethylamine 2 M in THF (0.21 mmol). The reaction was allowed to stir until completion (ca. 12 hrs.). After removal of the solvent under reduced pressure, the dimethylamino-derivate product was isolated by silica gel flash chromatography (eluting mixture from 100% EtOAc to 1% MeOH in EtOAc).

SG-13: standard procedure was applied using SG-05 (6 mg, 0.014 mmol) and dimethylamine 2.0 M in MeOH (8 μL, 0.015 mmol) to obtain the desired product as a yellowish oil (7 mg, 99% yield). $^1$H NMR (500 MHz, CDCl$_3$): δ=1.33 (s, 3H), 1.38 (dd, 1H, J=11.0, 23.3 Hz), 1.68 (s, 3H), 1.98 (dd, 1H, J=8.7, 12.5 Hz), 2.13-2.25 (m, 1H), 2.27 (s, 6H), 2.36 (t, 1H, J=14.2 Hz), 2.43 (dt, 1H, J=5.6, 11.5 Hz), 2.58 (dd, 2H, J=7.8, 12.7 Hz), 2.63 (dd, 2H, J=6.5, 13.0 Hz), 2.75 (dd, 2H, J=4.9, 13.0 Hz), 3.02 (d, 1H, J=12.6 Hz), 3.87 (t, 1H, J=10.2 Hz), 5.83 (t, 1H, J=7.4 Hz), 7.70 (d, 2H, J=8.2 Hz), 8.13 (d, 2H, J=8.1 Hz); $^{13}$C NMR (126 MHz, CDCl$_3$) δ=24.03, 24.24, 27.20, 36.15, 44.64, 45.40, 45.96 (2C), 49.69, 58.01, 58.26, 74.58, 83.67, 114.68, 120.26, 124.92, 125.46, 129.92 (2C), 130.70, 133.23, 134.39, 139.61, 165.05, 176.57; $^{19}$F NMR (376 MHz, CDCl$_3$): δ=−0.44; MS (ESI) calcd for $C_{25}H_{30}F_3NO_5$ m/z: 481.51; found: 482.4 [M+H]$^+$.

SG-14: standard procedure was applied using SG-08 (16 mg, 0.032 mmol) and dimethylamine 2.0 M in MeOH (18 μL, 0.035 mmol) to obtain the desired product as a yellowish oil (17 mg, 99% yield). $^1$H NMR (500 MHz, CDCl$_3$): δ=1.20-1.30 (m, 1H), 1.33 (s, 3H), 1.77-1.90 (m, 2H), 2.08 (dd, 1H, J=11.1, 22.6 Hz), 2.17-2.24 (m, 2H), 2.27 (s, 6H), 2.44 (dd, 4H, J=5.1, 12.7 Hz), 2.59-2.68 (m, 2H), 2.71-2.78 (m, 2H), 3.85 (t, 1H, J=10.3 Hz), 4.81 (dd, 2H, J=11.5, 44.0 Hz), 7.89 (s, 2H), 7.99 (s, 1H); $^{13}$C NMR (126 MHz, CDCl$_3$) δ=22.82, 27.09, 29.33, 31.58, 38.08, 44.43, 45.87 (2C), 51.15, 57.86, 58.61, 69.45, 80.05, 83.04, 121.66, 123.90, 128.85, 129.28, 129.66, 130.99, 133.39, 133.76, 134.64, 141.60, 165.83, 176.66; $^{19}$F NMR (376 MHz, CDCl$_3$): δ=−0.46, 2.68; MS (ESI) calcd for $C_{26}H_{29}F_6NO_5$ m/z: 549.51; found: 550.2 [M+H]$^+$, 1099.3 [2M+H]$^+$, 1121.4 [2M+Na]$^+$.

SG-15: standard procedure was applied using SG-11 (5 mg, 0.013 mmol) and dimethylamine 2.0 M in MeOH (7 μL, 0.014 mmol) to obtain the desired product as a yellowish oil (5 mg, 99% yield). $^1$H NMR (500 MHz, CDCl$_3$): δ=1.18-1.32 (m, 1H), 1.34 (s, 3H), 1.78-1.92 (m, 3H), 2.10 (dd, 4H, J=9.3, 22.9 Hz), 2.15-2.29 (m, 4H), 2.41 (td, 2H, J=6.1, 11.7 Hz), 2.49 (dd, 1H, J=4.7, 18.6 Hz), 2.64 (ddd, 2H, J=7.5, 16.3, 19.4 Hz), 2.70-2.81 (m, 3H), 3.86 (t, 1H, J=10.3 Hz, 1H), 4.76 (s, 2H), 7.12 (t, 2H, J=8.6 Hz), 7.99-8.08 (m, 2H); $^{13}$C NMR (126 MHz, CDCl$_3$) δ=22.92, 27.21, 29.19, 29.82, 31.18, 38.28, 44.46, 46.04 (2C), 51.34, 58.09, 58.64, 67.72, 80.14, 83.30, 115.52, 115.69, 125.77, 130.32, 132.10 (2C), 132.29, 140.02, 165.64; $^{19}$F NMR (376 MHz, CDCl$_3$): δ=−43.03; MS (ESI) calcd for $C_{24}H_{30}FNO_5$ m/z: 431.50; found: 432.4 [M+H]$^+$, 863.5 [2M+H]$^+$, 885.5 [2M+Na]$^+$.

5.11 Example 11: Antileukemic Activity of the Micheliolide Derivatives

Figure 8:
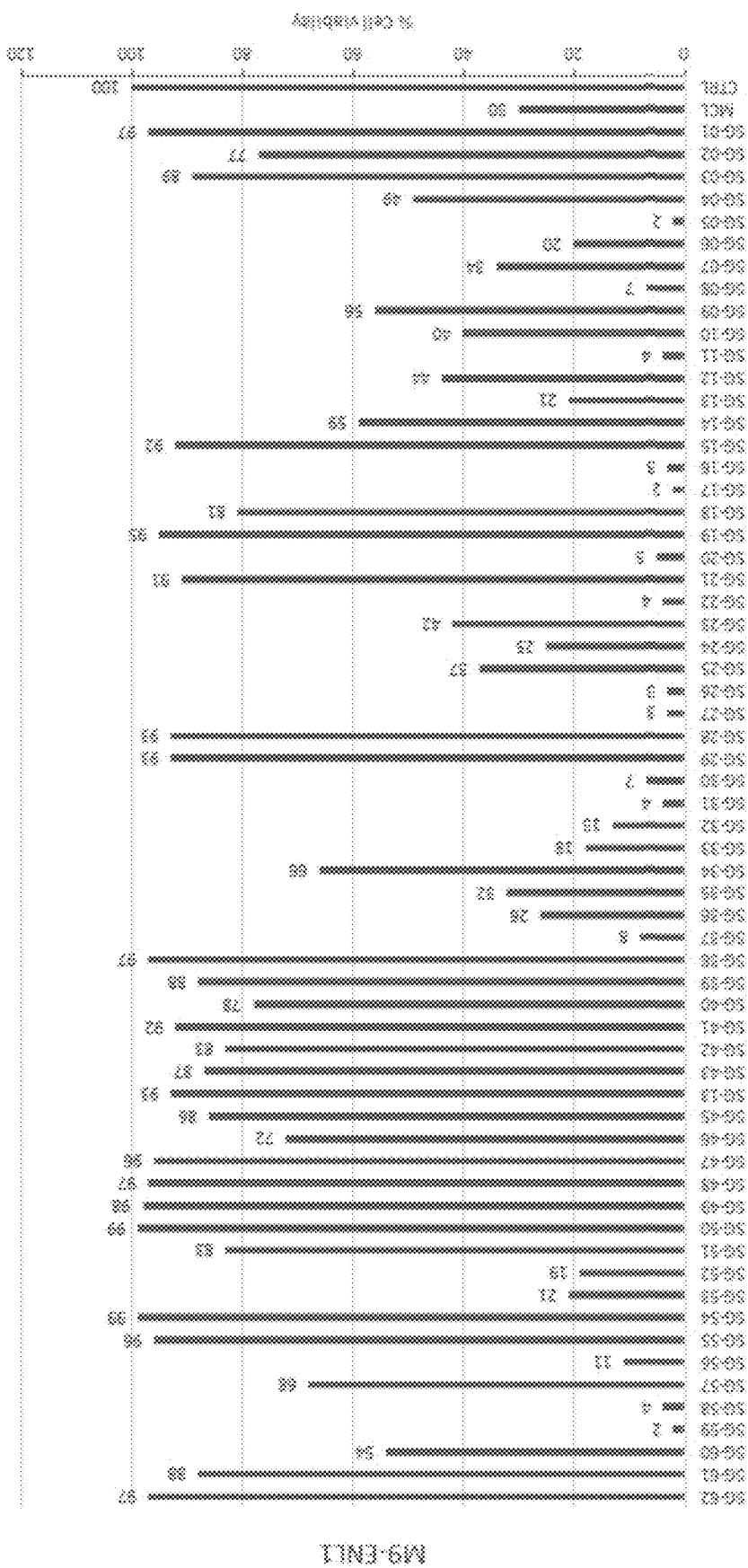
FIG. 8 depicts the antileukemic activity of MCL and MCL derivatives as measured based on reduction of cell viability of AML cells (M9-ENL1) upon incubation with the compound at 20 μM.
Figure 11:
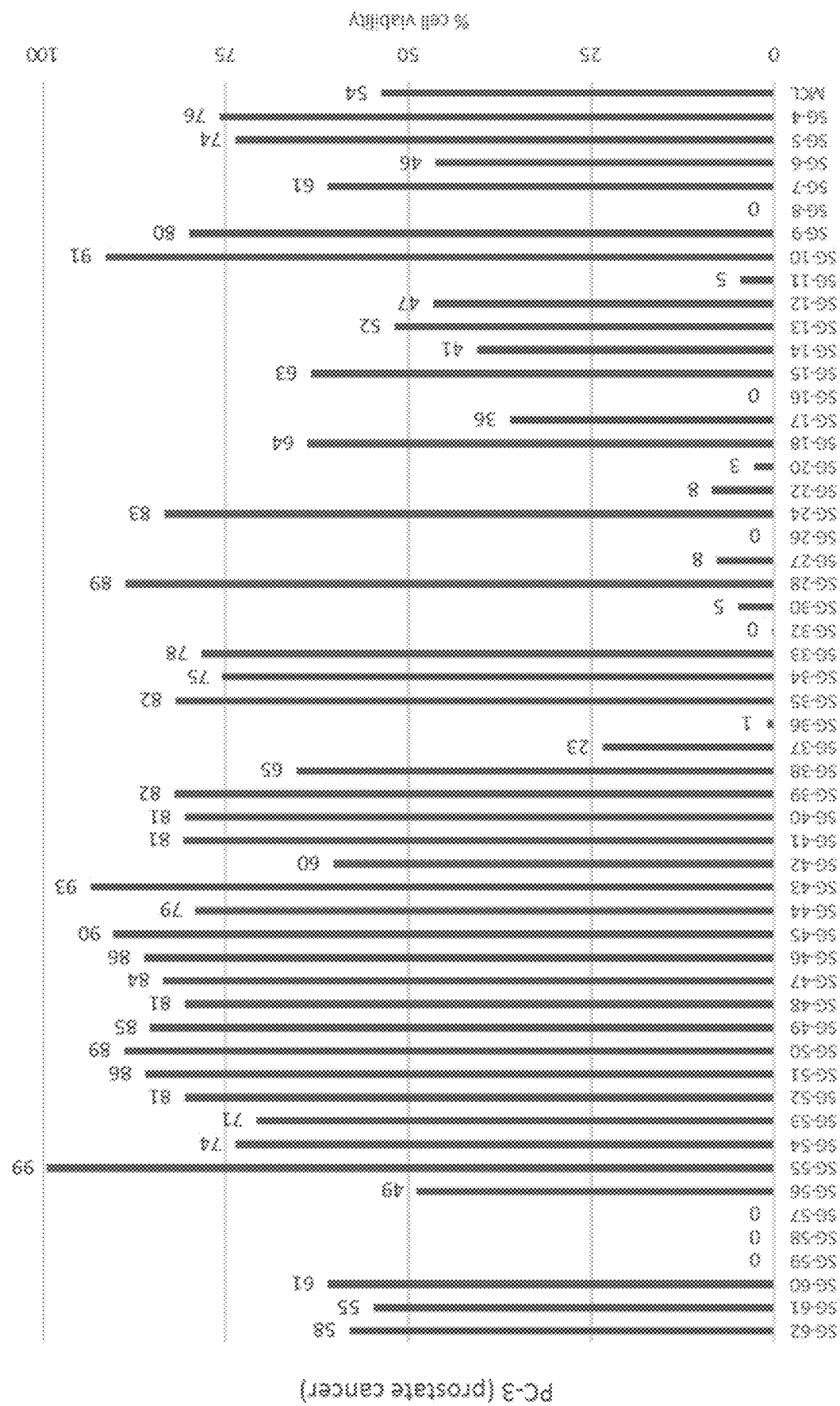
FIG. 11 depicts the cytotoxicity of MCL and MCL derivatives against prostate cancer cells (PC-3) as measured based on reduction of cell viability upon incubation with the compound at 20 μM.
Figure 12:
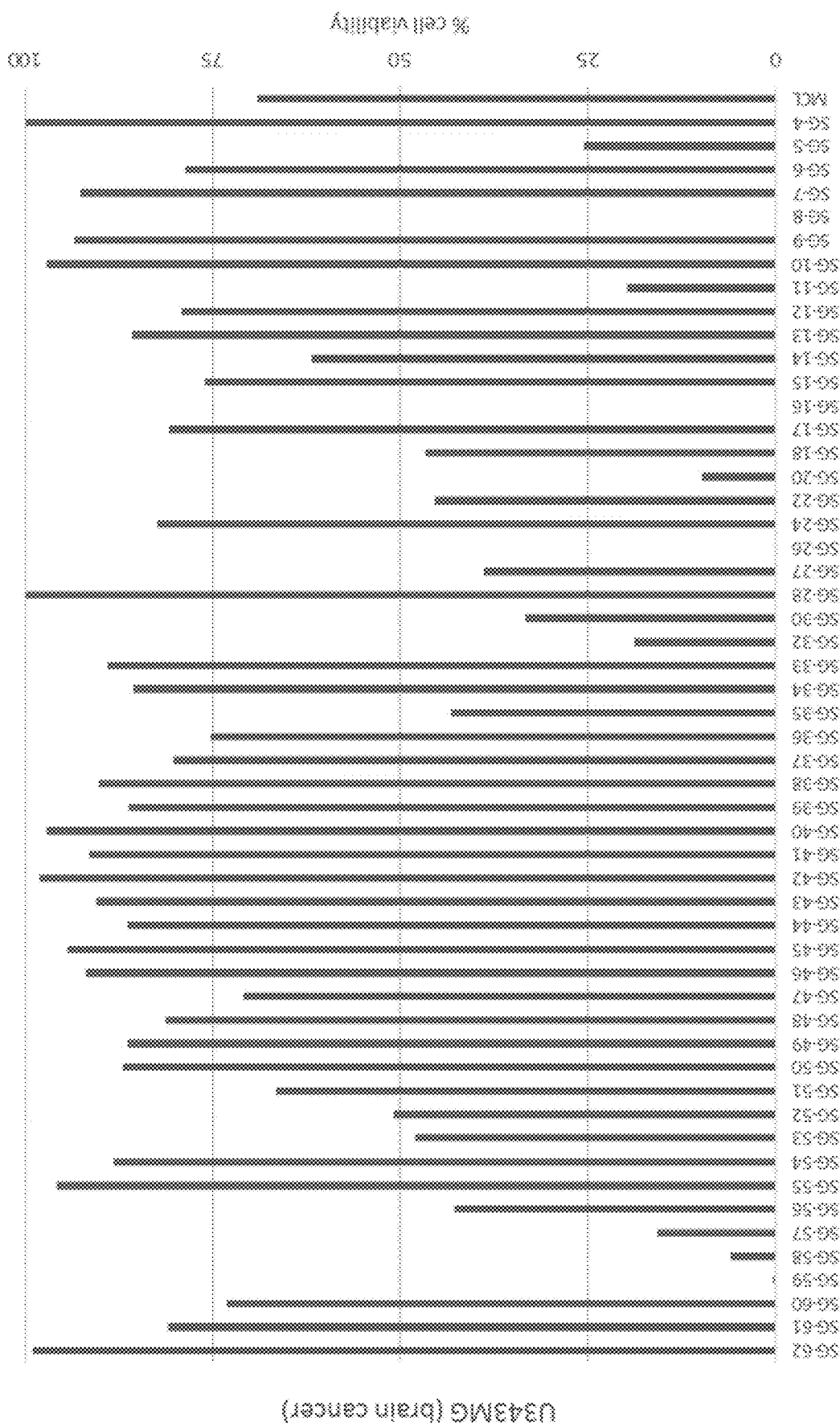
FIG. 12 depicts the cytotoxicity of MCL and MCL derivatives against brain cancer cells (U343MG) as measured based on reduction of cell viability upon incubation with the compound at 20 μM.
Figure 13:
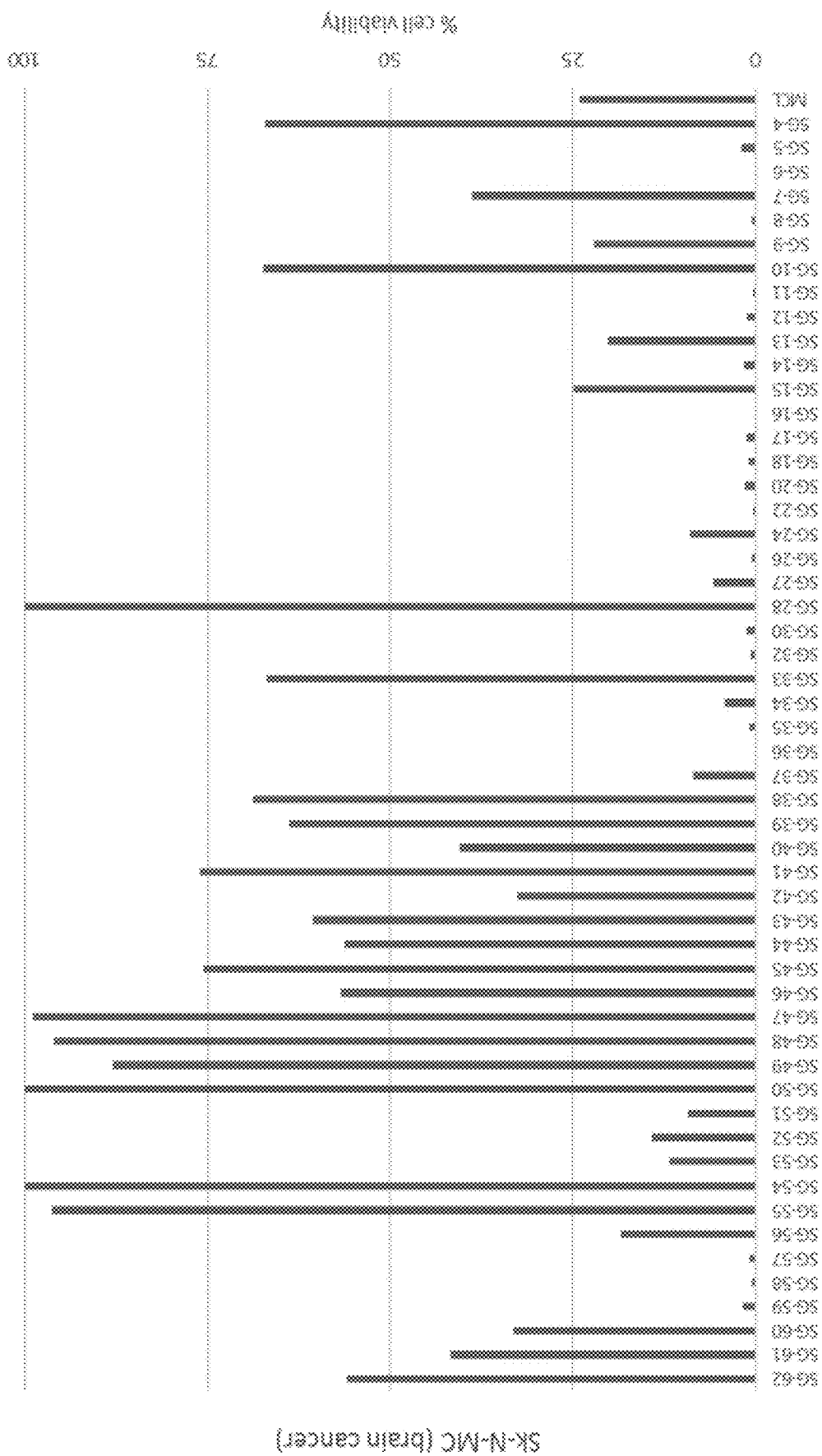
FIG. 13 depicts the cytotoxicity of MCL and MCL derivatives against neuroblastoma cells (SK-N-MC) as measured based on reduction of cell viability upon incubation with the compound at 20 μM.
Figure 14:
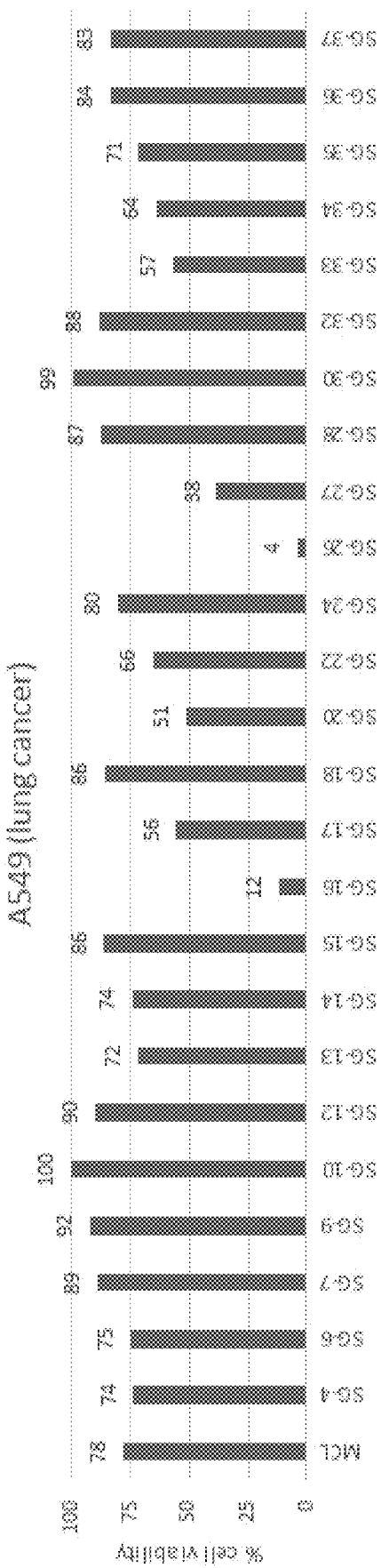
FIG. 14 depicts the cytotoxicity of MCL and MCL derivatives against lung cancer cells (A549) as measured based on reduction of cell viability upon incubation with the compound at 20 µM.
Figure 15:
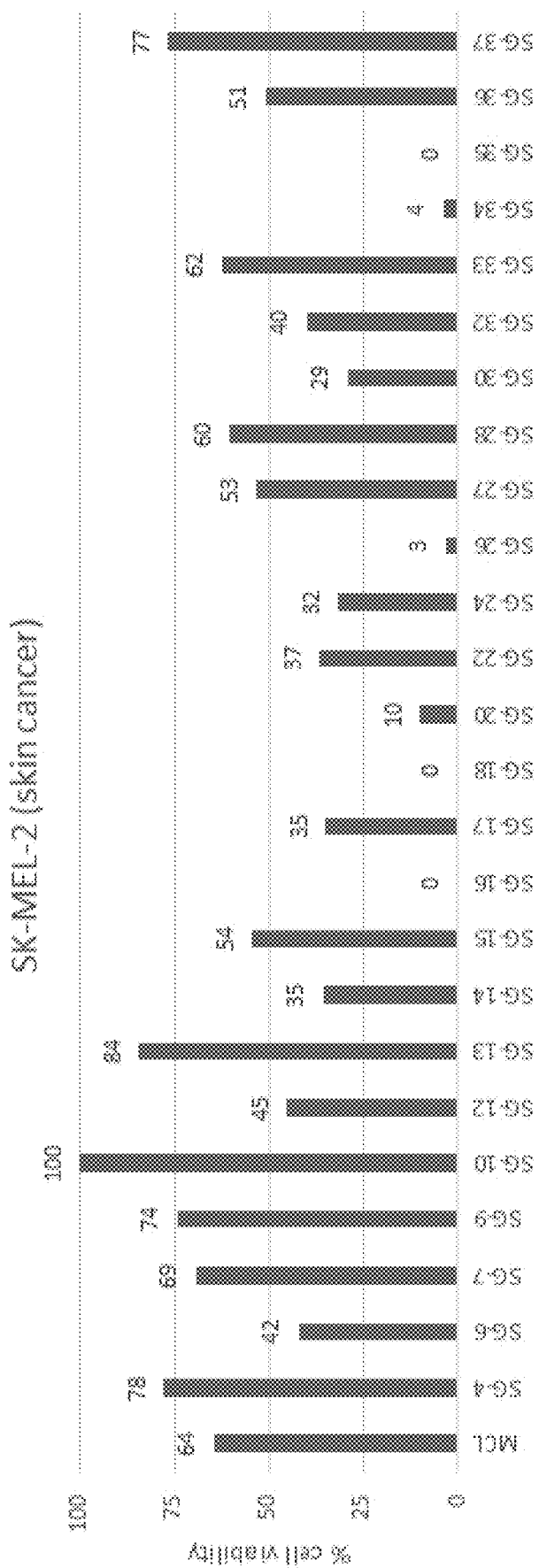
FIG. 15 depicts the cytotoxicity of MCL and MCL derivatives against skin cancer cells (SK-MEL-2) as measured based on reduction of cell viability upon incubation with the compound at 20 µM.
Figure 16:
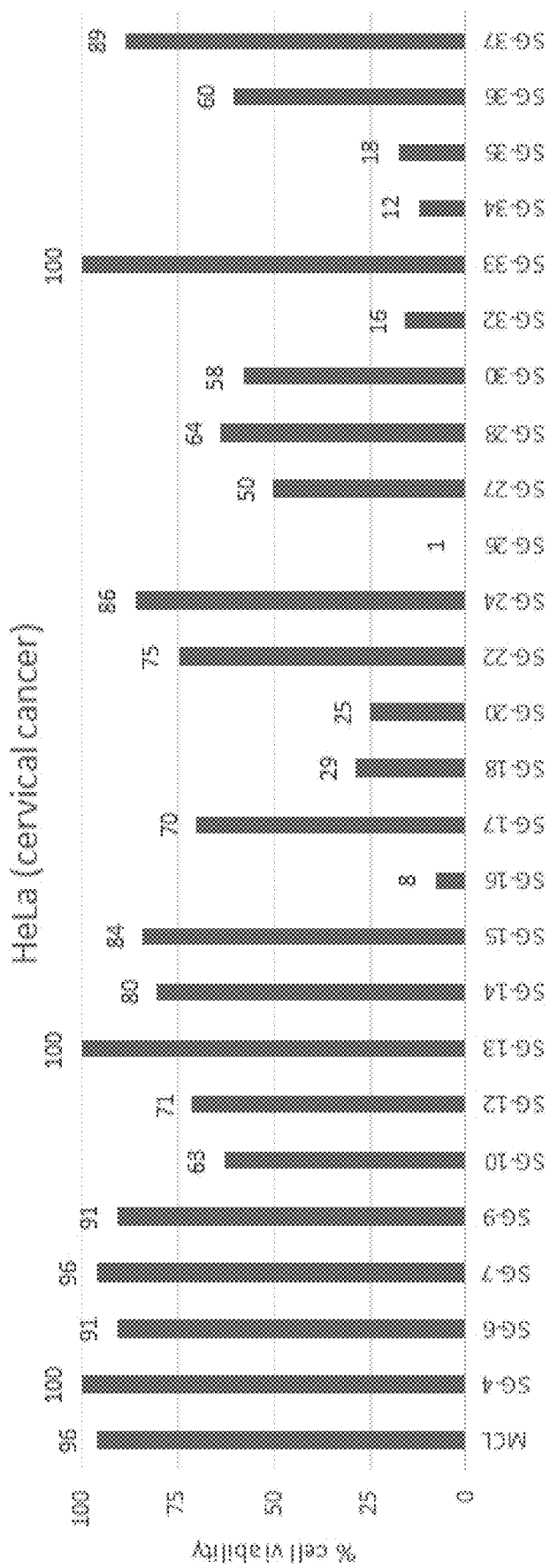
FIG. 16 depicts the cytotoxicity of MCL and MCL derivatives against cervical cancer cells (HeLa) as measured based on reduction of cell viability upon incubation with the compound at 20 µM.

The micheliolide derivatives described in the examples above have been found to possess potent activity against various types of leukemias and lymphomas, including acute myelogenous leukemia (AML). The antileukemic activity of the PTL analogs was evaluated using the leukemia cell line M9-ENL1. M9-ENL1 cells are derived from lineage depleted (Lin$^-$) human cord blood cells trasduced with a leukemogenic mixed-lineage leukemia (MLL)-eleven-nineteen leukemia (ENL) fusion gene (Barabe, F.; Kennedy, J. A.; Hope, K. J.; Dick, J. E. *Science* 2007, 316, 600.). Injected in NOD/SCID mice, M9-ENL1 cells develop a rapid and fatal pro-B cell acute lymphoblastic leukemia (ALL) disease (McDermott, S. P.; Eppert, K.; Notta, F.; Isaac, M.; Datti, A.; Al-Awar, R.; Wrana, J.; Minden, M. D.; Dick, J. E. *Blood* 2012, 119, 1200; Barabe, F.; Kennedy, J. A.; Hope, K. J.; Dick, J. E. *Science* 2007, 316, 600). These cells show an enrichment of embryonic and B-cell progenitor gene sets and exhibit the hallmarks and gene expression patters typical of leukemia stem cells (McDermott, S. P.; Eppert, K.; Notta, F.; Isaac, M.; Datti, A.; Al-Awar, R.; Wrana, J.; Minden, M. D.; Dick, J. E. *Blood* 2012, 119, 1200.). To measure the compound activity on M9-ENL1, cells were treated for 24 hours in the presence or in the absence of the MCL analog at 20 µM (FIG. 8), followed by measurement of cell viability using Annexin-V and 7-amino-actinomycin (7-AAD) stains. Half-maximal lethal concentration ($LC_{50}$) values were obtained from the resulting dose-dependent cell viability curves after normalization to untreated controls (FIG. 9). Using this assay, several of the novel MCL analogs disclosed herein were found to exhibit significantly improved antileukemic activity compared to the parent molecule MCL (FIGS. 8 and 9). In particular, MCL analogs such as SG-05, SG-52, SG-53, and SG-59 exhibited $LD_{50}$ values in the low micromolar range, that is nearly 7-fold lower than that of MCL. The most promising MCL analogs were selected for further testing against patient-derived primary AML specimens (FIG. 10). Across all the AML specimens tested, the MCL analogs showed improved cytotoxicity compared to the MCL, demonstrating the beneficial effect of the C2- or C14-functionalizations toward enhancing the antileukemic activity of this molecule.

Experimental Procedures.

Biological activity studies were performed using cell-based assays with human leukemia cells (M9-ENL1). Primary AML specimens were obtained with informed consent from volunteer donors. In some cases, cells were cryopreserved in freezing medium of Iscove modified Dulbecco medium (IMDM), 40% fetal bovine serum (FBS), and 10% dimethylsulfoxide (DMSO) or in CryoStor CS-10 (VWR, West Chester, Pa.). Cells were cultured in serum-free medium (SFM) 19 for 1 hour before the addition of parthenolide or its derivatives. Apoptosis assays were performed as described in (Guzman, Neering et al. 2001). Briefly, after 24 hours of treatment, cells were stained for the surface antibodies CD38-allophycocyanin (APC), CD34-PECy7, and CD123-phycoerythin (Becton Dickinson, San Jose, Calif.) for 15 minutes. Cells were washed in cold PBS and resuspended in 200 of annexin-V buffer (0.01 M HEPES/NaOH, 0.14 M NaCl, and 2.5 mM $CaCl_2$). Annexin-V-fluorescein isothiocyanate (FITC) and 7-aminoactinomycin (7-AAD; Molecular Probes, Eugene, Oreg.) were added, and the tubes were incubated at room temperature for 15 minutes then analyzed on a BD LSRII flow cytometer (BD Biosciences, San Jose, Calif.). Analyses for phenotypically described stem cell subpopulations were performed by gating $CD34^+/CD38^-$ populations. Viable cells were scored as Annexin-V negative/7-AAD negative. The percent viability data provided are normalized to untreated control specimens.

5.12 Example 12: Anticancer Activity of the Micheliolide Derivatives

The micheliolide derivatives described in the examples above have been found to possess potent activity against various types of human cancer cells, including prostate cancer (PC3), neuroblastoma (SK-N-MC), breast cancer (MDA-MB-231), lung cancer (A549), cervical cancer (HeLa), skin cancer (SK-MEL-2), and brain cancer cells (U343MG). The anticancer activity of the compounds was determined using a conventional MTT assay, which measures cell viability upon incubation of the cells with the compounds. Using this assay, many of the MCL analogs were found to exhibit significantly (2- to >10-fold) improved anticancer activity compared to MCL, as determined based on the higher reduction in cancer cell viability upon incubation with the compound at the fixed concentration of 20 µM (FIGS. 11-16). Notably, some of the MCL analogs were found to possess a broad anticancer activity profile, being highly active (>70-90% reduction in cell viability) against multiple cancer cell lines (e.g., SG-16). Other MCL analogs, on the other hand, show cancer type-specificity, being highly active only against a subset of the cancer cell lines tested (e.g., SG-35). Overall, these results demonstrate the importance of the C2- and C14-functionalizations for enhancing and modulating the anticancer activity of MCL and obtaining MCL analogs with more promising properties as therapeutic agents.

Experimental Procedures.

All cancer cell lines were maintained in a 37° C. humidified incubator with 5% $CO_2$. A549, MDA-MB-231, PC-3, SK-N-MC, HeLa, and SK-MEL-2 cells were cultured in DMEM medium (Gibco) supplemented with 10% FBS (Gibco) and 100 I.U./ml penicillin-streptomycin (Sigma). Adherent cells were dissociated using Accutase (Millipore). Adherent cells were seeded in a 96-well plate at a density of 500-10,000 cells per well in 90 µl complete DMEM media. Suspension cells were seeded in conical 96-well plates (Nunc) at a density of 30,000 cells per well in 90 ul of complete α-MEM media devoid of phenol red indicator. The plates were incubated in a humidified incubator for 15 hours prior to treatment. PTL analogs were prepared as concentrated stocks (10 mM) in DMSO and stored at −30° C. Prior to testing, the analogs were diluted into complete cell culture medium and the media was supplemented with sterile DMSO (10% of final volume). For the initial cytotoxicity screening, the compounds were added to the cells in 10 µl aliquots to give a final concentration of 10 µM parthenologs and 1% DMSO (n=5). Following a 24-hour incubation, the culture media from the adherent cell plates (e.g., HeLa, A549) was aspirated and replaced with 100 µl of 1 mg/ml Thiazolyl Blue Tetrazolium Bromide (MTT, Sigma) in complete culture medium devoid of phenol red. After incubation at 37° C. for 3 hours, the plates were centrifuged (4000 rpm, 5 minutes), the media was removed and 100 ul of DMSO was added to solubilize the formazan product. The resulting OD was measured at 550 nm using a multi-well plate reader (Tecan).

REFERENCES

Each reference listed below is hereby incorporated by reference herein in its entirety.

Anderson, K. N. and B. E. Bejcek (2008). J Pharmacol Sci 106(2): 318-320.

Baeuerle, P. A. and T. Henkel (1994). Annual Review of Immunology 12: 141-179.

Barnes, P. J. and I. M. Adcock (1997). Trends in Pharmacological Sciences 18(2): 46-50.

Barnes, P. J. and M. Larin (1997). New England Journal of Medicine 336(15): 1066-1071.

Bessho, Y., D. R. Hodgson, et al. (2002). Nat Biotechnol 20(7): 723-728.

Bonnet, D. and J. E. Dick (1997). Nat Med 3(7): 730-737.

Castaneda-Acosta, J., N. H. Fischer, et al. (1993). J Nat Prod 56(1): 90-98.
Cheng, G. and L. Xie (2011). Molecules 16(8): 6758-6768.
Cirino, P. C. and F. H. Amold (2003). Angew. Chem. Int. Ed. Engl. 42(28): 3299-3301.
Costello, R. T., F. Mallet, et al. (2000). Cancer Research 60(16): 4403-4411.
Cox, C. V., R. S. Evely, et al. (2004). Blood 104(9): 2919-2925.
Cox, G. G., J. J. Kulagowski, et al. (1992). Synlett(12): 975-976.
Dedkova, L. M., N. E. Fahmi, et al. (2003). Journal of the American Chemical Society 125(22): 6616-6617.
Estabrook, N. C., H. Chin-Sinex, et al. (2011). Free Radic Biol Med 51(12): 2249-2258.
Galal, A. M., A. R. S. Ibrahim, et al. (1999). Phytochemistry 51(6): 761-765.
Garcia-Pineres, A. J., V. Castro, et al. (2001). Journal of Biological Chemistry 276(43): 39713-39720.
Garcia-Pineres, A. J., M. T. Lindenmeyer, et al. (2004). Life Sci 75(7): 841-856.
Ghantous, A., H. Gali-Muhtasib, et al. (2010). Drug Discov Today 15(15-16): 668-678.
Gopal, Y. N., T. S. Arora, et al. (2007). Chem Biol 14(7): 813-823.
Gopal, Y. N., E. Chanchorn, et al. (2009). Mol Cancer Ther 8(3): 552-562.
Graham, S. M., H. G. Jorgensen, et al. (2002). Blood 99(1): 319-325.
Guan, Y. H., B. Gerhard, et al. (2003). Blood 101(8): 3142-3149.
Guzman, M. L., L. Kamischky, et al. (2004). Blood 104(11): 697a-697a.
Guzman, M. L., S. J. Neering, et al. (2001). Blood 98(8): 2301-2307.
Guzman, M. L., R. M. Rossi, et al. (2005). Blood 105(11): 4163-4169.
Guzman, M. L., R. M. Rossi, et al. (2006). Blood 108(11): 74a-74a.
Guzman, M. L., C. F. Swiderski, et al. (2002). Proc Natl Acad Sci USA 99(25): 16220-16225.
Han, C., F. J. Barrios, et al. (2009). J. Org. Chem. 74(18): 7176-7179.
Hehner, S. P., M. Heinrich, et al. (1998). J Biol Chem 273(3): 1288-1297.
Heptinstall, S., A. White, et al. (1985). Lancet 1(8437): 1071-1074.
Hirakawa, H. and T. Nagamune (2010). Chembiochem 11(11): 1517-1520.
Holcomb, B. K., M. T. Yip-Schneider, et al. (2012). J Gastrointest Surg 16(7): 1333-1340.
Holyoake, T., X. Y. Jiang, et al. (1999). Blood 94(6): 2056-2064.
Hwang, D., N. H. Fischer, et al. (1996). Biochem Biophys Res Commun 226(3): 810-818.
Hwang, D. R., C. W. Chang, et al. (2006). Bioorganic & Medicinal Chemistry 14(1): 83-91.
Idris, A. I., H. Libouban, et al. (2009). Mol Cancer Ther 8(8): 2339-2347.
Janecka, A., A. Wyrebska, et al. (2012). Drug Discov Today 17(11-12): 561-572.
Juliana, C., T. Fernandes-Alnemri, et al. (2010). J Biol Chem 285(13): 9792-9802.
Kawasaki, B. T., E. M. Hurt, et al. (2009). Prostate 69(8): 827-837.
Killmann, S. A. (1991). Baillieres Clin Haematol 4(3): 577-598.
Kim, I. H., S. W. Kim, et al. (2012). Exp Mol Med 44(7): 448-456.
Kim, J. H., L. Liu, et al. (2005). Cancer Res 65(14): 6312-6320.
Knight, D. W. (1995). Nat Prod Rep 12(3): 271-276.
Kourouklis, D., H. Murakami, et al. (2005). Methods 36(3): 239-244.
Kreuger, M. R., S. Grootjans, et al. (2012). Anticancer Drugs 23(9): 883-896.
Kwok, B. H., B. Koh, et al. (2001). Chem Biol 8(8): 759-766.
Landwehr, M., M. Carbone, et al. (2007). Chem. Biol. 14(3): 269-278.
Lapidot, T., C. Sirard, et al. (1994). Nature 367(6464): 645-648.
Lesiak, K., K. Koprowska, et al. (2010). Melanoma Res 20(1): 21-34.
Li, S. Y., L. M. Podust, et al. (2007). J. Am. Chem. Soc. 129(43): 12940-12941.
Li, Y., Y. Zhang, et al. (2012). Mol Med Rep 6(3): 477-482.
Liu, C. C. and P. G. Schultz (2010). Annu. Rev. Biochem. 79: 413-444.
Liu, Y., W. L. Lu, et al. (2008). J Control Release 129(1): 18-25.
Liu, Z., S. Liu, et al. (2009). J Pharmacol Exp Ther 329(2): 505-514.
Merfort, I. (2011). Current Drug Targets 12(11): 1560-1573.
Murakami, H., A. Ohta, et al. (2006). Nat Methods 3(5): 357-359.
Nakshatri, H., S. E. Rice, et al. (2004). Oncogene 23(44): 7330-7344.
Nasim, S. and P. A. Crooks (2008). Bioorg Med Chem Lett 18(14): 3870-3873.
Neelakantan, S., S. Nasim, et al. (2009). Bioorg. Med. Chem. Lett. 19(15): 4346-4349.
Neukirch, H., N. C. Kaneider, et al. (2003). Bioorg Med Chem 11(7): 1503-1510.
Neumann, H., K. Wang, et al. (2010). Nature 464(7287): 441-444.
Oka, D., K. Nishimura, et al. (2007). International Journal of Cancer 120(12): 2576-2581.
Otey, C. R., M. Landwehr, et al. (2006). PLoS Biol. 4(5): el 12.
Park, J. H., L. Liu, et al. (2005). Cancer Res 65(7): 2804-2814.
Patel, N. M., S. Nozaki, et al. (2000). Oncogene 19(36): 4159-4169.
Peddibhotla, S., Y. J. Dang, et al. (2007). Journal of the American Chemical Society 129(40): 12222-12231.
Ralstin, M. C., E. A. Gage, et al. (2006). Mol Cancer Res 4(6): 387-399.
Rodriguez, E. A., H. A. Lester, et al. (2006). Proc Natl Acad Sci USA 103(23): 8650-8655.
Shanmugam, R., P. Kusumanchi, et al. (2011). Int J Cancer 128(10): 2481-2494.
Shanmugam, R., P. Kusumanchi, et al. (2010). Prostate 70(10): 1074-1086.
Siedle, B., A. J. Garcia-Pineres, et al. (2004). J Med Chem 47(24): 6042-6054.
Skalska, J., P. S. Brookes, et al. (2009). PLoS One 4(12): e8115.
Steele, A. J., D. T. Jones, et al. (2006). Leukemia 20(6): 1073-1079.
Sun, C. M., W. J. Syu, et al. (2003). J Nat Prod 66(9): 1175-1180.
Sun, Y., D. K. St Clair, et al. (2007). Mol Cancer Ther 6(9): 2477-2486.

Sun, Y., D. K. St Clair, et al. (2010). Cancer Res 70(7): 2880-2890.
Suvannasankha, A., C. D. Crean, et al. (2008). Clin Cancer Res 14(6): 1814-1822.
Sweeney, C. J., S. Mehrotra, et al. (2005). Mol Cancer Ther 4(6): 1004-1012.
Tiuman, T. S., T. Ueda-Nakamura, et al. (2005). Antimicrobial Agents and Chemotherapy 49(1): 176-182.
Tran, N. H., N. Huynh, et al. (2011). Chem Commun (Camb) 47(43): 11936-11938.
van der Donk, W. A. and H. Zhao (2003). Curr Opin Biotechnol 14(4): 421-426.
van Rhenen, A., N. Feller, et al. (2005). Clin Cancer Res 11(18): 6520-6527.
Wang, W., M. Adachi, et al. (2006). Apoptosis 11(12): 2225-2235.
Wang, W., M. Adachi, et al. (2009). Pancreas 38(4): e114-123.
Wen, J., K. R. You, et al. (2002). J Biol Chem 277(41): 38954-38964.
Won, Y. K., C. N. Ong, et al. (2005). Carcinogenesis 26(12): 2149-2156.
Won, Y. K., C. N. Ong, et al. (2004). Carcinogenesis 25(8): 1449-1458.
Woods, J. R., H. Mo, et al. (2011). J Med Chem 54(22): 7934-7941.
Wyrebska, A., K. Gach, et al. (2012). Chem Biol Drug Des 79(1): 112-120.
Yip-Schneider, M. T., H. Nakshatri, et al. (2005). Mol Cancer Ther 4(4): 587-594.
Yip-Schneider, M. T., H. Wu, et al. (2008). Pancreas 37(3): e45-53.
Zanotto-Filho, A., E. Braganhol, et al. (2011). Biochemical Pharmacology 81(3): 412-424.
Zhang, D., L. Qiu, et al. (2009). Mol Cancer Res 7(7): 1139-1149.
Zhang, K., S. El Damaty, et al. (2011). J. Am. Chem. Soc. 133(10): 3242-3245.
Zhang, K., B. M. Shafer, et al. (2012). J Am Chem Soc 134(45): 18695-18704.
Zhang, S., C. N. Ong, et al. (2004). Cancer Lett 208(2): 143-153.
Zhang, S., C. N. Ong, et al. (2004). Cancer Lett 211(2): 175-188.
Zhao, H. and W. A. van der Donk (2003). Curr Opin Biotechnol 14(6): 583-589.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A compound of one of general formula (A) and general formula (B), or a pharmaceutically acceptable salt thereof,

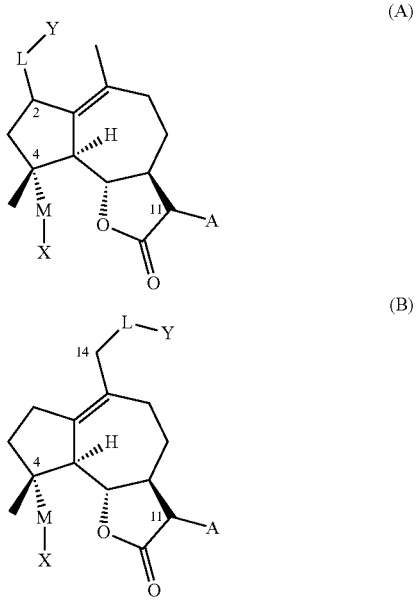

A is =CH$_2$ or —CH$_2$R* wherein R* is an amino acid residue bonded to the A methylene via a nitrogen or sulfur atom; or R* is —NR$^1$R$^2$, —NR$^1$C(O)R$^2$, —NR$^1$CO$_2$R$^2$, or —SR$^1$, wherein R$^1$ and R$^2$ are independently selected from the group consisting of H and an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group; or R* is —NR'R$^2$, wherein R$^1$ and R$^2$ optionally together with the nitrogen atom form an optionally substituted 5-12 membered ring, the ring optionally comprising at least one heteroatom or group selected from the group consisting of —CO—, —SO—, —SO$_2$—, and —PO—;
L is —O—, —NH—, —NHC(O)—, —OC(O)—, —OC(O)NH—, —S—, —SO—, —SO$_2$—, —PO—, —OCH$_2$—, or a chemical bond connecting the carbon atom to Y; and
Y represents an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group, wherein -L-Y together with the carbon atom at position C2 optionally forms carbonyl; or
Y is absent and L represents a halogen atom, an azido group (—N$_3$), an optionally substituted triazole group, or a group —NR$^3$R$^4$, where R$^3$ represents a hydrogen atom or an optionally substituted alkyl, alkenyl, or alkynyl group; R$^4$ represents an optionally substituted alkyl, alkenyl, alkynyl, aryl, or heteroaryl group; or where R$^3$ and R$^4$ are connected together to form an optionally substituted heterocyclic group;
M is —O— or —OC(O)— and X represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group.

2. The compound of claim 1, wherein A is =CH$_2$ or CH$_2$R*, where R* is selected from the group consisting of methylamino (—NH(CH$_3$)), dimethylamino (—N(CH$_3$)$_2$), methylethylamino (—N(CH$_3$)(CH$_2$CH$_3$)), methylpropylamino (—N(CH$_3$)(CH$_2$CH$_2$CH$_3$)), methylisopropylamino (—(CH$_3$)(CH$_2$(CH$_3$)$_2$), (—N(CH$_3$)(CH$_2$CH$_2$OH), pyrrolidine, piperidine, 4-methylpiperidine, 1-phenylmethanamine (—NCH$_2$Ph), and 2-phenylethanamine (—NCH$_2$CHPh); M is —O—, or —OC(O) —; X is hydrogen, —(C$_6$-C$_{10}$) aryl, —(5-14 membered) heteroaryl, (C$_1$-C$_6$) alkyl, —N(CH$_3$)$_2$—(C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; and either
(a) L is —OC(O)—; Y is —(C$_6$-C$_{10}$) aryl, -(5-14 membered) heteroaryl, —(C$_1$-C$_6$) alkyl, —CH$_2$—(C$_6$-C$_{10}$) aryl, or —NH—(C$_6$-C$_{10}$) aryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; or
(b) L is —O—; Y is —C(O)—(C$_6$-C$_{10}$) aryl, —C(O)—-(5-14 membered) heteroaryl, —CH$_2$—(C$_6$-C$_{10}$) aryl, —C(O)—NH—(C$_6$-C$_{10}$) aryl, or —(C$_1$-C$_6$) alkyl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

3. The compound of claim 2, wherein Y is —(C$_6$-C$_{10}$) aryl, -(5-14 membered) heteroaryl, or —NH—(C$_6$-C$_{10}$) aryl, each of which is optionally substituted with 1 to 3 substituents selected from the group consisting of —CF$_3$, halogen, phenyl, and phenyl substituted with 1 to 2 substituents selected from —CF$_3$ and halogen; A is =CH$_2$; M is —O—, or —OC(O)—; X is hydrogen, —(C$_6$-C$_{10}$) aryl, -(5-14 membered) heteroaryl, each of which is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; and
L is —OC(O)— or —O—.

4. The compound of claim 1, wherein -L-Y is azide, -(5-14 membered) heteroaryl, amino, halogen, —NH—C(O)—(C$_6$-C$_{10}$) aryl, wherein -(5-14 membered) heteroaryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$; M is —O—; X is hydrogen, or —C(O)—(C$_6$-C$_{10}$) aryl, wherein —C(O)—(C$_6$-C$_{10}$) aryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen.

5. The compound of claim 4, wherein -L-Y is -(5-14 membered) heteroaryl, halogen, wherein -(5-14 membered) heteroaryl is optionally substituted with 1 to 3 substituents selected from the group consisting of —CF$_3$, —N(CH$_3$)$_2$, —CH$_3$, halogen, phenyl and phenyl substituted with 1 to 2 substituents selected from —CF$_3$ and halogen; A is =CH$_2$; X is hydrogen, or —C(O)—(C$_6$-C$_{10}$) aryl, wherein —C(O)—(C$_6$-C$_{10}$) aryl is optionally substituted with 1 to 3 substituents selected from the group consisting of —CF$_3$, —N(CH₃)₂, —CH₃, halogen, phenyl and phenyl substituted with 1 to 2 substituents selected from —CF₃ and halogen.

6. The compound of claim 1, wherein L is —OC(O)—; Y is selected from the group consisting of phenyl, 4-pyridyl, (4-dimethylamino)phenyl, para-, meta-, and ortho-fluoro-phenyl, para-, meta-, and ortho-trifluoromethyl-phenyl, (2,4-bis-trifluoromethyl)phenyl, (3,5-bis-trifluoromethyl)phenyl, 1- and 2-naphthyl, 3-N-methyl-indolyl, 5-(4-chlorophenyl)isoxazolyl, 2-(4-bromophenyl)furanyl, 2-(2-(trifluoromethyl)phenyl)furanyl, and thiophene;
   A is =CH₂ or —CH₂R*, where R* is selected from the group consisting of methylamino (—NH(CH₃)), dimethylamino (—N(CH3)2), methylethylamino (—N(CH₃)(CH₂CH₃)), methylpropylamino (—N(CH₃)(CH₂CH₂CH₃)), methylisopropylamino (—(CH₃)(CH₂(CH₃)₂), (—N(CH₃)(CH₂CH₂OH), pyrrolidine, piperidine, 4-methylpiperidine, 1-phenylmethanamine (—NCH₂Ph), and 2-phenylethanamine (—NCH₂CHPh); and either
   (a) M is —OC(O)— and X is selected from the group consisting of phenyl, 4-pyridyl, (4-dimethylamino)phenyl, para-, meta-, and ortho-fluoro-phenyl, para-, meta-, and ortho-trifluoromethyl-phenyl, (2,4-bis-trifluoromethyl)phenyl, (3,5-bis-trifluoromethyl)phenyl, 1- and 2-naphthyl, 3-N-methyl-indolyl, 5-(4-chlorophenyl)isoxazolyl, 2-(4-bromophenyl)furanyl, 2-(2-(trifluoromethyl)phenyl)furanyl, and thiophene; or
   (b) M is —O— and X represents a hydrogen atom.

7. The compound of claim 1, wherein L is —O—; Y is selected from the group consisting of (phenyl)methyl, (4-pyridyl)methyl, (4-dimethylaminophenyl)methyl, (para-, meta-, and ortho-fluoro-phenyl)methyl, (para-, meta-, and ortho-trifluoromethyl-phenyl)methyl, (2,4-bis-trifluoromethyl-phenyl)methyl, (3,5-bis-trifluoromethyl-phenyl)methyl, (naphthyl)methyl, (3-N-methyl-indolyl)methyl, (5-(4-chlorophenyl)isoxazolyl)methyl, (2-(4-bromophenyl)furanyl)methyl, (2-(2-(trifluoromethyl)phenyl)furanyl)methyl, methyl(thiophene) and —CH(Ar')COOR' group, where Ar' is selected from the group consisting of phenyl, 4-pyridyl, (4-dimethylamino)phenyl, para-, meta-, and ortho-fluoro-phenyl, para-, meta-, and ortho-trifluoromethyl-phenyl, (2,4-bis-trifluoromethyl)phenyl, (3,5-bis-trifluoromethyl)phenyl, 1- and 2-naphthyl, 3-N-methyl-indolyl, 5-(4-chlorophenyl)isoxazolyl, 2-(4-bromophenyl)furanyl, 2-(2-(trifluoromethyl)phenyl)furanyl, and thiophene group, and R' is selected from the group consisting of methyl, ethyl, propyl, isopropyl, tert-butyl, benzyl, 2-morpholinoethyl, 2-morpholinoethyl, 2-(piperidin-1-yl)ethyl, and 2-(pyrrolidin-1-yl)ethyl, M is —O—; X represents a hydrogen atom; and A is =CH₂ or —CH₂R*, where R* is selected from the group consisting of methylamino (—NH(CH₃)), dimethylamino (—N(CH₃)₂), methylethylamino (—N(CH₃)(CH₂CH₃)), methylpropylamino (—N(CH₃)(CH₂CH₂CH₃)), methylisopropylamino (—(CH₃)(CH₂(CH₃)₂), —N(CH₃)(CH₂CH₂OH), pyrrolidine, piperidine, 4-methylpiperidine, 1-phenylmethanamine (—NCH₂Ph), and 2-phenylethanamine (—CH₂CH₂Ph).

8. A method for inhibiting cancer cell growth in a mammal, the method comprising the step of administering to the mammal afflicted with cancer an amount of a compound of claim 1 effective to inhibit the growth of the cancer cells.

9. A method for reducing or controlling an inflammatory condition in a mammal, the method comprising the step of administering to the mammal in need thereof, an amount of a compound of claim 1 effective to reduce or control the condition.

10. A method comprising administering an effective amount of a compound of claim 1 to a patient having acute myeloid leukemia (AML), chronic myeloid leukemia (CML), acute lymphoblastic leukemia (ALL), mantle cell lymphoma (MCL), or large B-cell lymphoma.

11. A method for treating bone marrow for human bone marrow transplant treatment of leukemia in a patient, comprising the step of treating bone marrow with a compound of claim 1 prior to reintroducing bone marrow into the patient.

12. A method for inhibiting angiogenesis in a patient in need thereof, the method comprising the step of administering to the patient an effective amount of a compound of claim 1.

13. A method comprising administering an effective amount of a compound of claim 1 to a patient with a tumor.

14. The method of claim 13, wherein the tumor is a prostate cancer, a brain cancer, a neuroblastoma, a lung cancer, a breast cancer, a skin cancer, a cervical cancer, a colon cancer, an ovary cancer, or a pancreatic cancer.

* * * * *